(12) United States Patent
Sahler et al.

(10) Patent No.: US 11,779,739 B2
(45) Date of Patent: Oct. 10, 2023

(54) DRUG DELIVERY SYSTEM AND METHOD

(71) Applicant: Perfect IP, LLC, Dallas, TX (US)

(72) Inventors: Ruth Sahler, Irvine, CA (US); Steven Edward Smathers, Dallas, TX (US)

(*) Notice: Subject to any disclaimer, the term of this patent is extended or adjusted under 35 U.S.C. 154(b) by 719 days.

(21) Appl. No.: 16/717,131

(22) Filed: Dec. 17, 2019

(65) Prior Publication Data

US 2020/0203023 A1 Jun. 25, 2020

Related U.S. Application Data

(60) Provisional application No. 62/783,320, filed on Dec. 21, 2018.

(51) Int. Cl.
| | |
|---|---|
| *A61M 31/00* | (2006.01) |
| *G16H 70/40* | (2018.01) |
| *G16H 20/17* | (2018.01) |
| *A61N 5/06* | (2006.01) |
| *A61N 5/067* | (2006.01) |

(52) U.S. Cl.
CPC ............ *A61M 31/002* (2013.01); *A61N 5/06* (2013.01); *G16H 20/17* (2018.01); *G16H 70/40* (2018.01); *A61N 5/067* (2021.08)

(58) Field of Classification Search
CPC ..... G16H 70/40; G16H 70/17; A61M 31/002; A61M 35/003; A61N 5/06; A61N 5/067
See application file for complete search history.

(56) References Cited

U.S. PATENT DOCUMENTS

| | | | | |
|---|---|---|---|---|
| 2004/0191308 | A1* | 9/2004 | Mosack | A61K 9/0051 424/451 |
| 2012/0041778 | A1* | 2/2012 | Kraft | G16Z 99/00 215/250 |
| 2014/0135920 | A1* | 5/2014 | Sahler | A61F 2/1613 606/4 |
| 2016/0296662 | A1* | 10/2016 | Stoy | A61F 2/1627 |
| 2017/0173262 | A1* | 6/2017 | Veltz | G16H 20/17 |

OTHER PUBLICATIONS

International Search Report for PCT/US19/67771 (claiming benefit of U.S. Appl. No. 16/717,131), dated Apr. 30, 2020.
Applicant Comments to International Search Report for PCT/US19/67771 (claiming benefit of U.S. Appl. No. 16/717,131), dated Oct. 19, 2020.

* cited by examiner

*Primary Examiner* — Philip R Wiest
(74) *Attorney, Agent, or Firm* — Kevin Mark Klughart

(57) ABSTRACT

A customizable drug delivery system and method utilizing a laser pattern generator (LPG) to define application of a drug delivery payload (DDP) contained within a drug delivery device (DDD) to a drug delivery target (DDT) is disclosed. A computer control device (CCD) supervises the LPG to select a drug payload pathway (DPP) from a drug pathway database (DPD) and writes the selected DPP to the DDD. This pathway patterning process (PPP) modifies the hydrophilic properties of the DDD and enables the DDD to selectively attract and absorb the DDP. The DDD is then injected with the DDP or exposed for drug exposure time (DET) by the CCD and DPD during which the DPP written to the DDD absorbs a controlled amount of DDP. The DDD when subsequently inserted into a drug delivery target (DDT) delivers the DDP to the DDT under controlled delivery rates defined by the DPP and the DET.

20 Claims, 64 Drawing Sheets

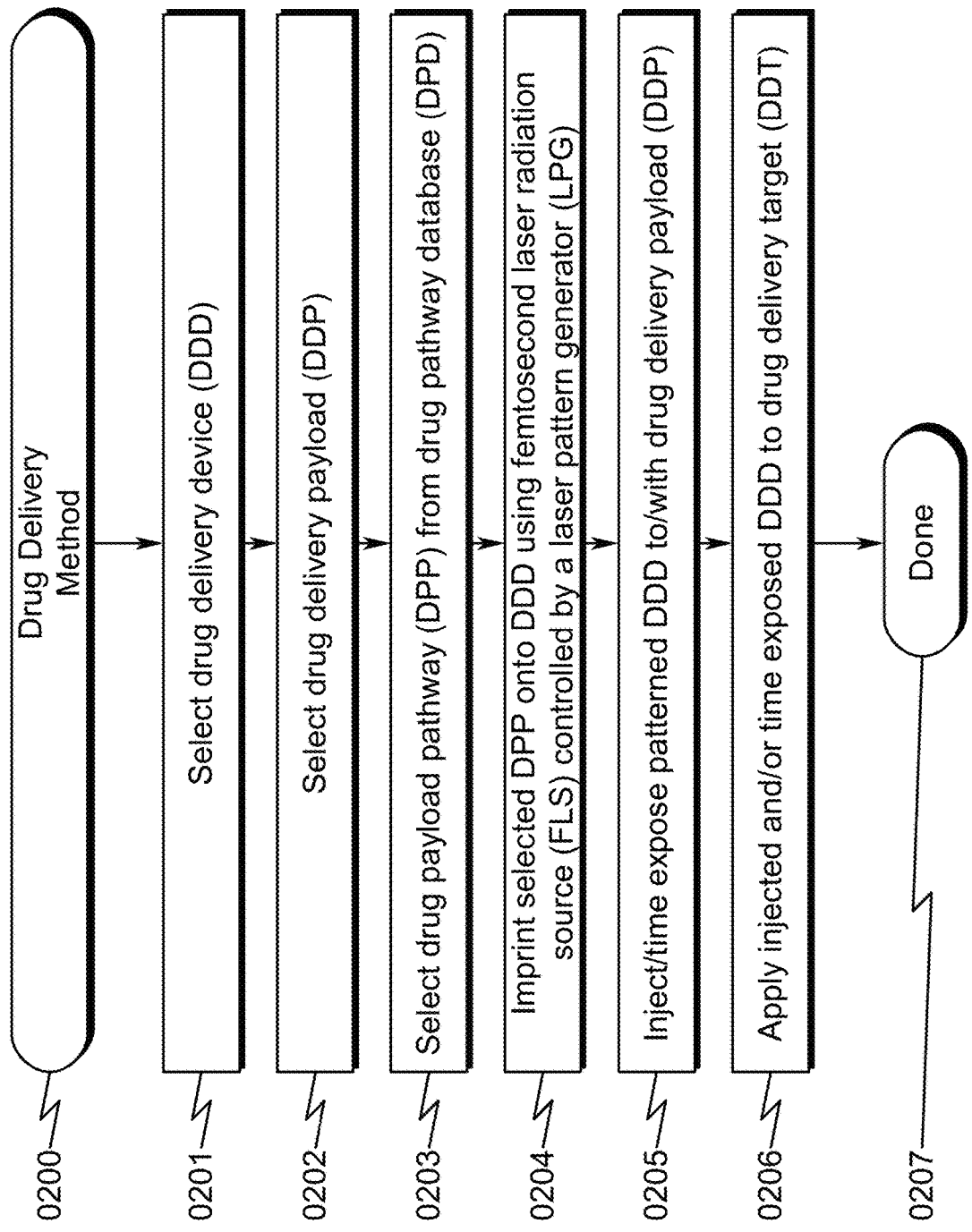

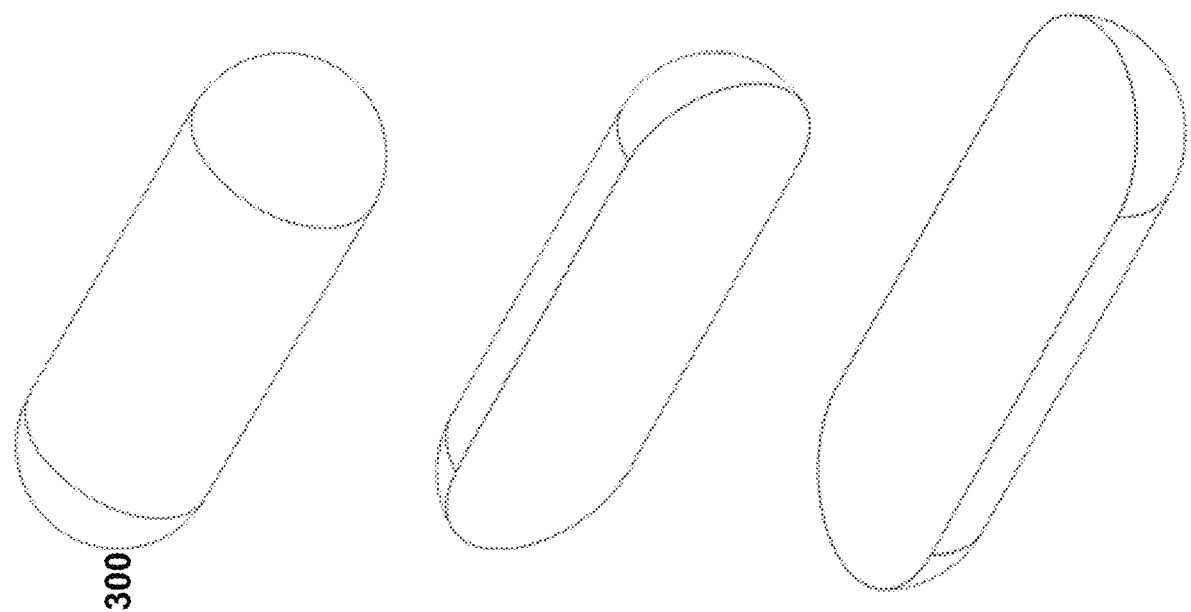
FIG. 3 ↙ 0300
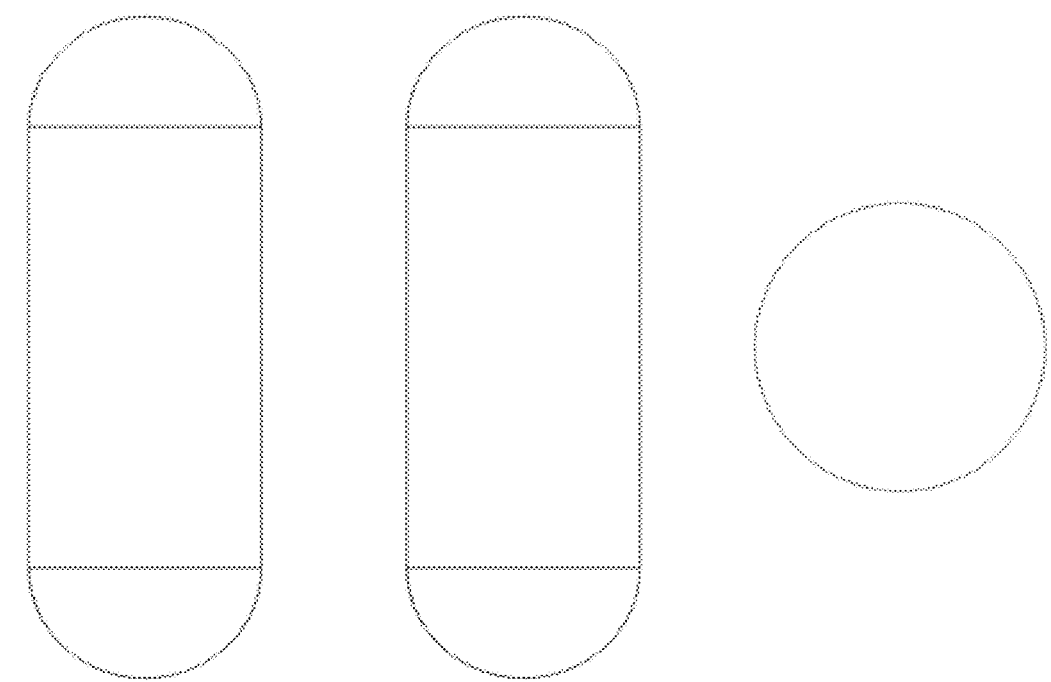

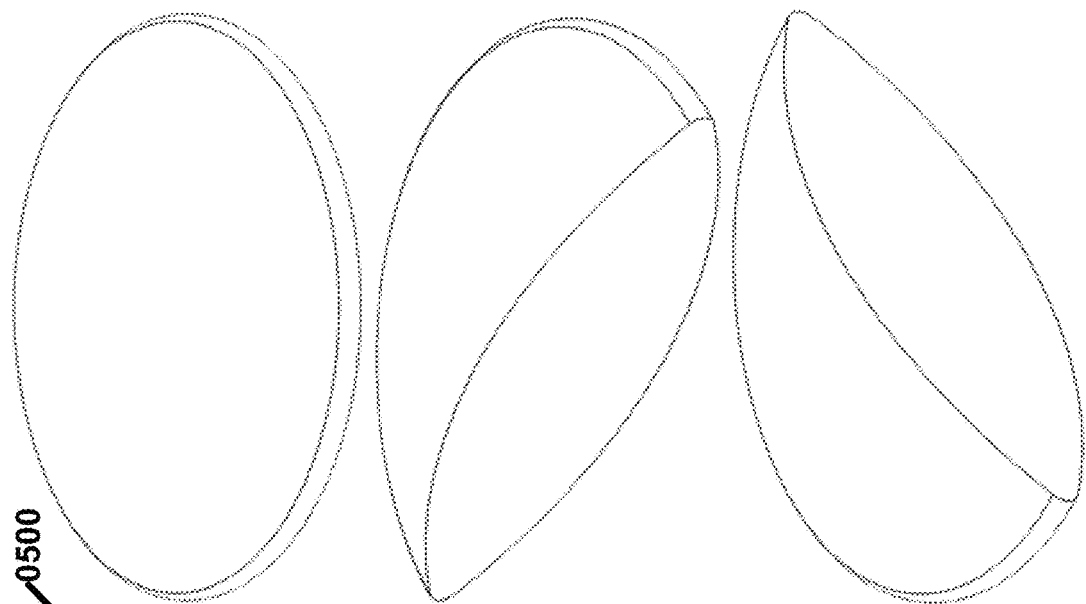
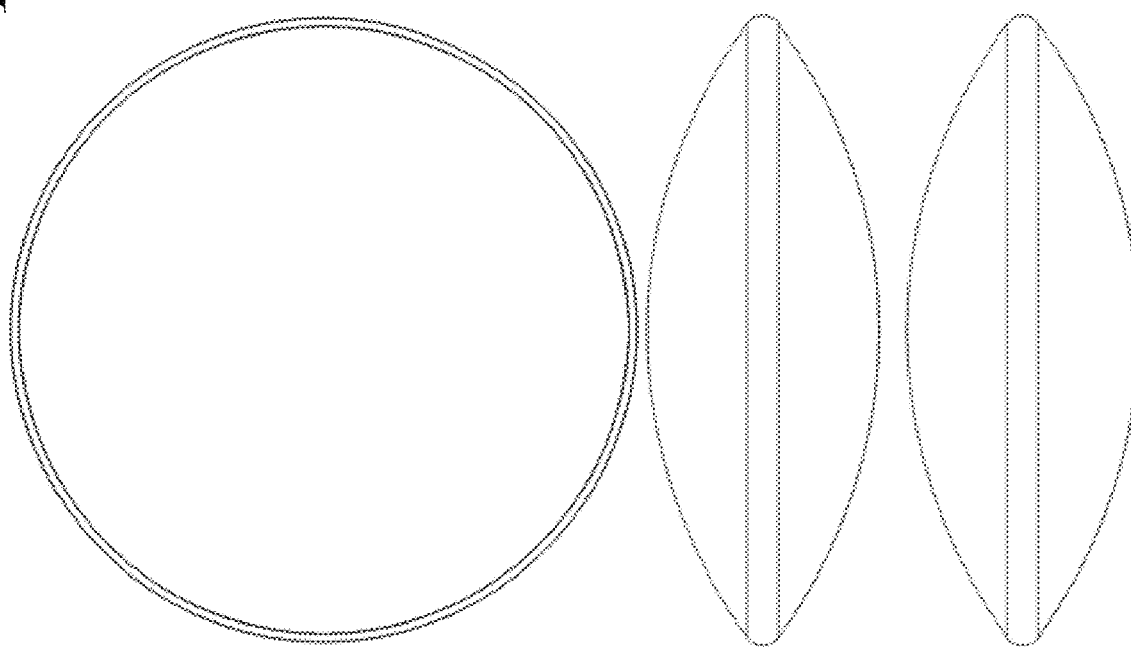
FIG. 5
0500

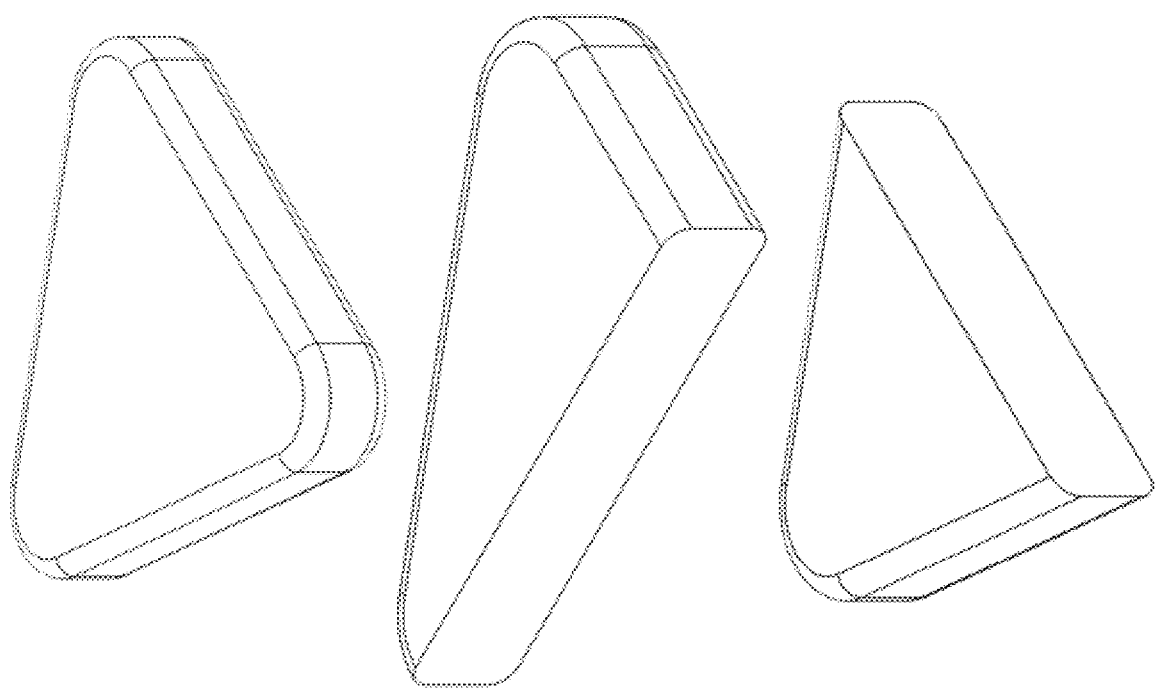
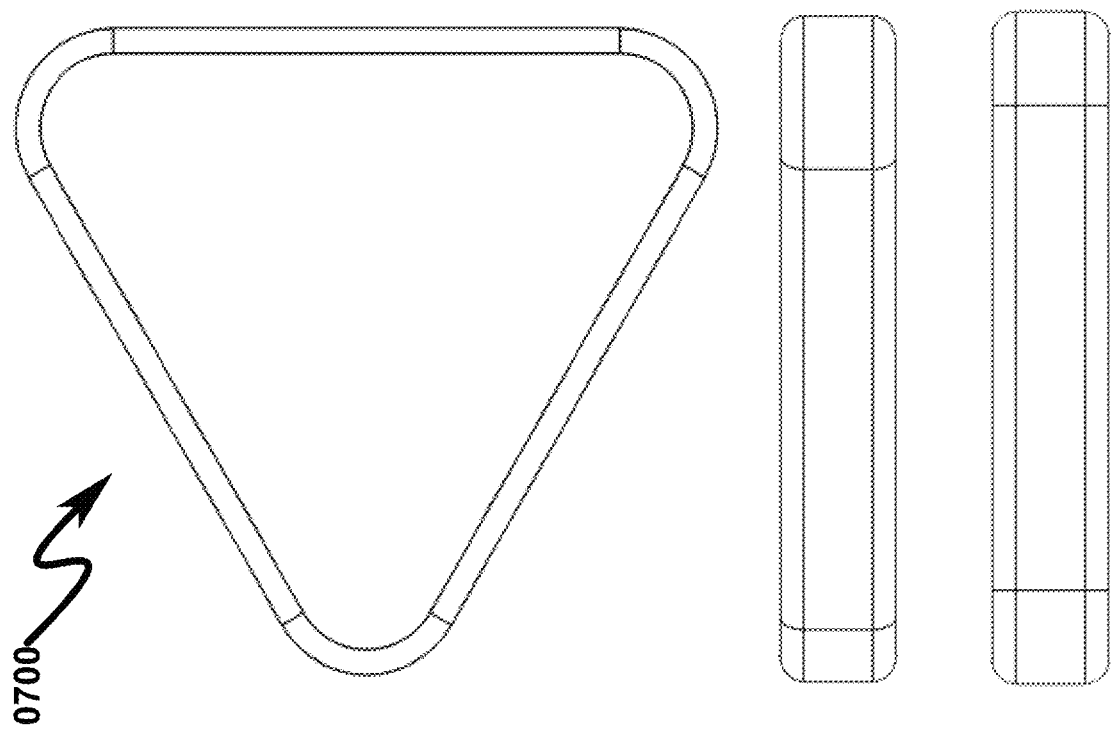
FIG. 7

2400

DRUG DELIVERY SYSTEM AND METHOD

CROSS REFERENCE TO RELATED APPLICATIONS

Utility Patents

This patent application includes by reference U.S. Pat. No. 9,023,257 Ser. No. 13/843,464 issued on May 5, 2015.

Provisional Patent Applications

This United States Utility Patent Application claims benefit under 35 U.S.C. § 119 and incorporates by reference United States Provisional Patent Application for DRUG DELIVERY SYSTEM AND METHOD by inventors Ruth (nmn) Sahler and Steven Edward Smathers, filed electronically with the USPTO on Dec. 21, 2018, with Ser. No. 62/783,320, EFSID 34668102, confirmation number 4042.

PARTIAL WAIVER OF COPYRIGHT

All of the material in this patent application is subject to copyright protection under the copyright laws of the United States and of other countries. As of the first effective filing date of the present application, this material is protected as unpublished material.

However, permission to copy this material is hereby granted to the extent that the copyright owner has no objection to the facsimile reproduction by anyone of the patent documentation or patent disclosure, as it appears in the United States Patent and Trademark Office patent file or records, but otherwise reserves all copyright rights whatsoever.

STATEMENT REGARDING FEDERALLY SPONSORED RESEARCH OR DEVELOPMENT

Not Applicable

REFERENCE TO A MICROFICHE APPENDIX

Not Applicable

FIELD OF THE INVENTION

The present invention relates to a system and method for controlling drug delivery of a drug delivery payload (DDP) to a drug delivery target (DDT).

PRIOR ART

U.S. Pat. No. 9,023,257 Ser. No. 13/843,464 issued on May 5, 2015 describes the use of a femtosecond laser to adjust the hydrophilicity of an acrylic material that has been impregnated with an ultraviolet (UV) absorber having a concentration of 2% or less. The energy from the laser initiates a two-photon reaction in which certain ester molecules in the acrylic material or the absorber are split. The split creates residual polar molecules that attract water molecules. By regulating the laser energy and its application one may create hydrophilic molecules within the material wherever desired. These polar molecules allow the creation of an osmotic gradient within the acrylic material. Depending on the drug and its constituents the acrylic material may be adjusted such that the trapped drug will migrate at a defined rate into surrounding tissue.

The journal article "Chemical Basis for Alteration of an Intraocular Lens Using a Femtosecond Laser" published in BIOMEDICAL OPTICS EXPRESS, VOL. 8, NO. 3, 1 Mar. 2017, pages 1390-1404 describes the chemical basis for the alteration of the refractive properties of an intraocular lens with a femtosecond laser using three different microscope setups.

BRIEF SUMMARY OF THE INVENTION

The present invention pertains to a system and method wherein a drug delivery payload (DDP) within a drug delivery device (DDD) is delivered to a designated area(s) on the DDD at a predetermined speed and concentration by virtue of drug payload pathway(s) (DPP) imprinted onto the DDD by a laser pattern generator (LPG). The present invention utilizes a capsule/button/disc/pouch/tab/intraocular lens ("IOL") created using a material (such as an acrylic material) that has been treated with a femtosecond laser power source (LPS) controlled by the LPG. The LPS creates hydrophilic DPP in the DDD that lead to the surface of the DDD material. The LPS will thus have created hydrophilic channels within the DDD. These hydrophilic channels are used to (1) deliver the DDP to the designated area or (2) deposit the DDP within the DDD. The DDD is implanted in subcutaneous tissue of a drug delivery target (DDT) and the drug migrates from the DDD in a regular manner over a significant period of time (hours to months given the drug and the channels created in the DDD). The DPP may provide for various rates and/or flows of DDP delivery dependent on the osmatic gradient within the material and subcutaneous tissue of the DDT. After use, the DDD capsule/button/disc/pouch/tab/IOL may be explanted or refilled using a syringe.

BRIEF DESCRIPTION OF THE DRAWINGS

For a fuller understanding of the advantages provided by the invention, reference should be made to the following detailed description together with the accompanying drawings wherein:

FIG. 2 illustrates a flowchart depicting a general overview of a preferred exemplary invention method embodiment;

FIG. 3 illustrates top, front, side, perspective, perspective front section, and perspective right section views of a preferred exemplary invention drug delivery device (DDD) capsule embodiment;

FIG. 5 illustrates top, front, side, perspective, perspective front section, and perspective right section views of a preferred exemplary invention drug delivery device (DDD) disc embodiment;

FIG. 7 illustrates top, front, side, perspective, perspective front section, and perspective right section views of a preferred exemplary invention drug delivery device (DDD) tab embodiment;

DESCRIPTION OF THE PRESENTLY PREFERRED EXEMPLARY EMBODIMENTS

Figure 1:
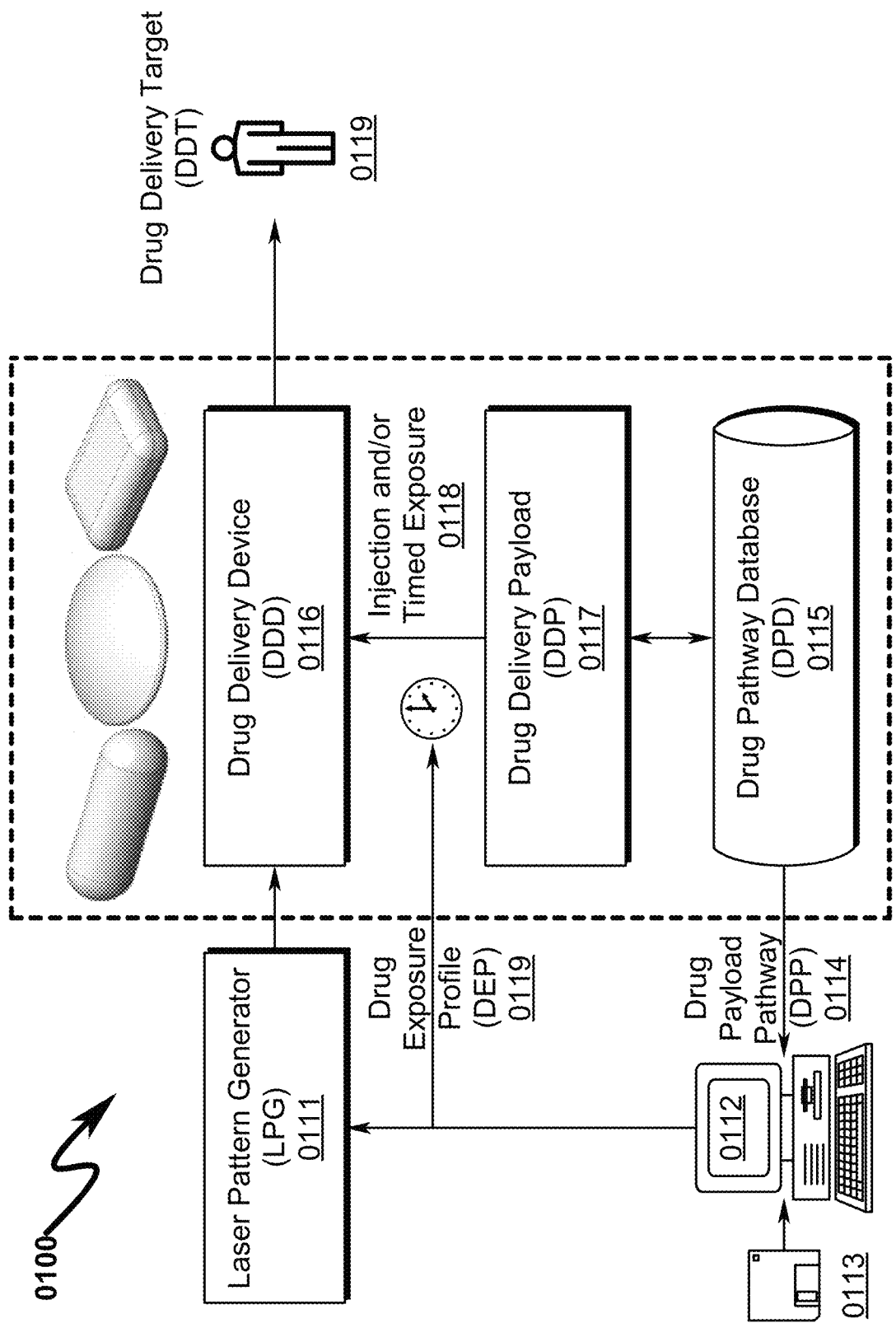
FIG. 1 illustrates a block diagram depicting a general overview of a preferred exemplary invention system embodiment.

While this invention is susceptible of embodiment in many different forms, there is shown in the drawings and will herein be described in detailed preferred embodiment of the invention with the understanding that the present disclosure is to be considered as an exemplification of the principles of the invention and is not intended to limit the broad aspect of the invention to the embodiment illustrated.

The numerous innovative teachings of the present application will be described with particular reference to the presently preferred embodiment, wherein these innovative teachings are advantageously applied to the particular problems of a DRUG DELIVERY SYSTEM AND METHOD. However, it should be understood that this embodiment is only one example of the many advantageous uses of the innovative teachings herein. In general, statements made in the specification of the present application do not necessarily limit any of the various claimed inventions. Moreover, some statements may apply to some inventive features but not to others.

General Laser Pattern Generator (LPG) Description

The present invention may be generally described as utilizing a laser pattern generator (LPG) which consists of a femtosecond laser source (FLS), an AOM, a scanner, and an objective which delivers the laser pulses into the predetermined region. The FLS preferably has a pulse duration of 450 fs or shorter, a wavelength in the range of 400 nm to 1060 nm, and a repetition rate in the range of 0.01 MHz to 100 MHz. The pulse energy is typically in the range of 0.1 nanojoules to 3500 nanojoules. Those who are skilled in the art understand that these laser parameters are approximate and may be adjusted and rebalanced to be outside above-specified range but still be able to achieve the same level of energy delivered to the targeted regions of the lens material.

Drug Delivery Payload Path (DPP) Surface Interface to DDD

The present invention as described herein includes several examples of drug delivery payload path (DPP) pathways that may be created on/within a variety of drug delivery devices (DDD). These DPP as depicted within the DDD are to be considered as reaching the surface of the DDD so as to provide a pathway from the internal portion of the depicted DDD to the surface of the DDD. This construction allows the drug delivery payload (DDP) to flow from the internal portion of the DDD to the drug delivery target (DDT). The exemplary DPP illustrated may in some depictions omit the surface interface of the DPP to the DDD, as this will be well understood by one skilled in the art and will by necessity vary based on the application context and construction of the DDD.

DPP Cross Section Exemplary

The exemplary DPP pathways depicted herein may indicate a uniform cross section. However, the present invention anticipates that the DPP cross section may vary along the DPP pathway and as such the ability of the DDD to retain the DDP may vary along the DPP pathway. Thus, the present invention scope is not limited to fixed cross section DPP pathways and the width/depth of these pathways may vary based on application context.

System Overview (0100)

A general overview of a preferred exemplary invention embodiment is generally depicted in FIG. 1 (0100), wherein a laser pattern generator (LPG) (0111) operated by a computer control device (CCD) (0112) executing machine instructions from a computer readable medium (0113) retrieves drug payload pathway (DPP) (0114) information from a drug pathway database (DPD) (0115). This DPP (0114) information is then used to pattern pathways within a drug delivery device (DDD) (0116) using the LPG (0111). During and after this patterning process the drug delivery payload (DDP) (0117) may be injected into the DDD (0116) or the DDD may be immersed in a drug delivery payload (DDP) (0117) under timed exposure (0118) using a drug exposure profile (DEP) (0119). The injection and/or timed exposure (0118) permits the delivery of the drug delivery payload (DDP) (0117) to the DDD (0116) generated by the LPG (0111) such that the drug delivery payload (DDP) (0117) is wicked into the body of the DDD (0116). Subsequent to this impregnation of the DDP (0117) into the DDD (0116) by injection and/or migration, the DDD (0116) may be implanted into a drug delivery target (DDT) (0120) for delivery of the DDP (0117) within the DDD (0116) to the DDT (0120) under delivery rates controlled by the DPP (0114) formed within the DDD (0116). While the predominant mode of filling and/or refilling the DDD is envisioned as a manual process (syringe) using an identifying indicia locator (IIL) (index, bump, notch, etc.) in the DDD, there may exist other mechanisms to fill the DDD.

The use of various DPP (0114) pathways in conjunction with various construction methodologies for the DDD (0116) permit the absorption and release of the DDP (0117) by the DDD (0116) to be controlled by information contained within the DPD (0115). Thus, the present invention allows a generic DDD (0116) form factor to be modified with a wide variety of internal modified hydrophilic pathways that allow the DDP (0117) to be delivered in a tailored fashion to the DDT (0120). Once the DDP (0117) has been successfully delivered to the DDT (0120), the DDD (0116) may be removed from the DDT (0120) or optionally refilled using a needle syringe or other refilling apparatus that utilizes the modified hydrophilic pathways within the DDD (0116) to continue delivery of the newly refilled DDP (0117) within the DDD (0116). The DDD (0116) may have a distinguishing mark which allows the DDD (0116) to be refilled at the correct location along the surface of the DDD (0116).

Method Overview (0200)

The present invention method anticipates a wide variety of variations in the basic theme of implementation, but may be generalized as depicted in FIG. 2 (0200) as a drug delivery method using hydrophilicity alteration comprising:
(1) selecting a drug delivery device (DDD) (0201);
(2) selecting a drug delivery payload (DDP) (0202);
(3) with a computer control device (CCD), selecting a drug payload pathway (DPP) from a drug pathway database (DPD) (0203);
(4) with the CCD, imprinting the selected DPP onto DDD using a femtosecond laser radiation source (FLS) controlled by a laser pattern generator (LPG) (0204);
(5) injecting and/or time exposing the patterned DDD to and/or with the drug delivery payload (DDP) (0205); and
(6) applying the injected and/or time exposed DDD to a drug delivery target (DDT) (0206).

This general method may be modified heavily depending on a number of factors, with rearrangement and/or addition/deletion of steps anticipated by the scope of the present invention. Integration of this and other preferred exemplary embodiment methods in conjunction with a variety of preferred exemplary embodiment systems described herein is anticipated by the overall scope of the present invention. This and other methods described herein are optimally executed under control of a computer system reading instructions from a computer readable media as described elsewhere herein.

Exemplary DDD Form Factors (0300)-(0800)

Figure 4:
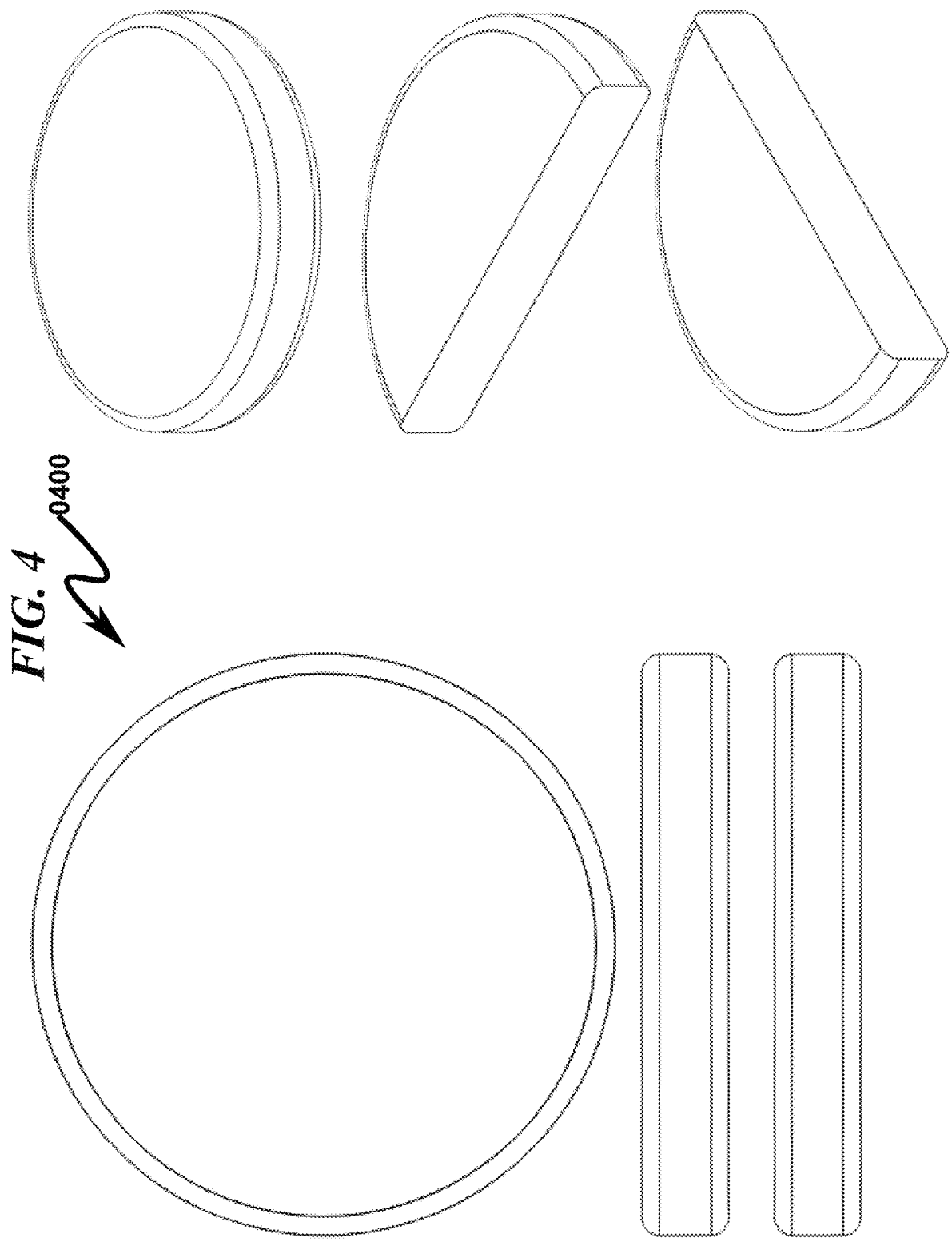
FIG. 4 illustrates top, front, side, perspective, perspective front section, and perspective right section views of a preferred exemplary invention drug delivery device (DDD) button embodiment.
Figure 6:
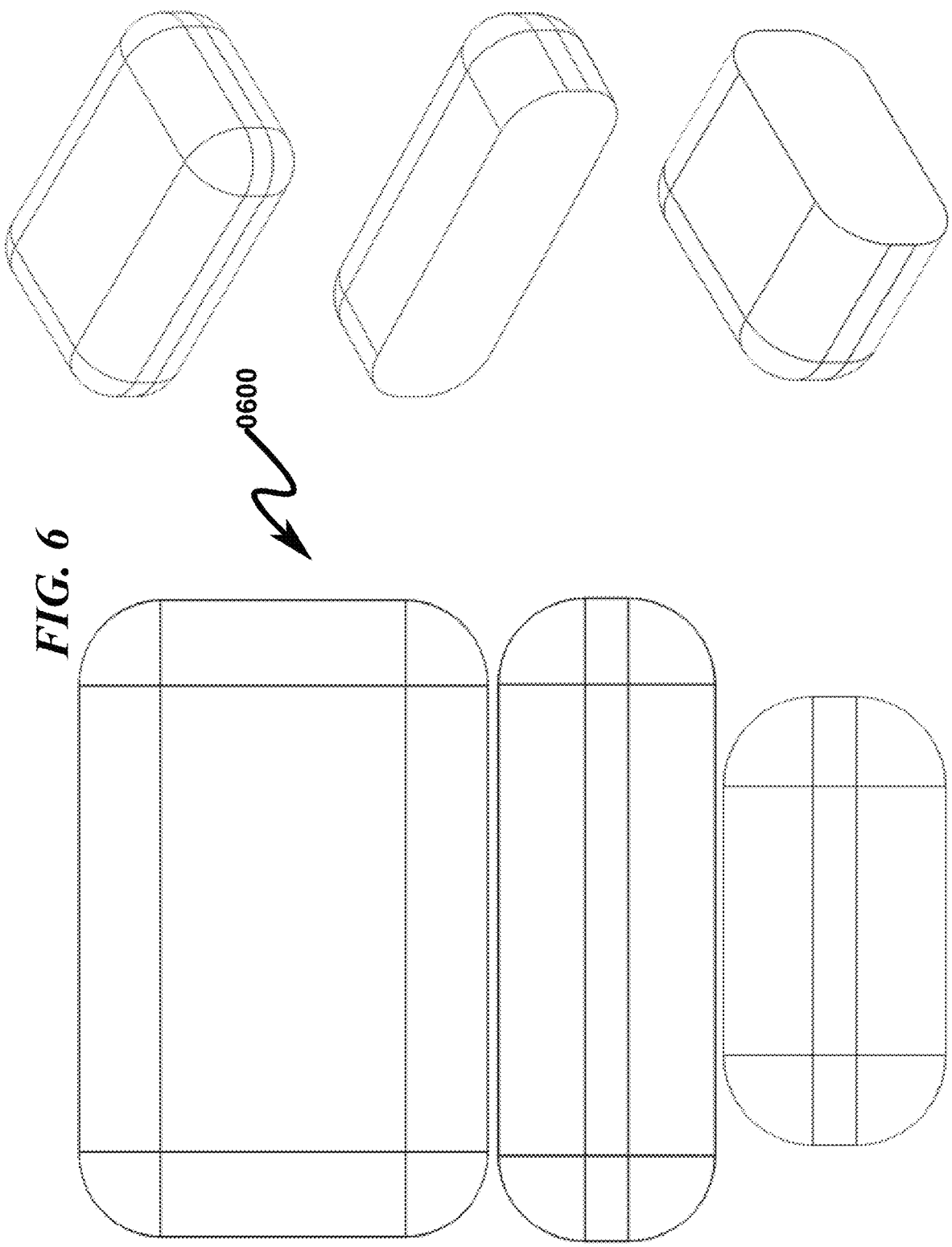
FIG. 6 illustrates top, front, side, perspective, perspective front section, and perspective right section views of a preferred exemplary invention drug delivery device (DDD) pouch embodiment.
Figure 8:
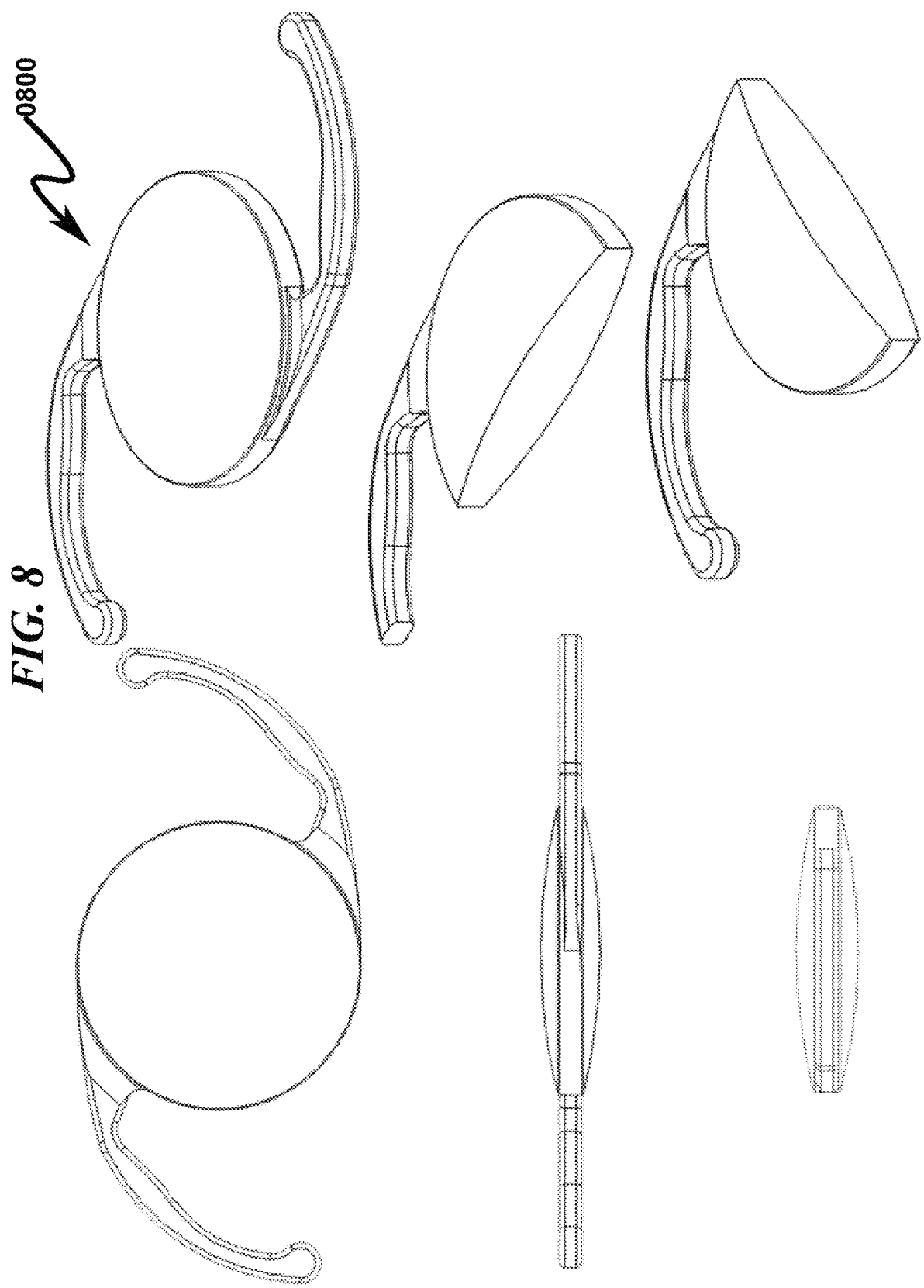
FIG. 8 illustrates top, front, side, perspective, perspective front section, and perspective right section views of a preferred exemplary invention drug delivery device (DDD) intraocular lens (IOL) embodiment.

FIG. 3 (0300)-FIG. 8 (0800) depict exemplary drug delivery device (DDD) form factors anticipated by the present invention, including capsule (FIG. 3 (0300)), button (FIG. 4 (0400)), disc (FIG. 5 (0500)), pouch (FIG. 6 (0600)), tab (FIG. 7 (0700)), and intraocular lens (FIG. 8 (0800)) form factors.

Exemplary DPP Form Factors (0900)-(1600)

Figure 9:
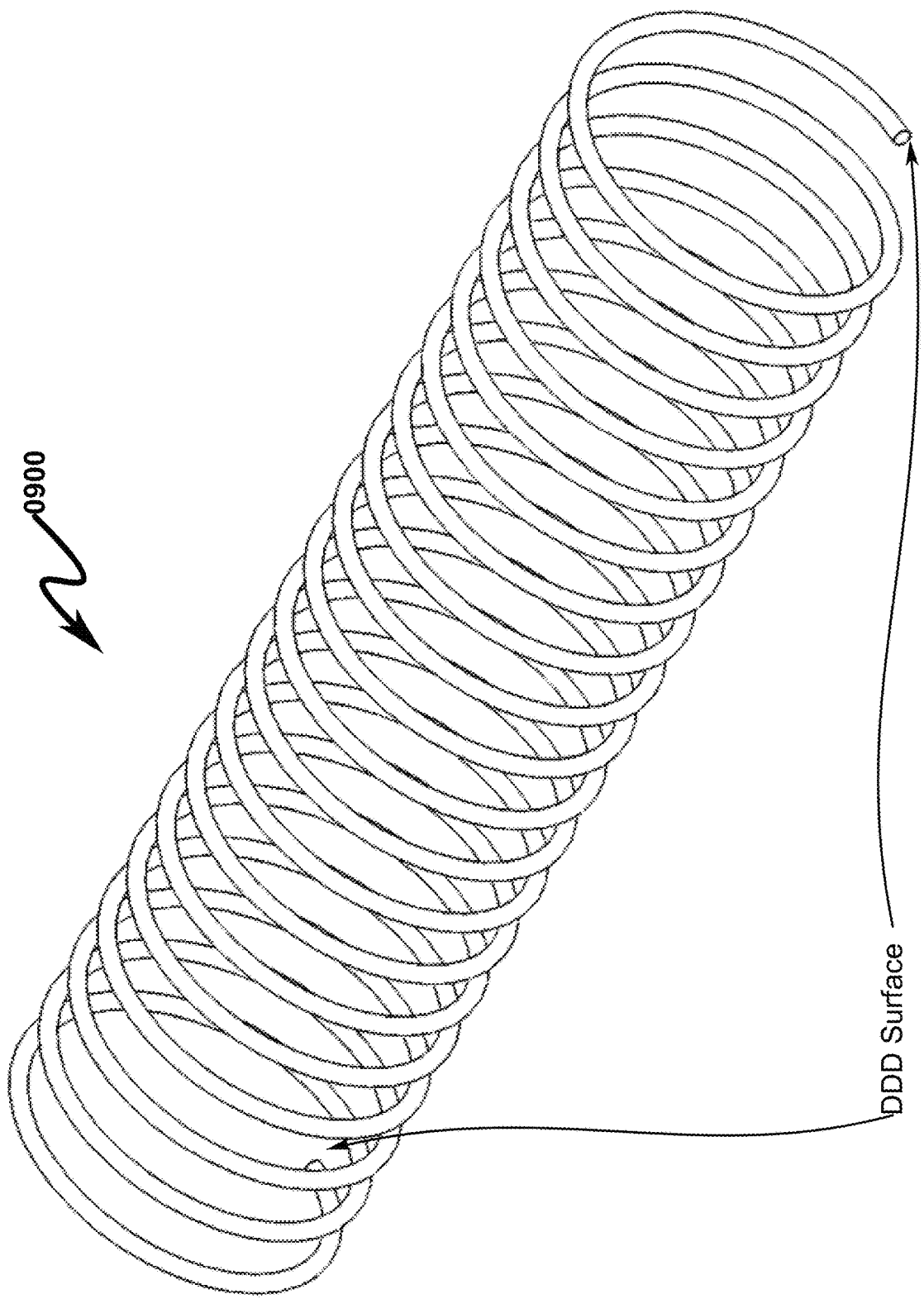
FIG. 9 illustrates a top perspective view of a preferred exemplary helix DPP form factor.
Figure 10:
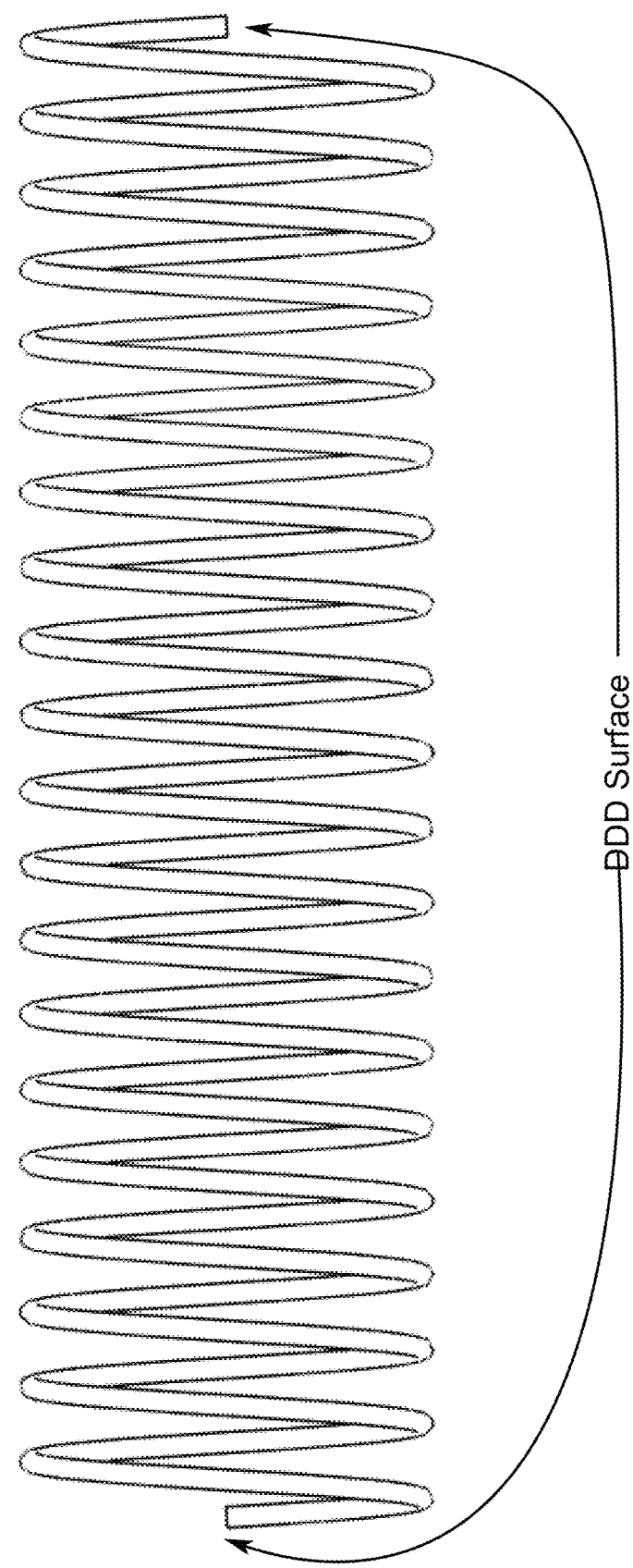
FIG. 10 illustrates a top view of a preferred exemplary helix DPP form factor.
Figure 11:
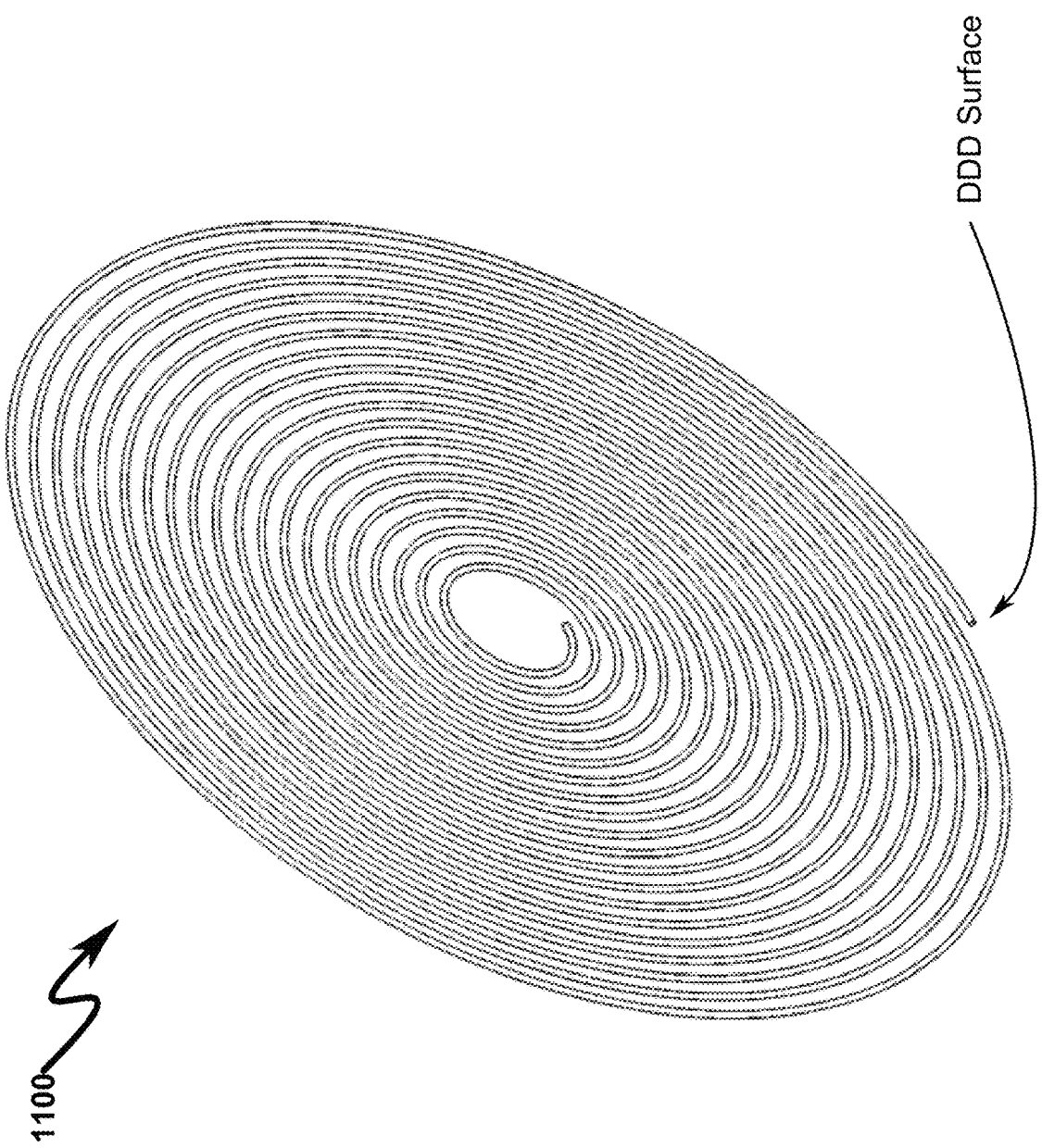
FIG. 11 illustrates a top perspective view of a preferred exemplary spiral DPP form factor.
Figure 12:
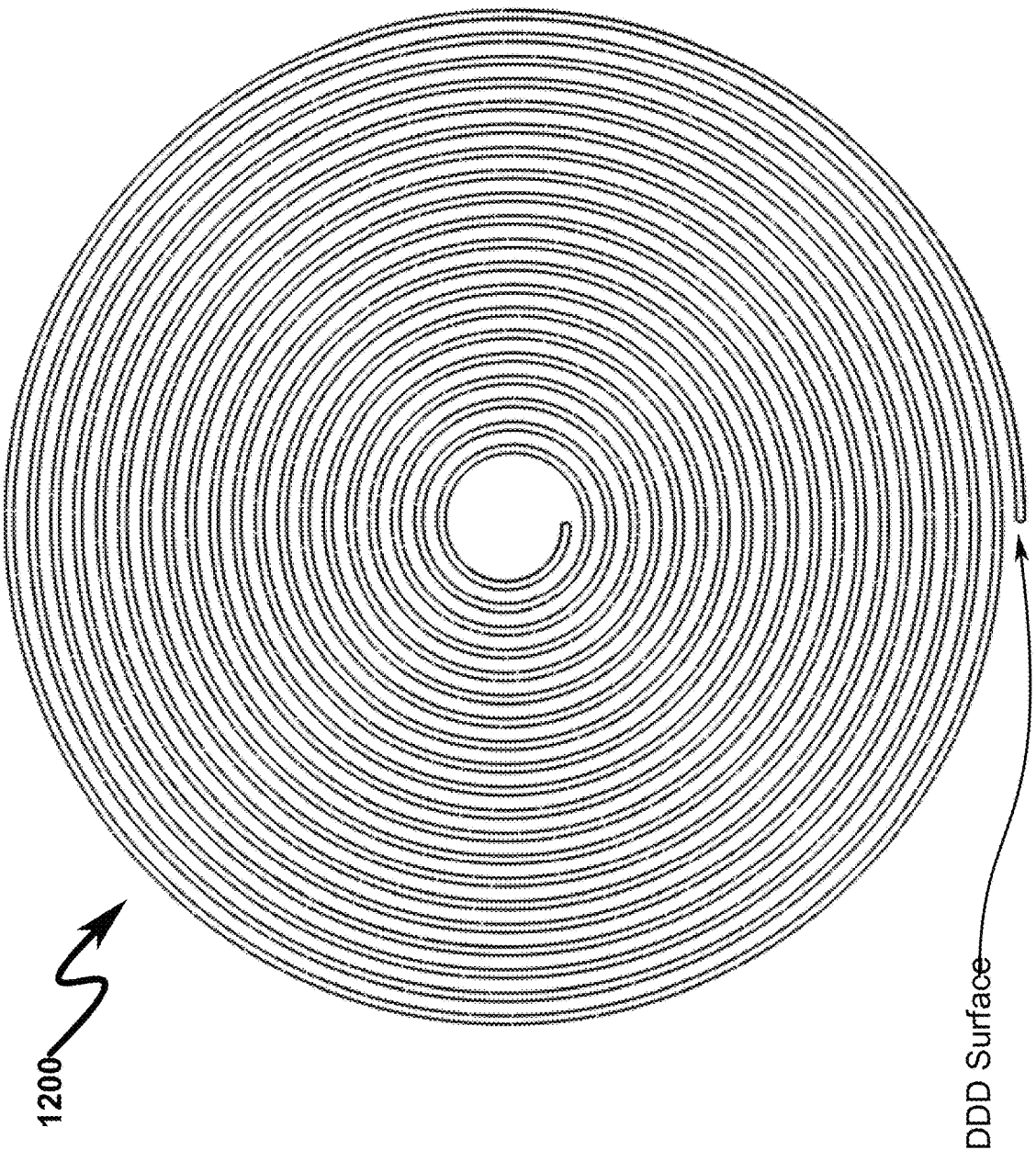
FIG. 12 illustrates a top view of a preferred exemplary spiral DPP form factor.
Figure 13:
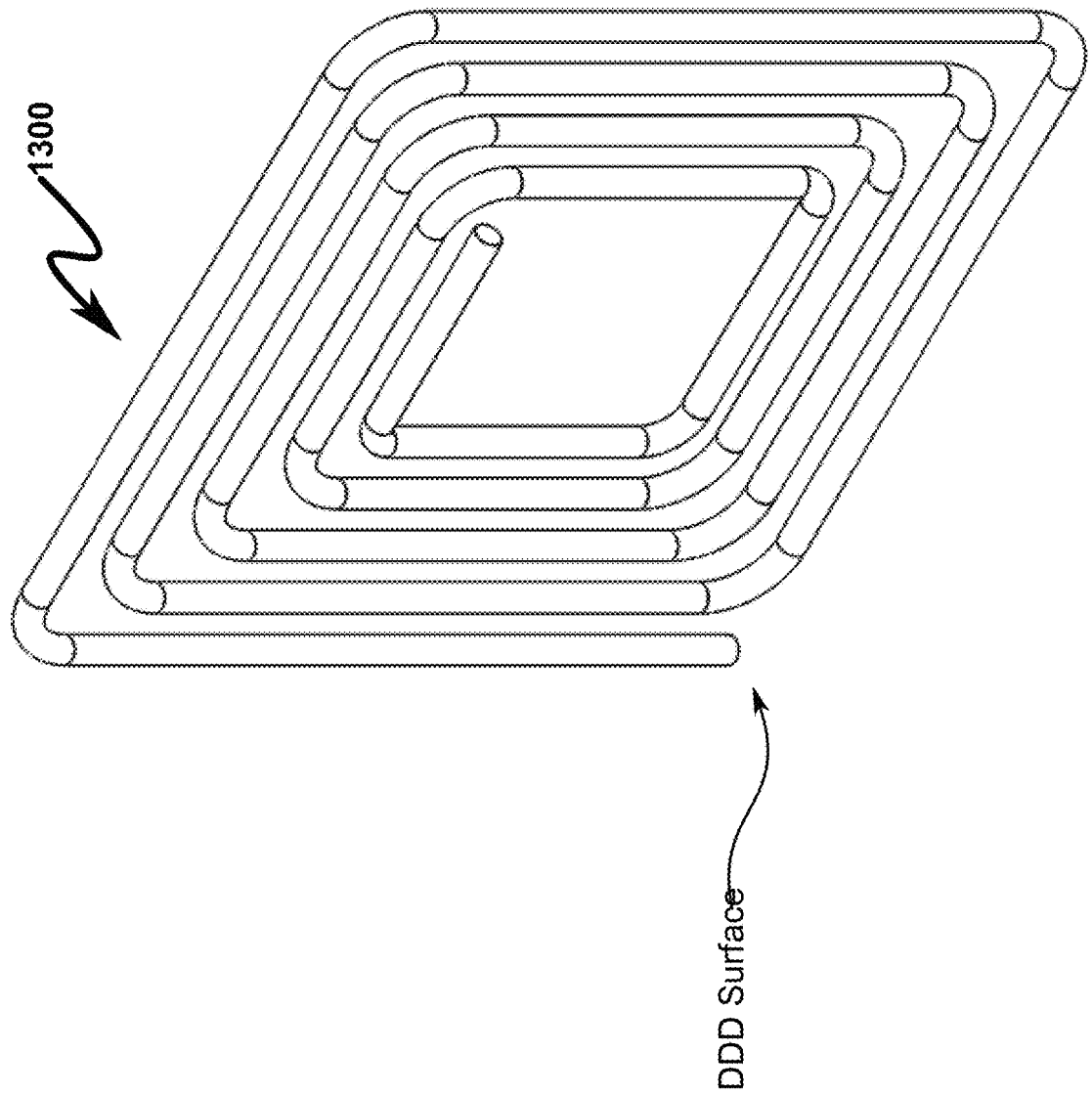
FIG. 13 illustrates a top perspective view of a preferred exemplary rectangular spiral DPP form factor.
Figure 14:
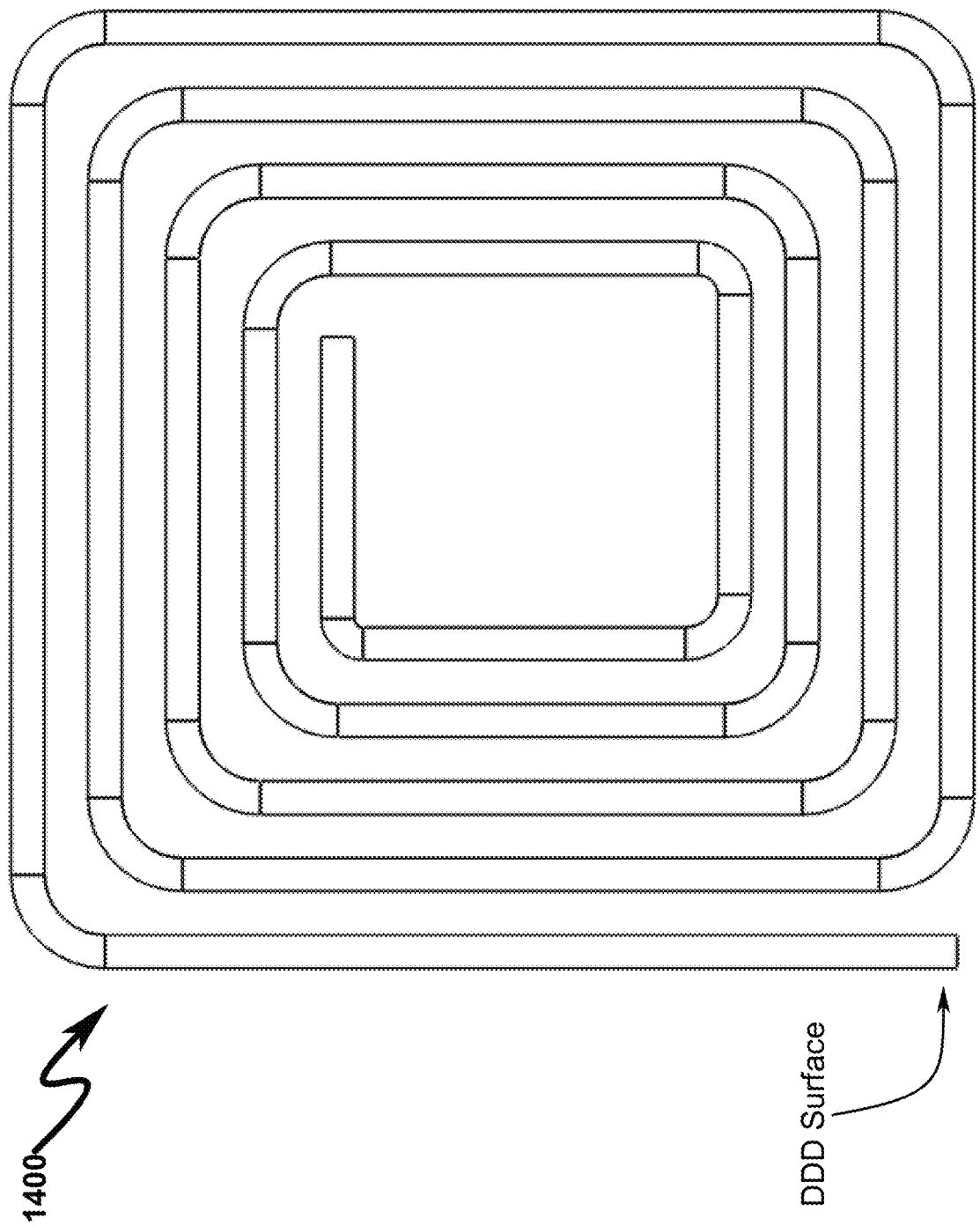
FIG. 14 illustrates a top view of a preferred exemplary rectangular spiral DPP form factor.
Figure 15:
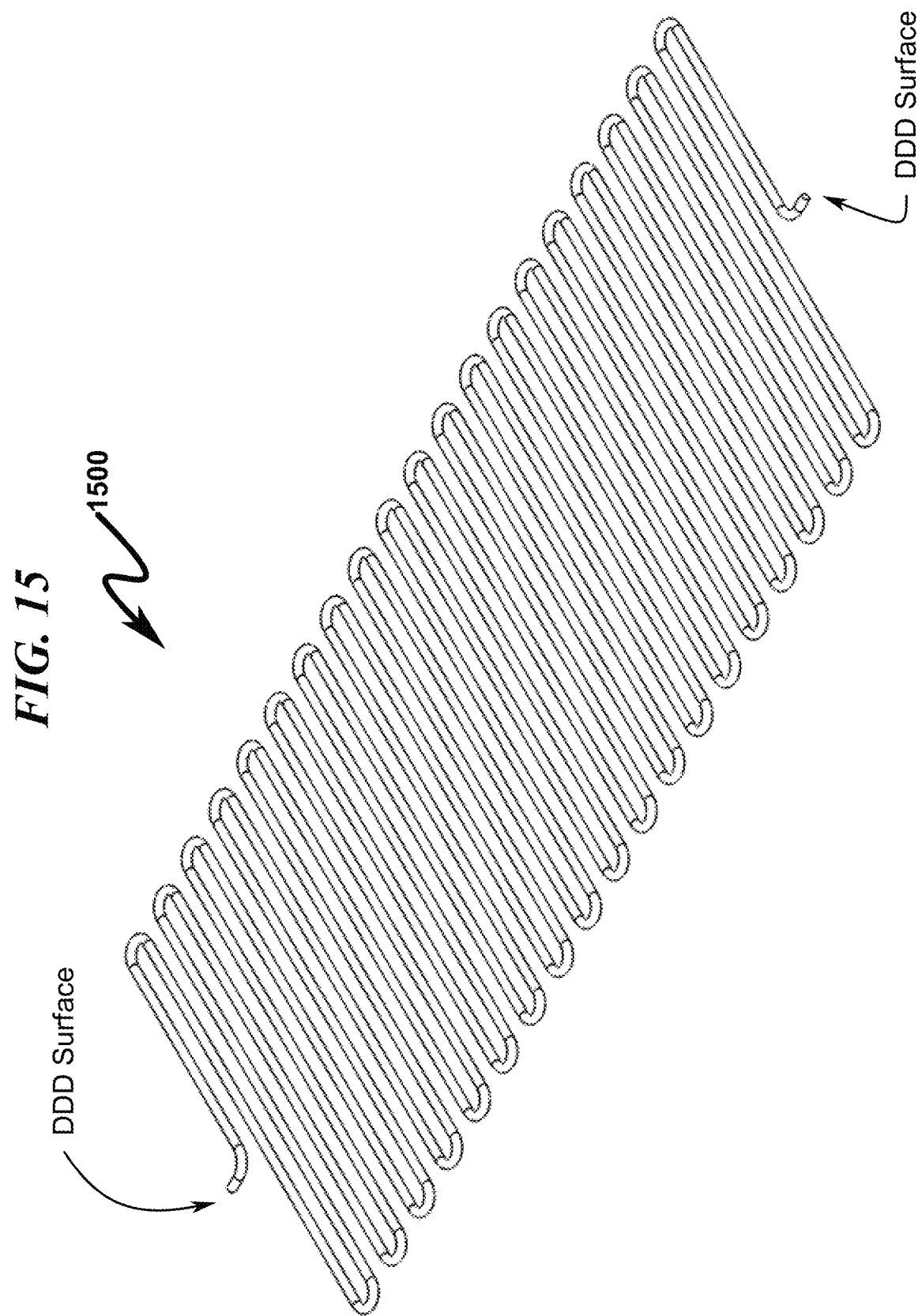
FIG. 15 illustrates a top perspective view of a preferred exemplary serpentine DPP form factor.
Figure 16:
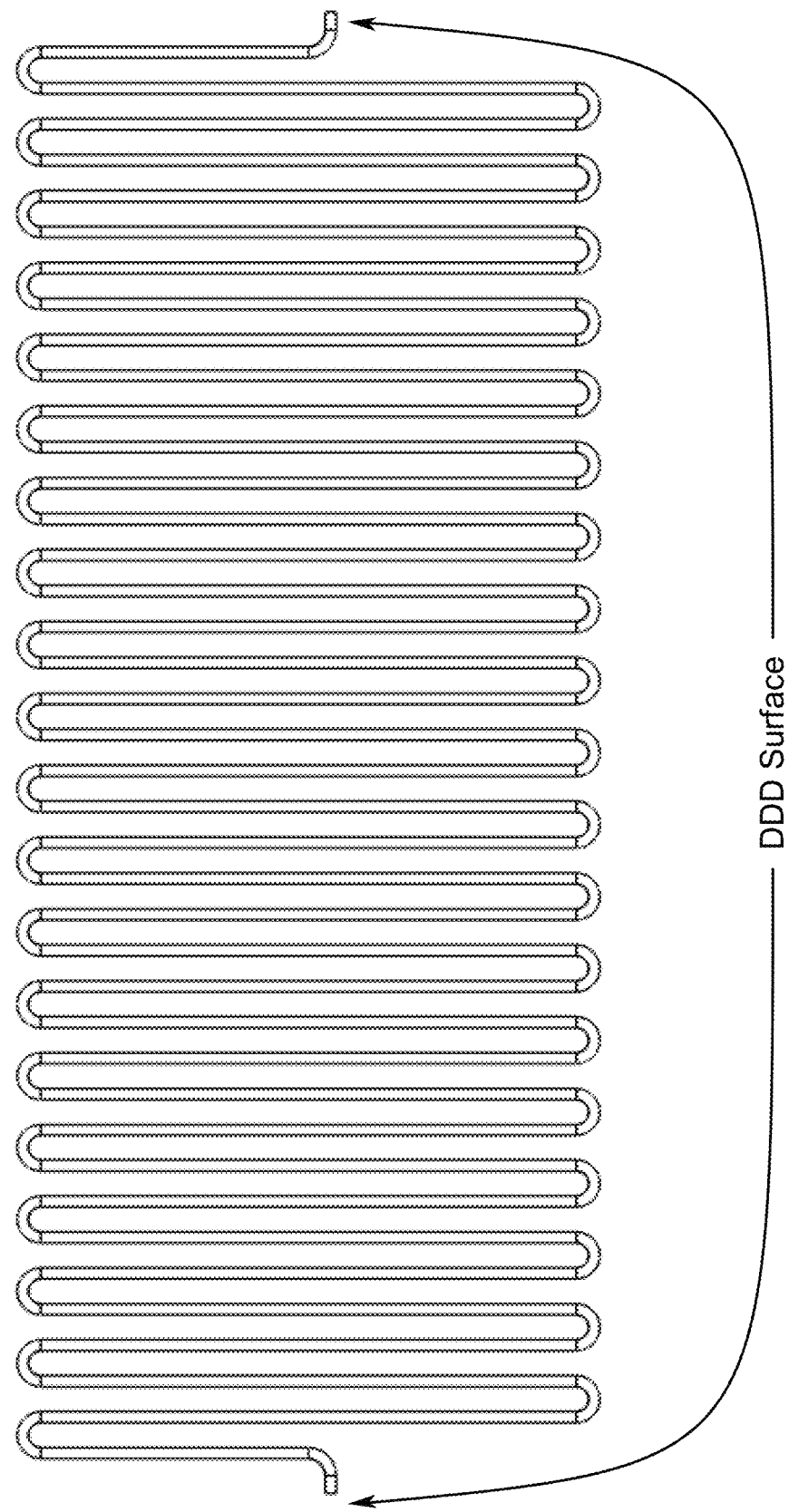
FIG. 16 illustrates a top view of a preferred exemplary serpentine DPP form factor.

FIG. 9 (0900)-FIG. 16 (1600) depict several exemplary drug delivery payload path (DPP) form factors anticipated by the present invention, including helix (FIG. 9 (0900)-FIG. 10 (1000)), spiral (FIG. 11 (1100)-FIG. 12 (1200)), rectangular spiral (FIG. 13 (1300)-FIG. 14 (1400)), and serpentine (FIG. 15 (1500)-FIG. 16 (1600)). A rectangular helix (not shown) may also be configured by combining the teachings of FIG. 9 (0900)-FIG. 10 (1000) with that shown in FIG. 13 (1300)-FIG. 14 (1400). These depicted DPPs represent the pattern pathways produced by the LPG within the DDD. The present invention anticipates that these are only a few of a wide variety of DPP pathways that may be used to internally store and/or deliver the DDP (optionally with connection to a DDR) to the DDT. Furthermore, combinations of these DPPs are anticipated as well as scenarios where layering of DPPs within the DDD. While the depicted DPPs have a circular cross section, the present invention is not limited to this geometry, as the LPG may be configured to generate cross sections of arbitrary perimeter.

One skilled in the art will recognize that these DPP pathways are exemplary of a wide variety of drug payload delivery pathways that may be employed within various physical embodiments of the present invention. With this in mind, the present invention anticipates that combinations of DPP pathways as shown herein and others not specifically disclosed but within the scope of one skilled in the art are applicable to a wide variety of application contexts.

Refillable Drug Delivery Reservoir (DDR) (1700)-(3200)

Figure 17:
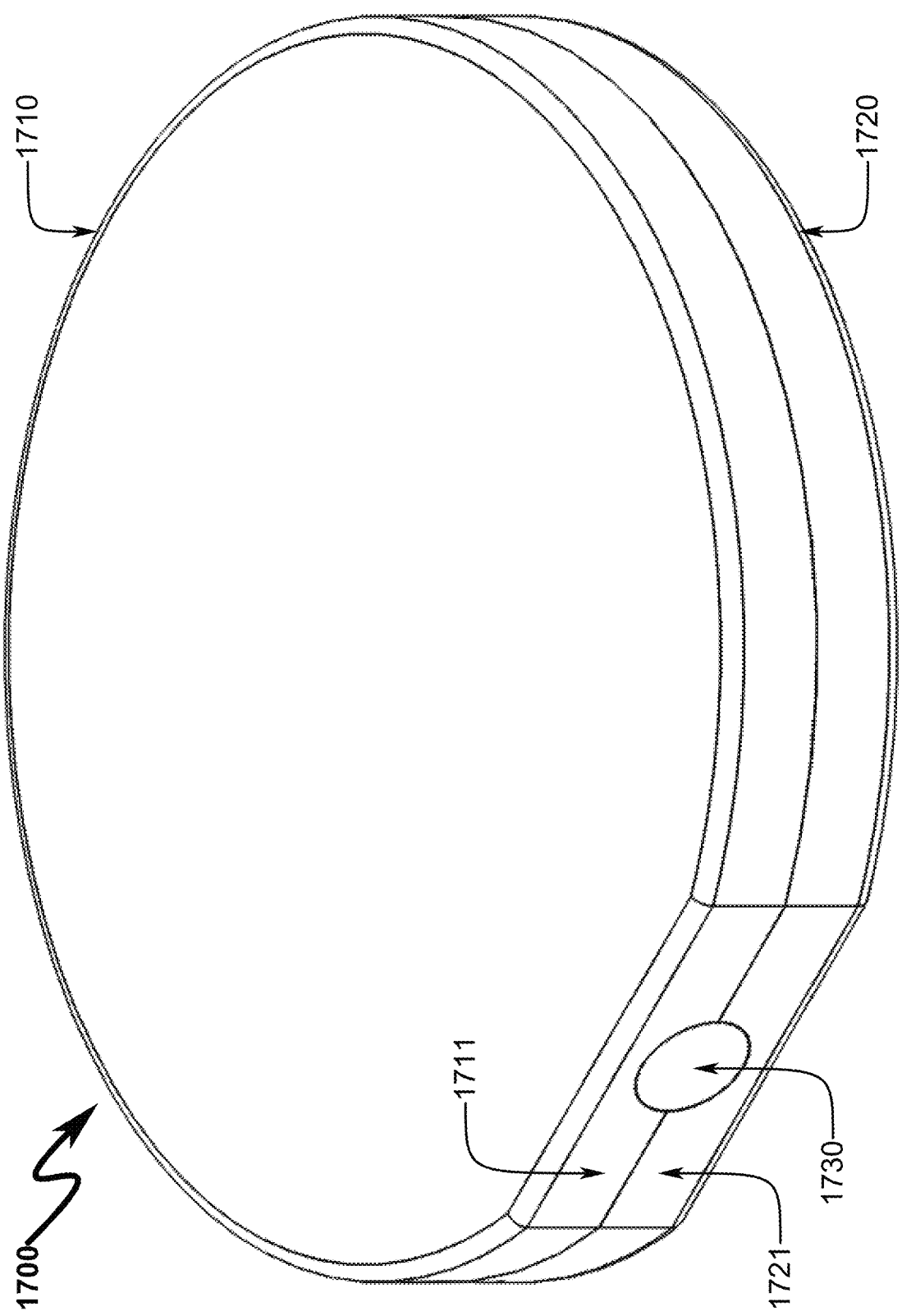
FIG. 17 illustrates a top front right perspective view of a preferred exemplary invention drug delivery device (DDD) button-style embodiment incorporating a refilling port.
Figure 18:
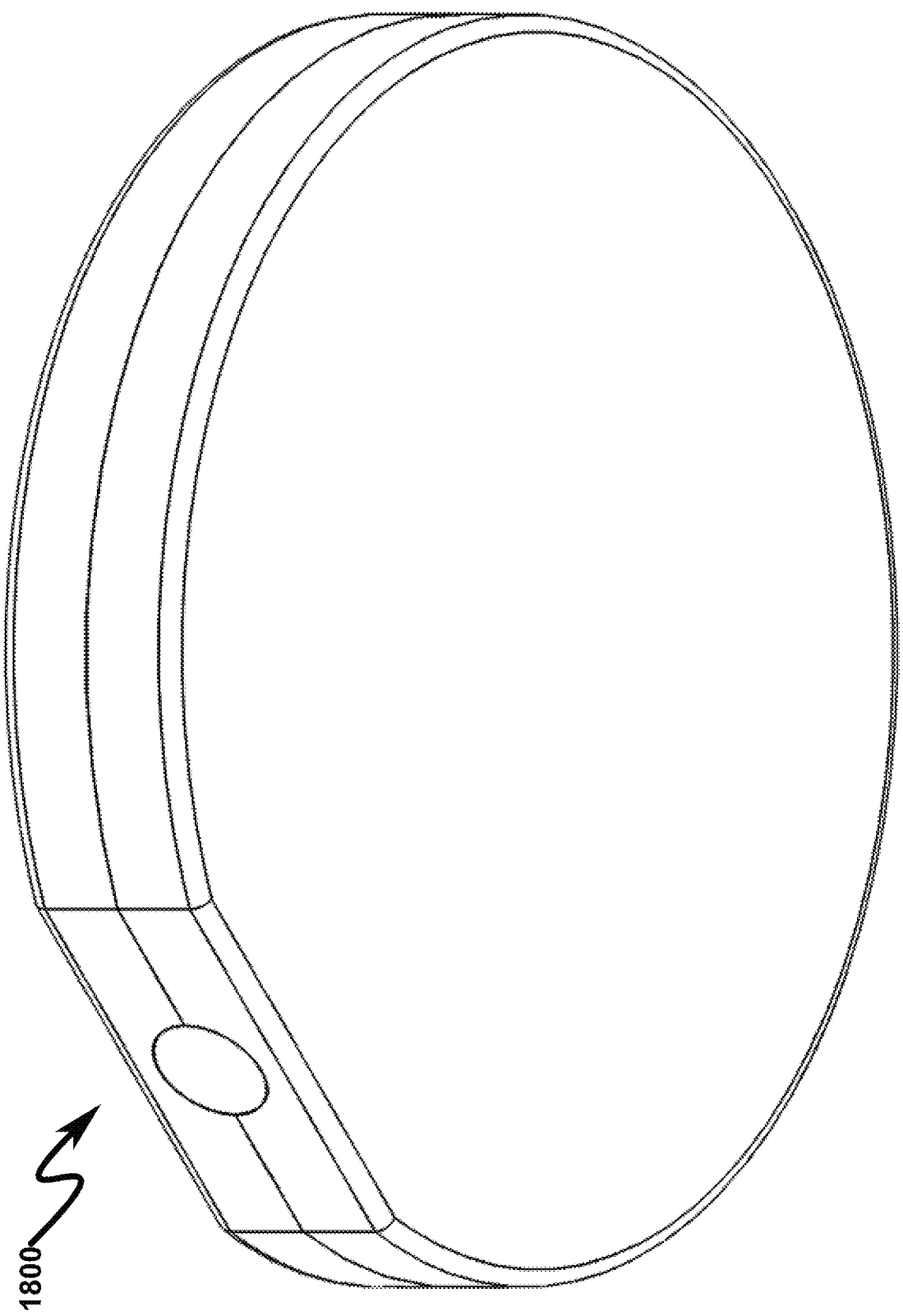
FIG. 18 illustrates a bottom front right perspective view of a preferred exemplary invention drug delivery device (DDD) button-style embodiment incorporating a refilling port.
Figure 19:
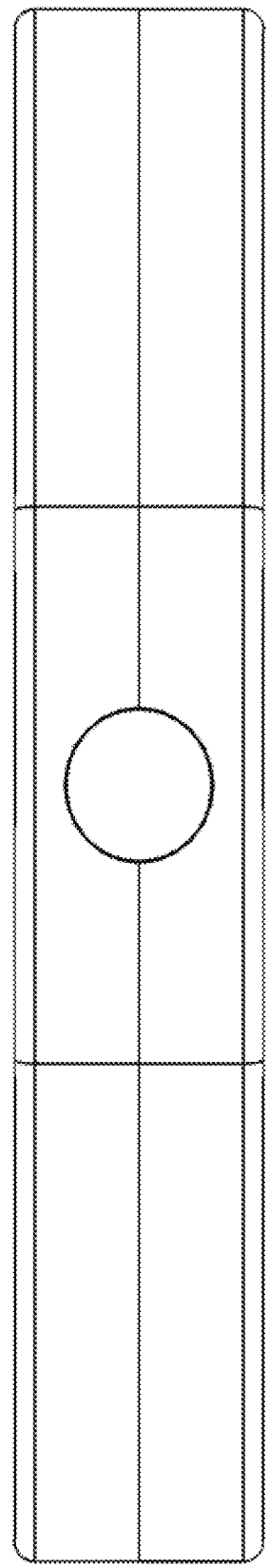
FIG. 19 illustrates a front view of a preferred exemplary invention drug delivery device (DDD) button-style embodiment incorporating a refilling port.
Figure 20:
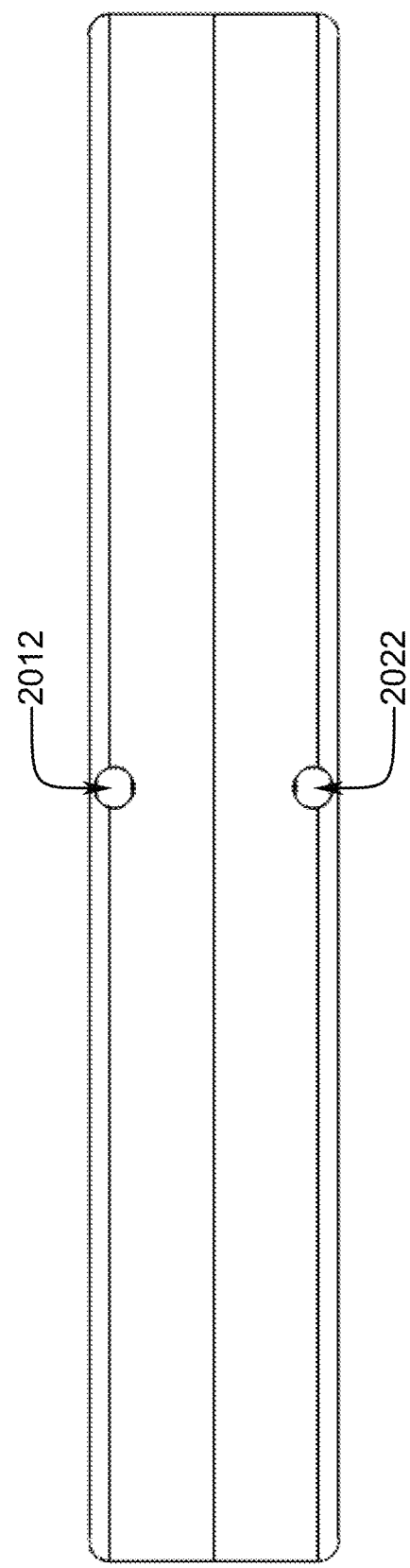
FIG. 20 illustrates a rear view of a preferred exemplary invention drug delivery device (DDD) button-style embodiment incorporating a refilling port.
Figure 21:
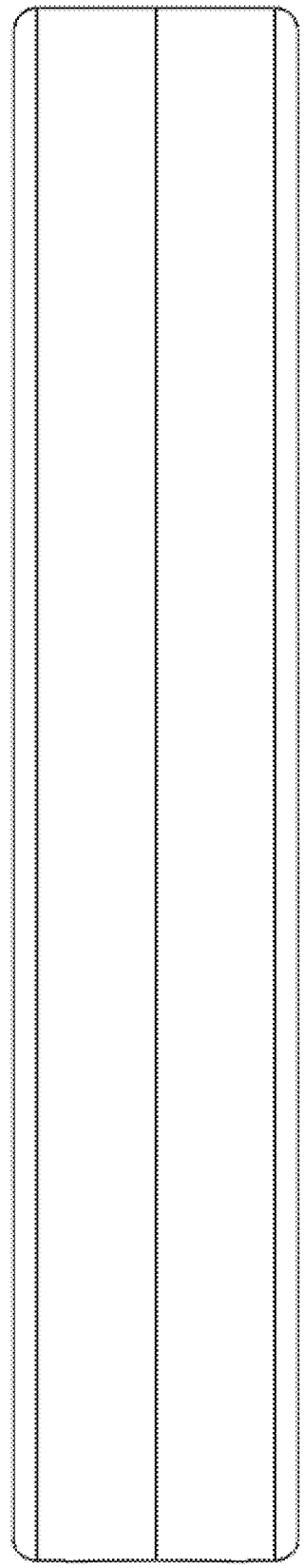
FIG. 21 illustrates a left side view of a preferred exemplary invention drug delivery device (DDD) button-style embodiment incorporating a refilling port.
Figure 22:
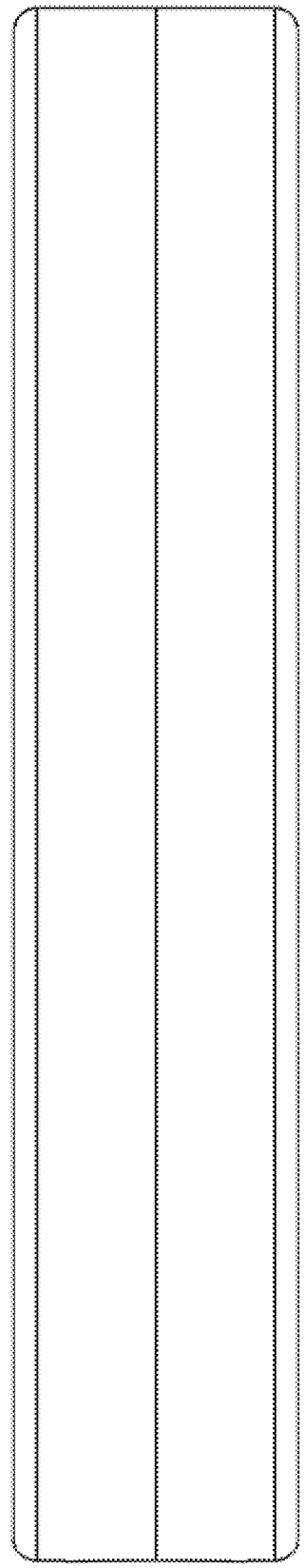
FIG. 22 illustrates a right side view of a preferred exemplary invention drug delivery device (DDD) button-style embodiment incorporating a refilling port.
Figure 23:
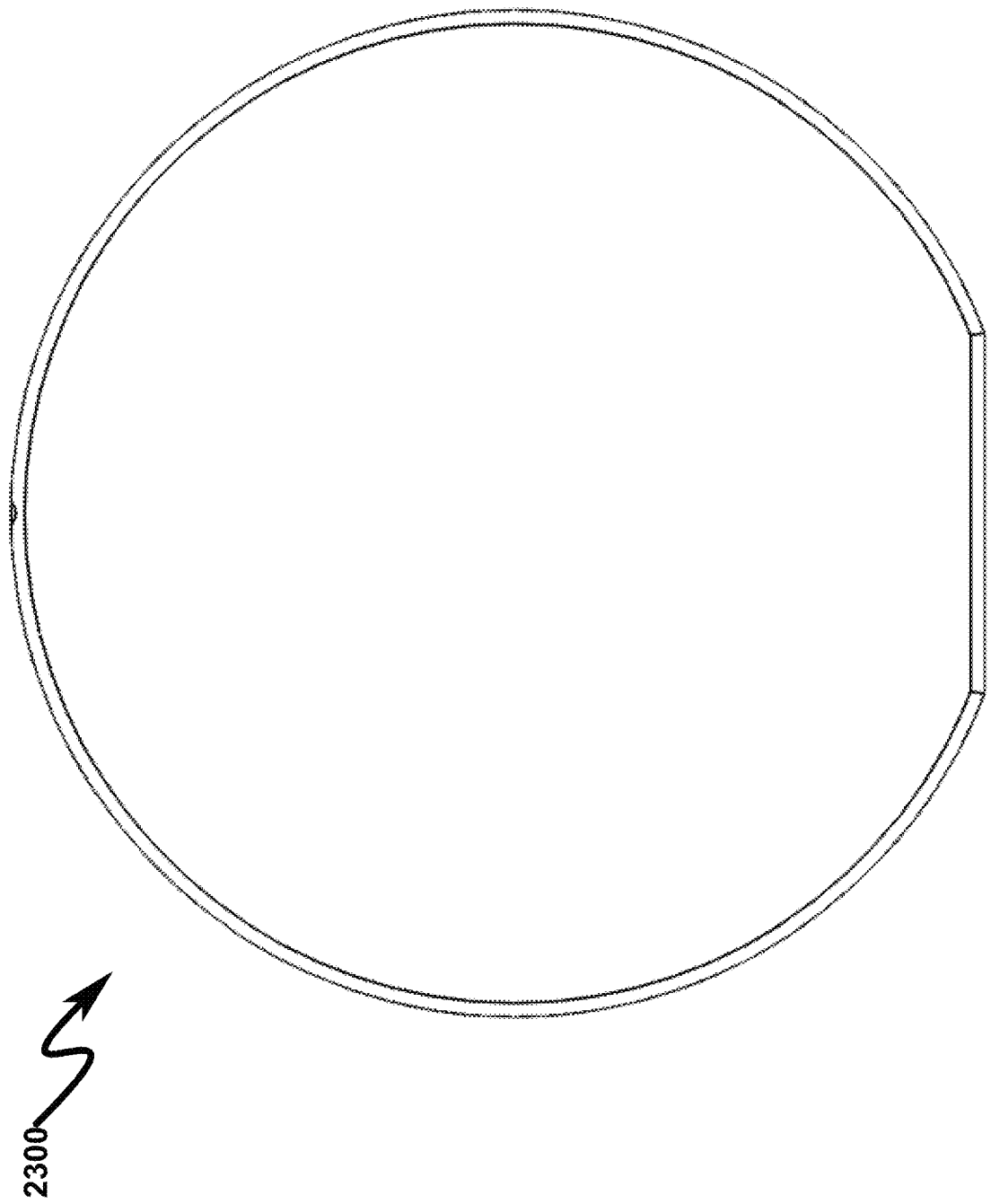
FIG. 23 illustrates a top view of a preferred exemplary invention drug delivery device (DDD) button-style embodiment incorporating a refilling port.
Figure 24:
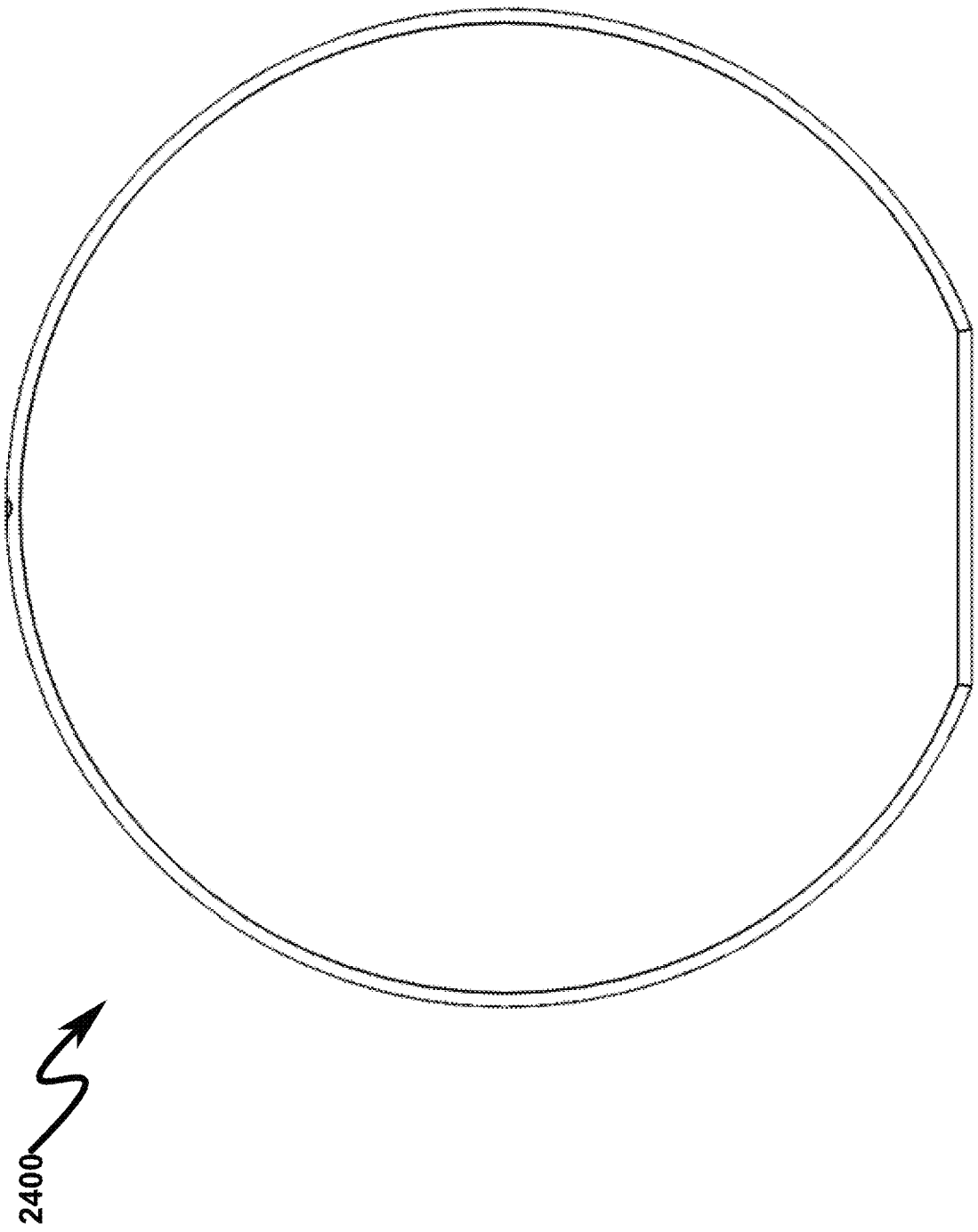
FIG. 24 illustrates a bottom view of a preferred exemplary invention drug delivery device (DDD) button-style embodiment incorporating a refilling port.

In some circumstances the present invention may incorporate a drug delivery reservoir (DDR) that may be refillable in some embodiments. FIG. 17 (1700)-FIG. 32 (3200) depict a preferred exemplary embodiment of this concept as applied to a button DDD form factor. In this exemplary embodiment the DDD is formed with a top half (1710) and a bottom half (1720) mated together with each half having a corresponding index face (1711, 1721) that identifies the location of a drug delivery reservoir port (DRP) (1730) that may be used to fill/refill the DDD. DDP pathways are generated internal to the DDD with provisions for one or more external delivery ports (EDP) (2012, 2022) provided for as generally depicted in FIG. 20 (2000).

Figure 25:
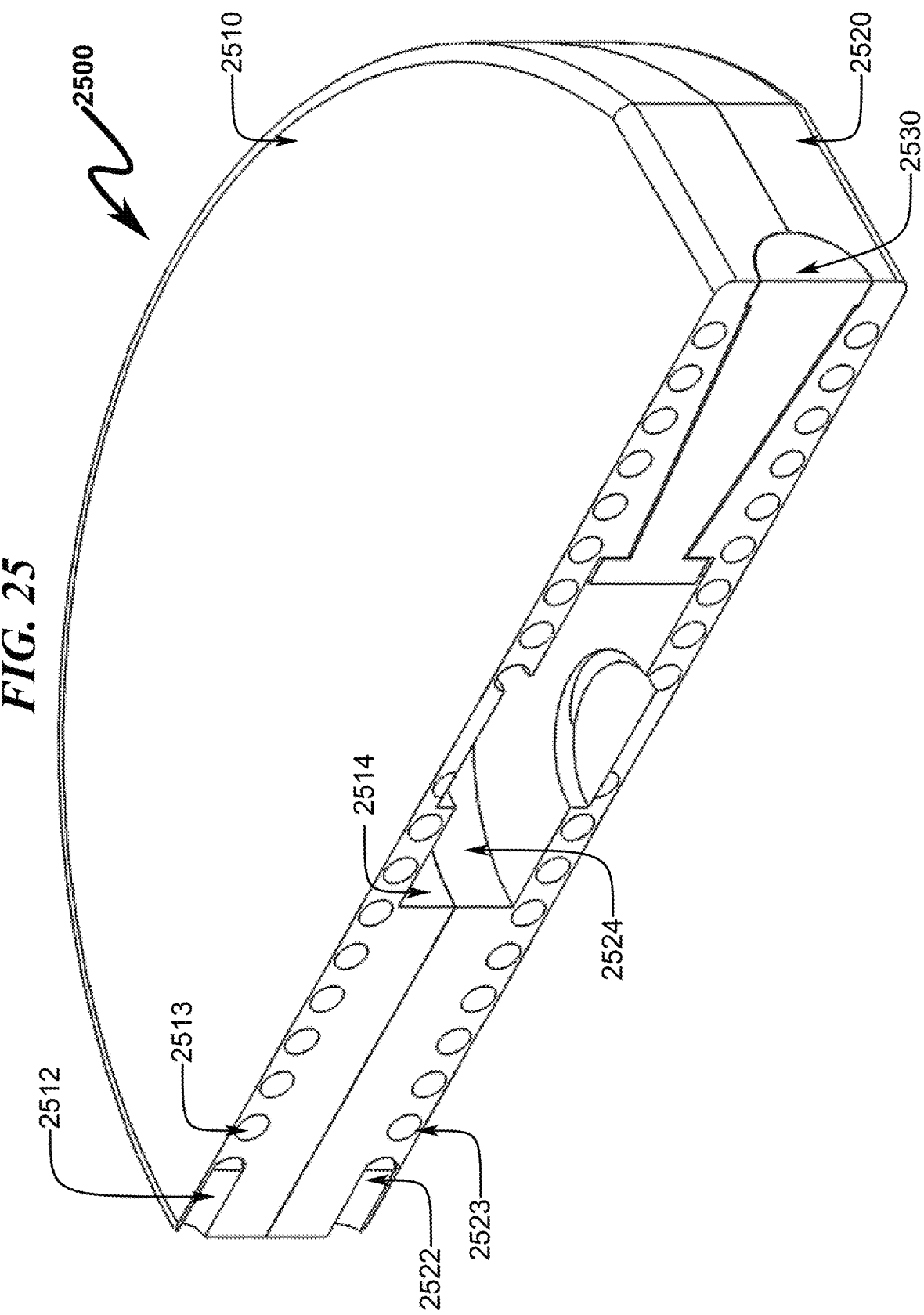
FIG. 25 illustrates a side perspective section view of a preferred exemplary invention drug delivery device (DDD) button-style embodiment incorporating a refilling port.
Figure 26:
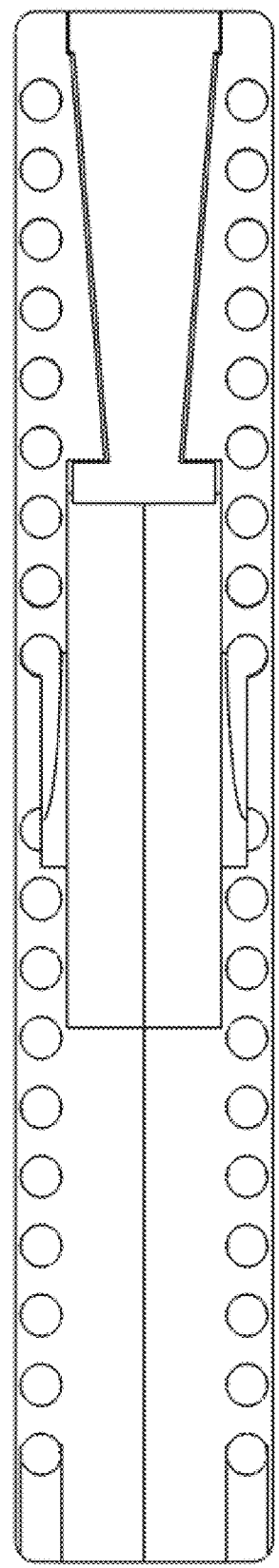
FIG. 26 illustrates a side section view of a preferred exemplary invention drug delivery device (DDD) button-style embodiment incorporating a refilling port.
Figure 27:
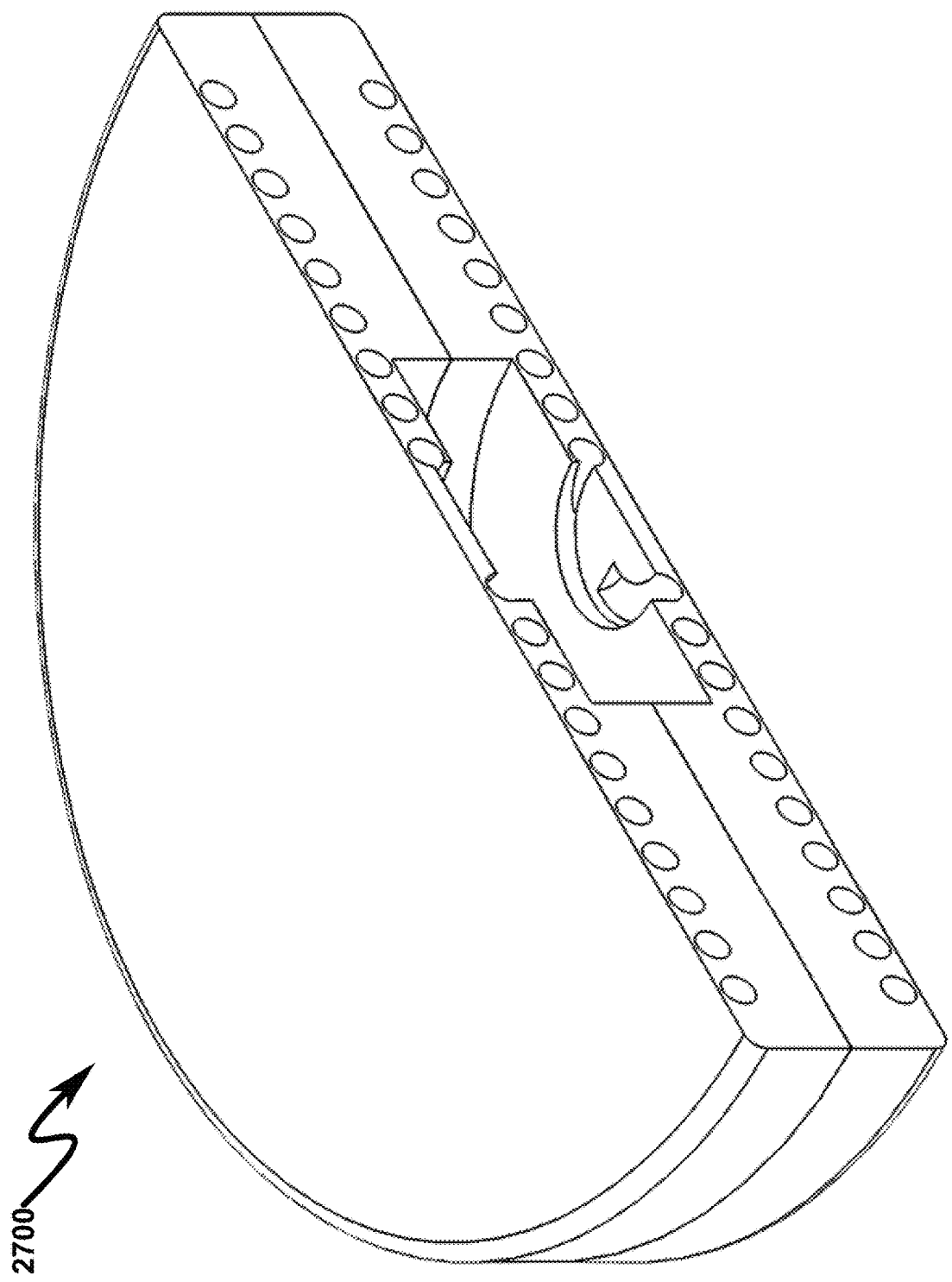
FIG. 27 illustrates a front perspective section view of a preferred exemplary invention drug delivery device (DDD) button-style embodiment incorporating a refilling port.
Figure 28:
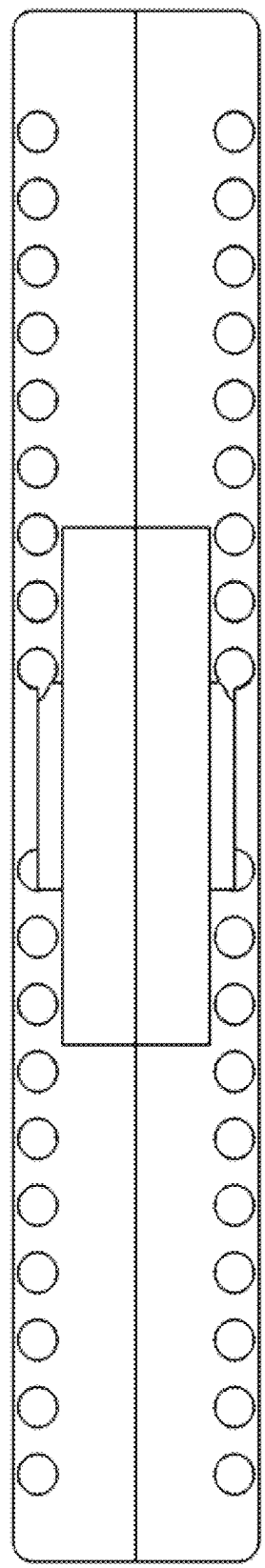
FIG. 28 illustrates a front section view of a preferred exemplary invention drug delivery device (DDD) button-style embodiment incorporating a refilling port.
Figure 29:
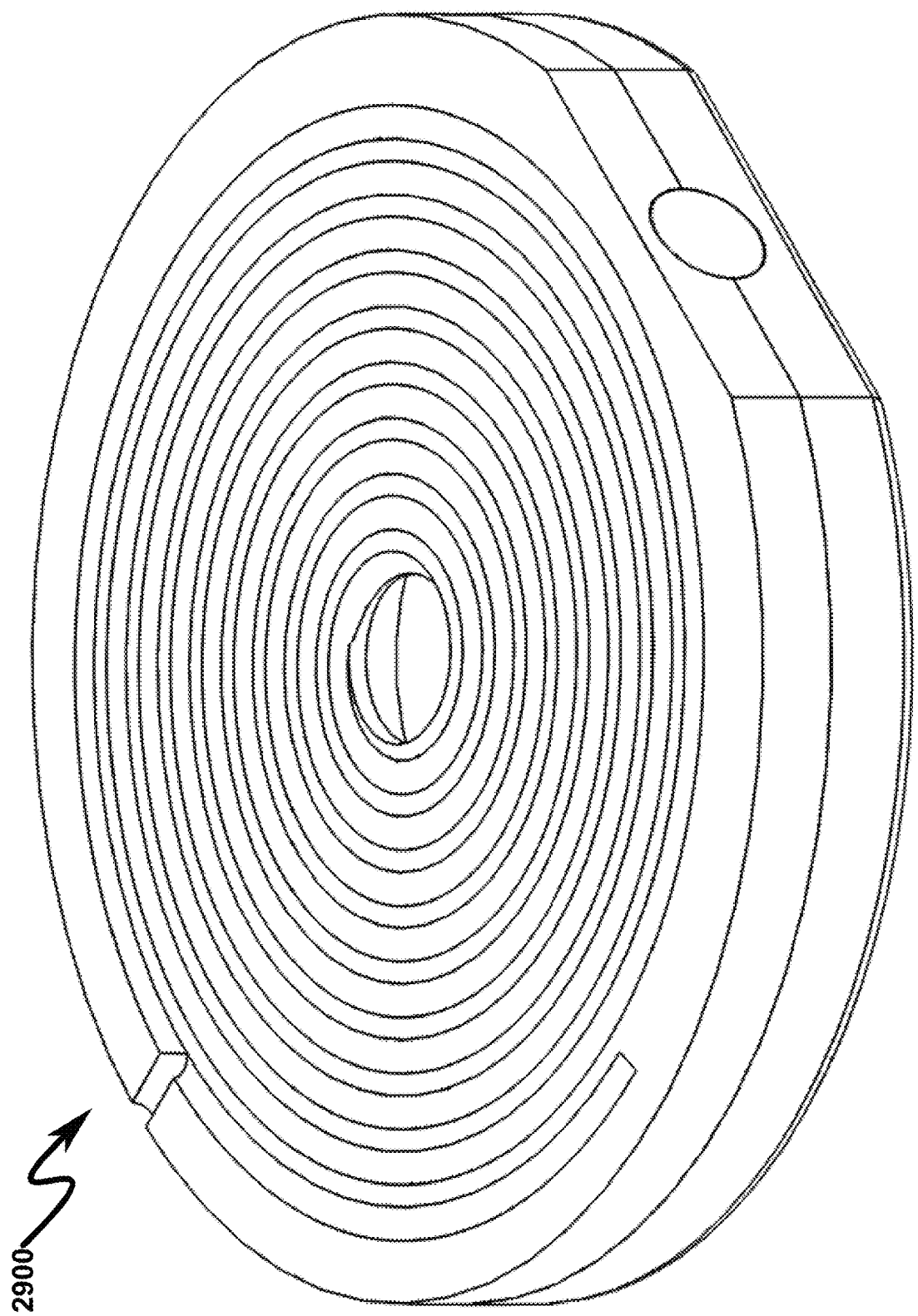
FIG. 29 illustrates a top upper perspective section view of a preferred exemplary invention drug delivery device (DDD) button-style embodiment incorporating a refilling port and detailing an exemplary top-half spiral drug delivery path (DDP)
Figure 30:
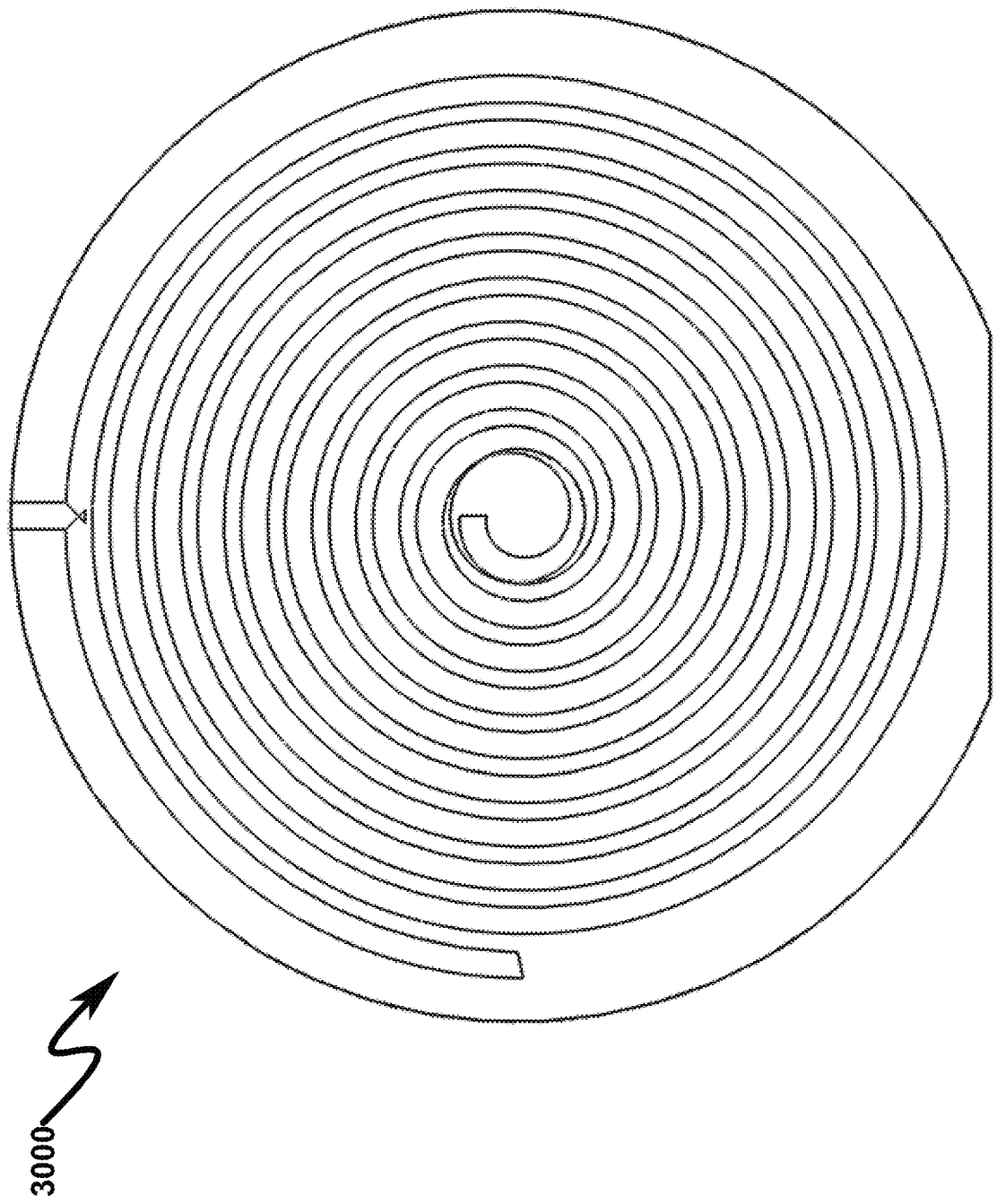
FIG. 30 illustrates a top upper section view of a preferred exemplary invention drug delivery device (DDD) button-style embodiment incorporating a refilling port and detailing an exemplary top-half spiral drug delivery path (DDP)
Figure 31:
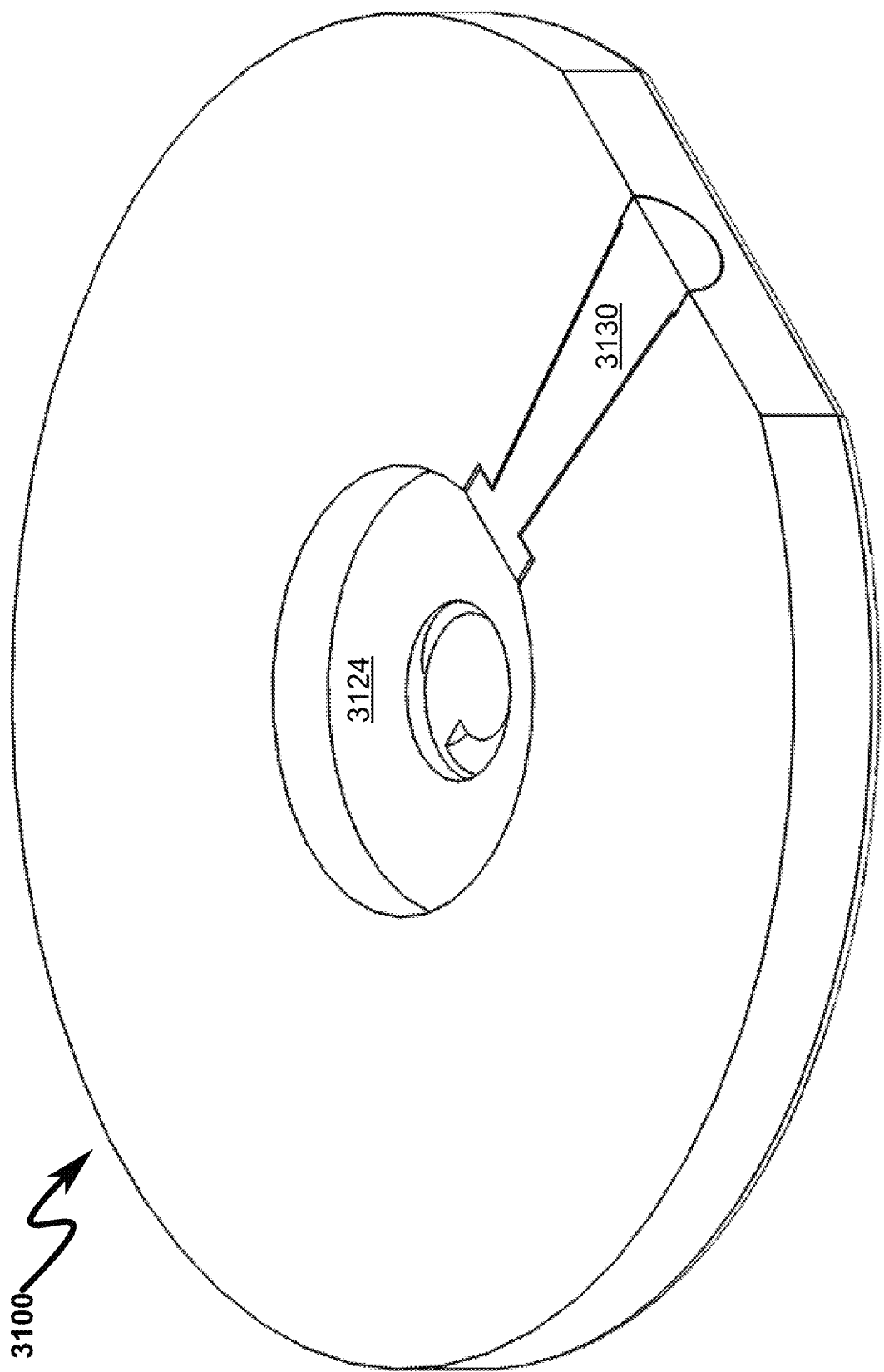
FIG. 31 illustrates a top mid-plane perspective section view of a preferred exemplary invention drug delivery device (DDD) button-style embodiment incorporating a refilling port and detailing an exemplary drug delivery reservoir (DDR)
Figure 32:
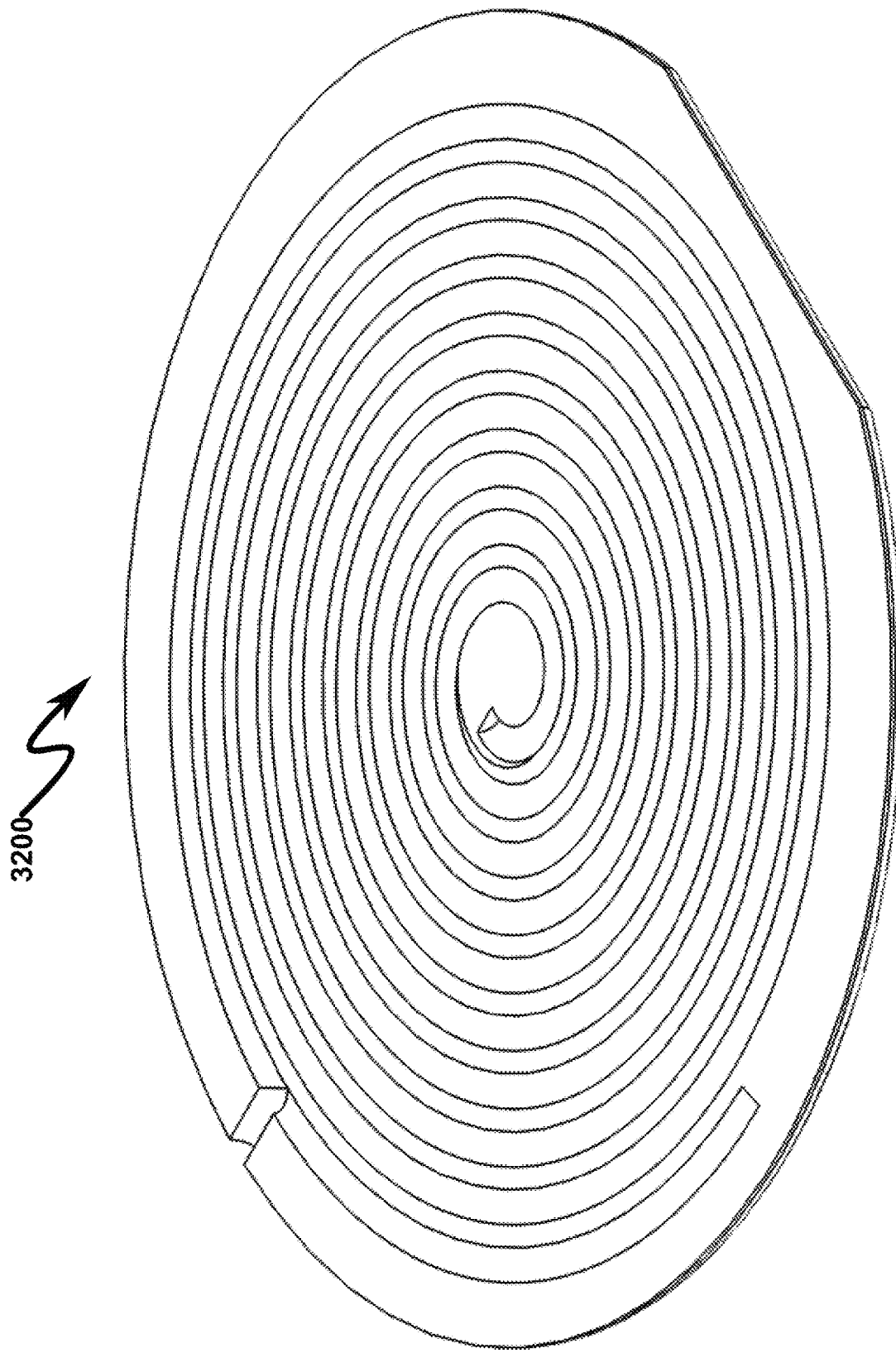
FIG. 32 illustrates a top lower perspective section view of a preferred exemplary invention drug delivery device (DDD) button-style embodiment incorporating a refilling port and detailing an exemplary bottom-half spiral drug delivery path (DDP)

The internal construction of this button-style DDD is generally depicted in FIG. 25 (2500)-FIG. 32 (3200) by the various section views. Here the DPP have been generally depicted using extruded cuts within the DDD to show the internal drug delivery pathways provided for by the LPG process. Referencing FIG. 25 (2500), the external delivery ports (EDP) (2512, 2522) are depicted that are connected to upper (2513) and lower (2523) DPP that source DDP from a DDR created by an upper (2514) and lower (2524) interior void within the DDD. This DDR may be filled during assembly of the upper (2510) and lower (2520) half components of the DDD or in some circumstances loaded via syringe injection via a rubberized DRP (2530). The DRP may also be constructed such that the DDD DDR is loaded via the DRP port that contains the DRP and then this DDR port may be externally plugged to seal in the DDP within the DDR. The top mid-plane perspective section view of FIG. 31 (3100) provides additional detail regarding the relationship between the DDR (3124) and the DRP (3130). FIG. 29 (2900)-FIG. 30 (3000) provide additional detail regarding an exemplary upper section DPP and FIG. 32 (3200) provides additional detail regarding an exemplary lower section DPP.

Exemplary DDD Refilling Protocol (3300)-(4000)

Figure 33:
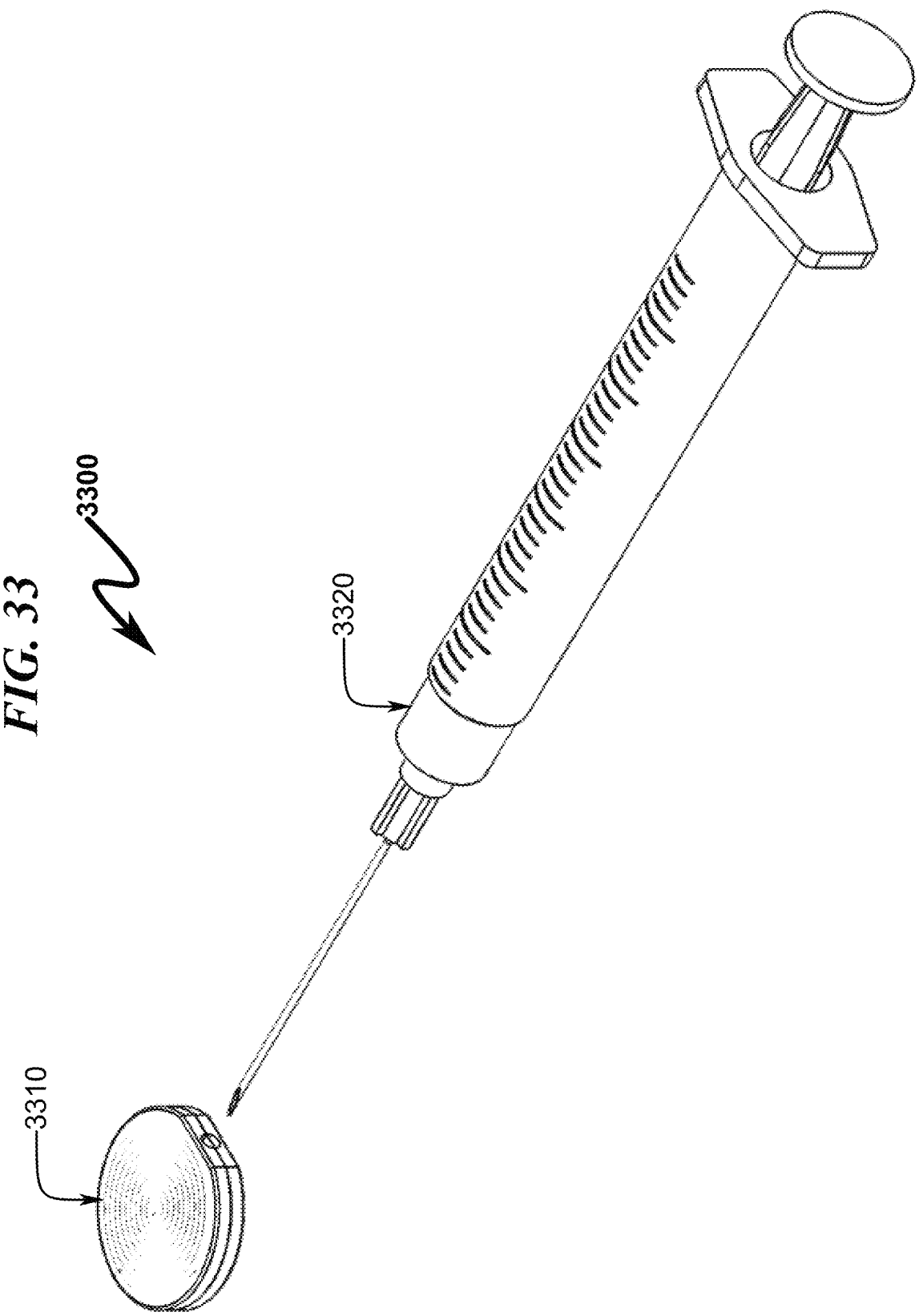
FIG. 33 illustrates a top perspective view of a preferred exemplary invention drug delivery device (DDD) button-style embodiment positioned for loading of the DDR via a needle syringe.
Figure 34:
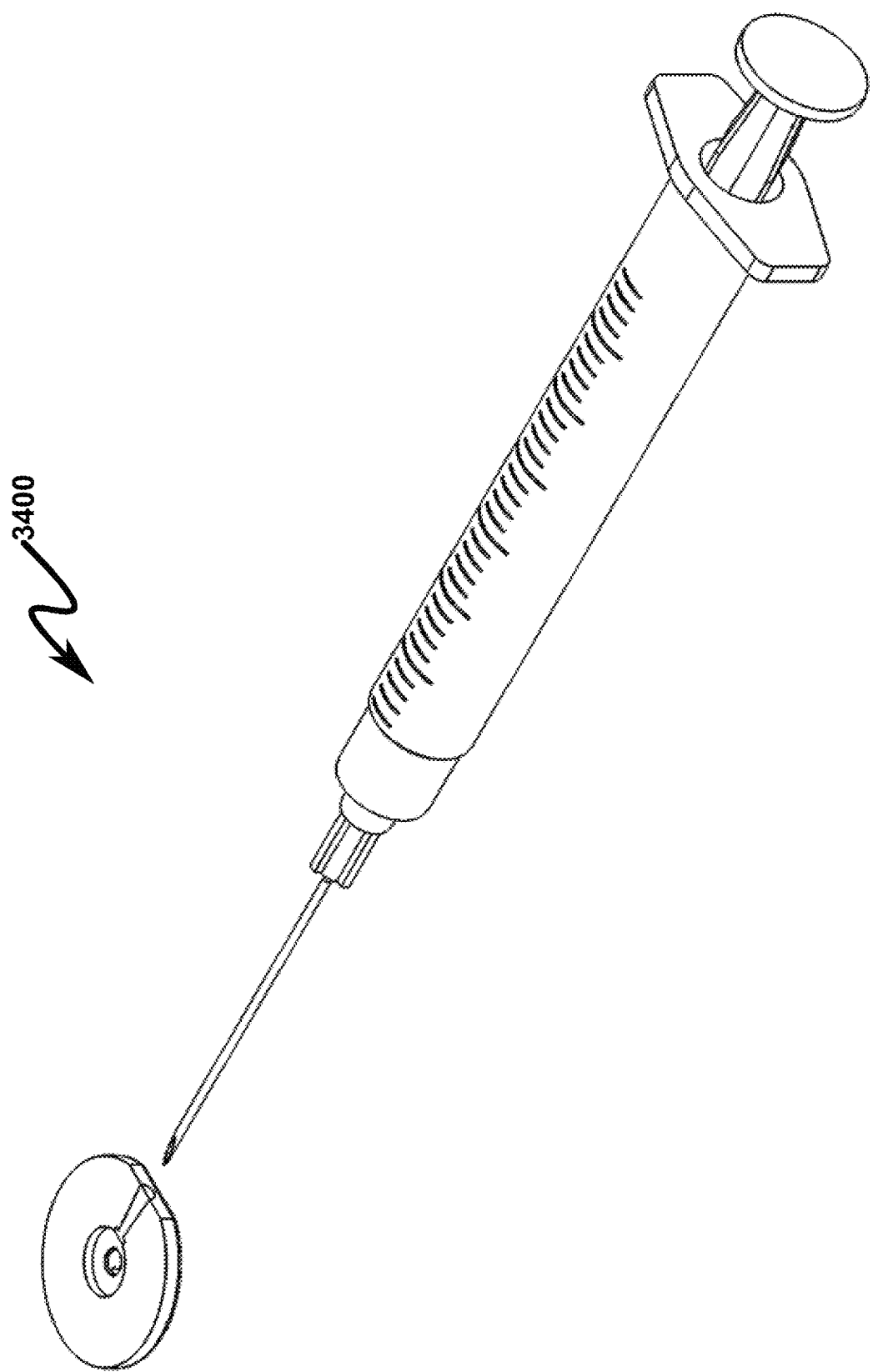
FIG. 34 illustrates a top perspective section view of a preferred exemplary invention drug delivery device (DDD) button-style embodiment positioned for loading of the DDR via a needle syringe.
Figure 35:
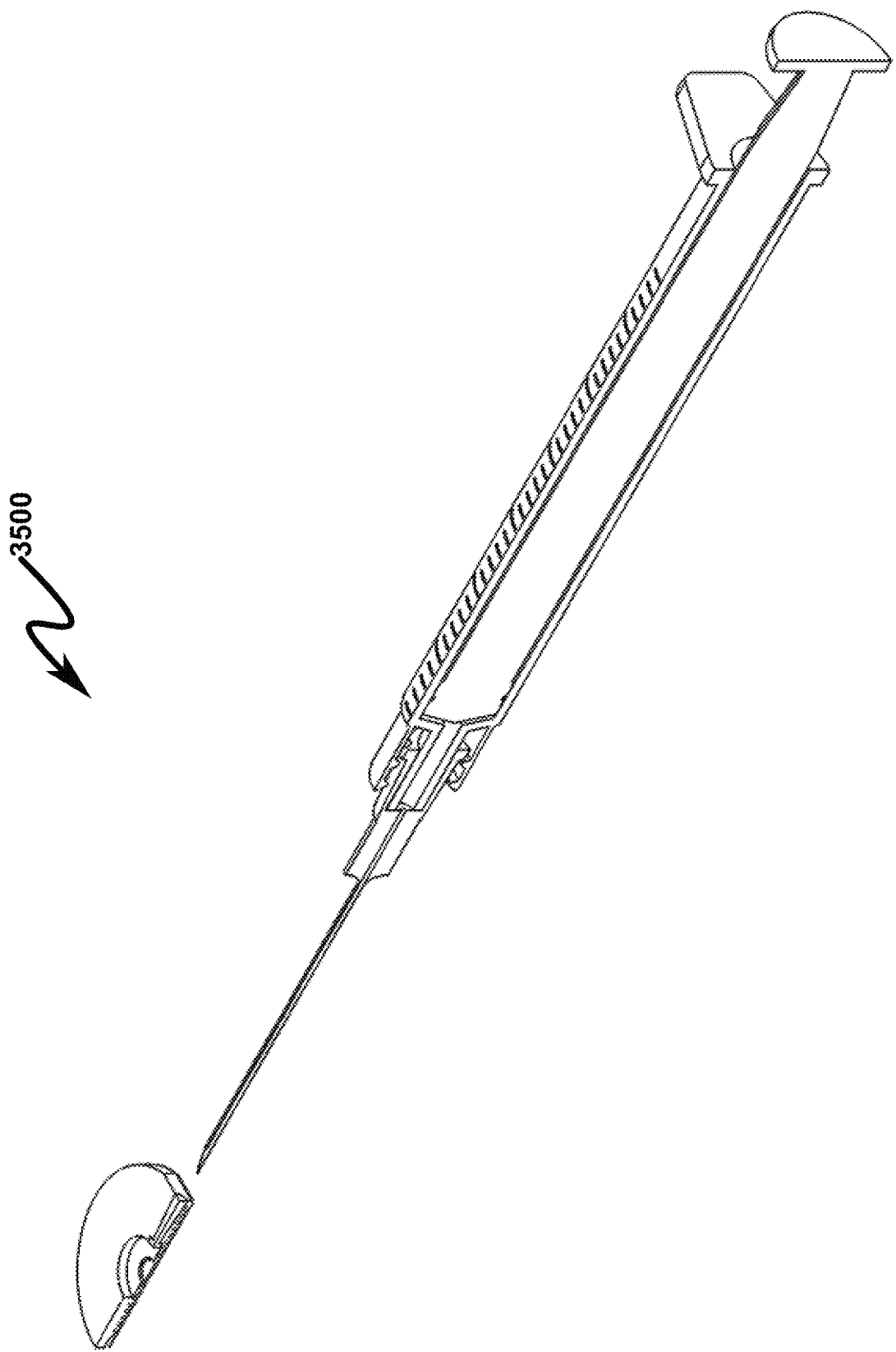
FIG. 35 illustrates a top and front perspective section views of a preferred exemplary invention drug delivery device (DDD) button-style embodiment positioned for loading of the DDR via a needle syringe.
Figure 36:
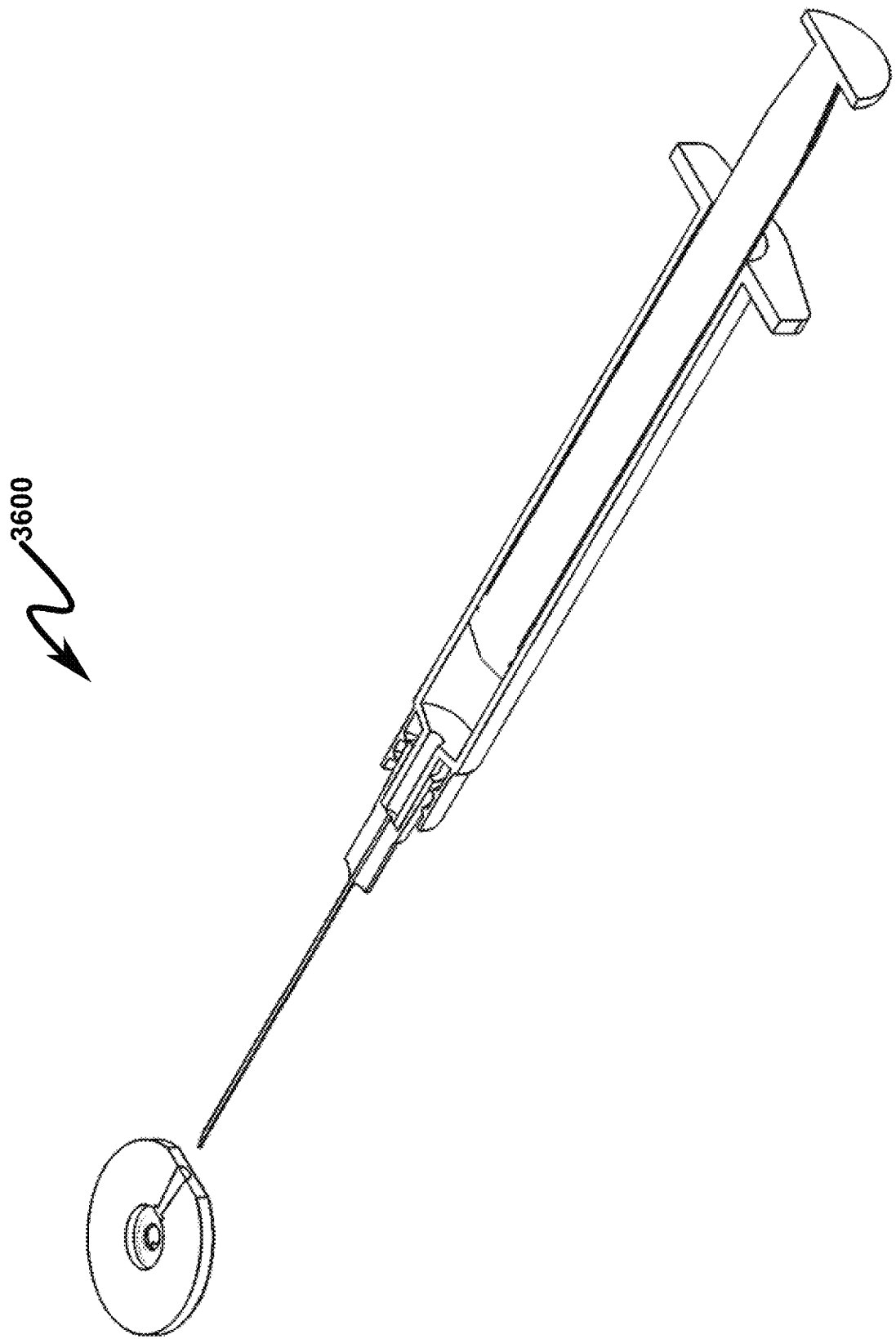
FIG. 36 illustrates top perspective section views of a preferred exemplary invention drug delivery device (DDD) button-style embodiment positioned for loading of the DDR via a prefilled needle syringe.
Figure 37:
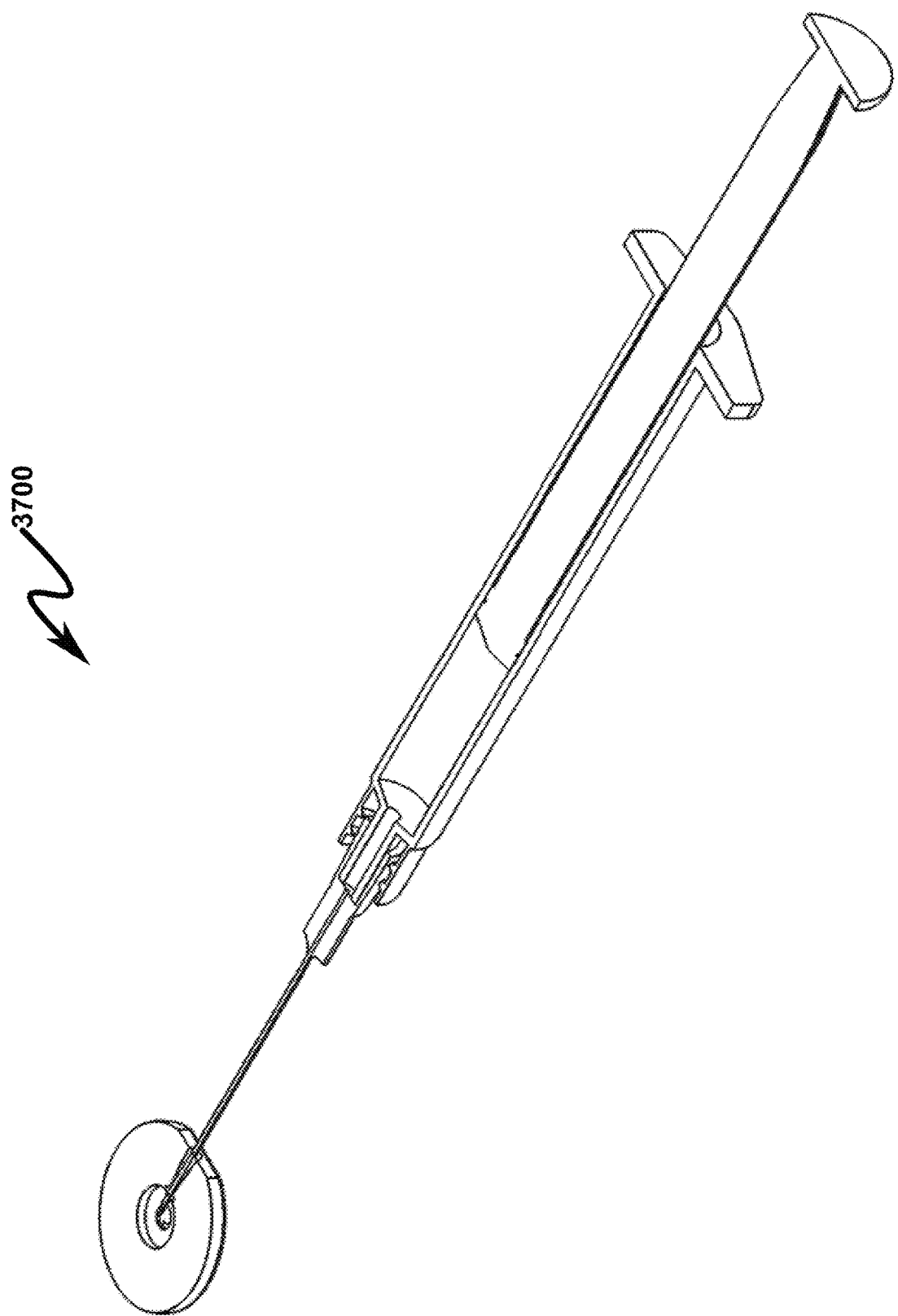
FIG. 37 illustrates top perspective section views of a preferred exemplary invention drug delivery device (DDD) button-style embodiment and a needle syringe inserted into the external delivery port (EDP) of the DDD.
Figure 38:
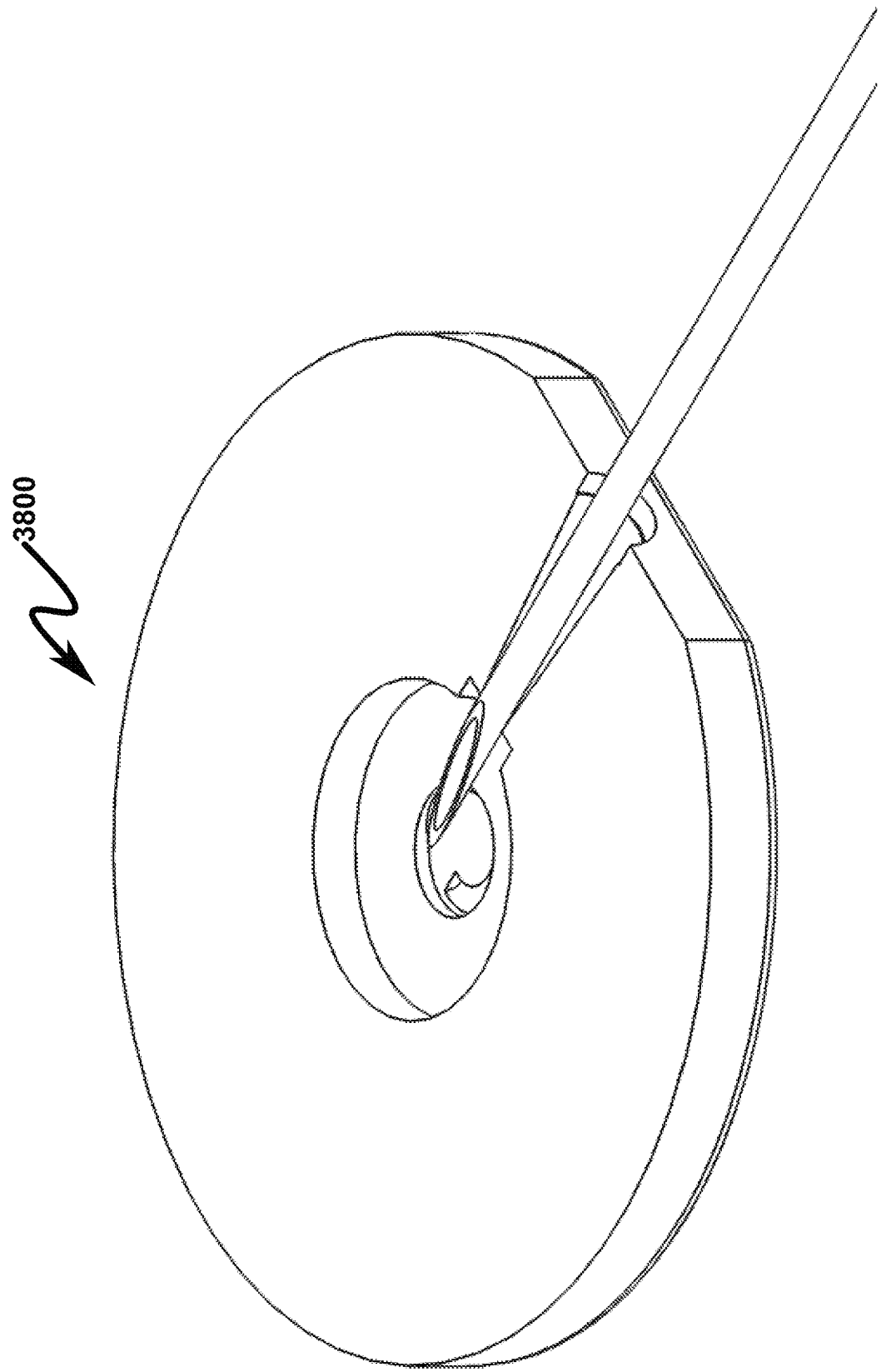
FIG. 38 illustrates a detail top perspective section view of a preferred exemplary invention drug delivery device (DDD) button-style embodiment and a needle syringe inserted into the external delivery port (EDP) of the DDD.
Figure 39:
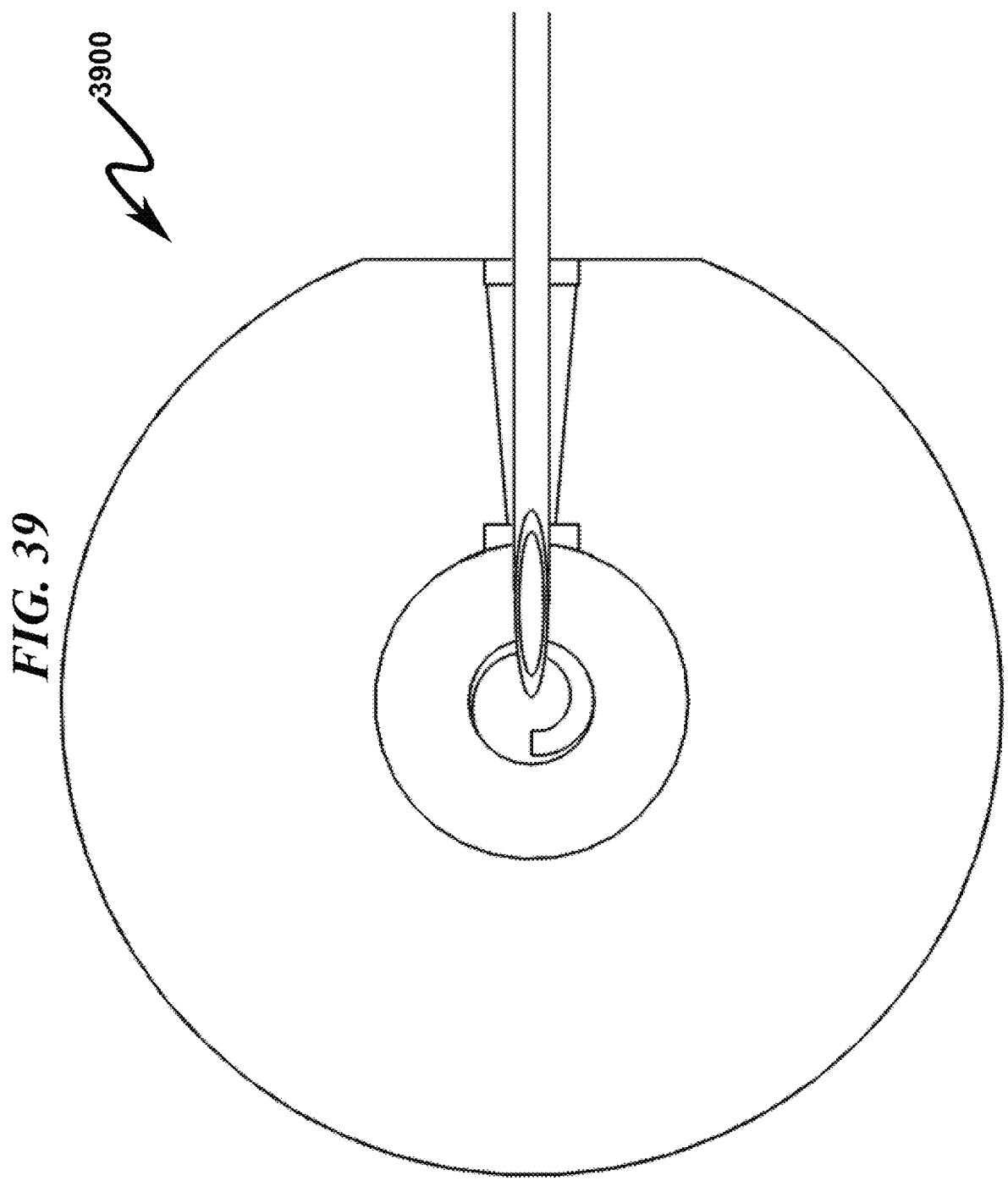
FIG. 39 illustrates a detail top section view of a preferred exemplary invention drug delivery device (DDD) button-style embodiment and a needle syringe inserted into the external delivery port (EDP) of the DDD.
Figure 40:
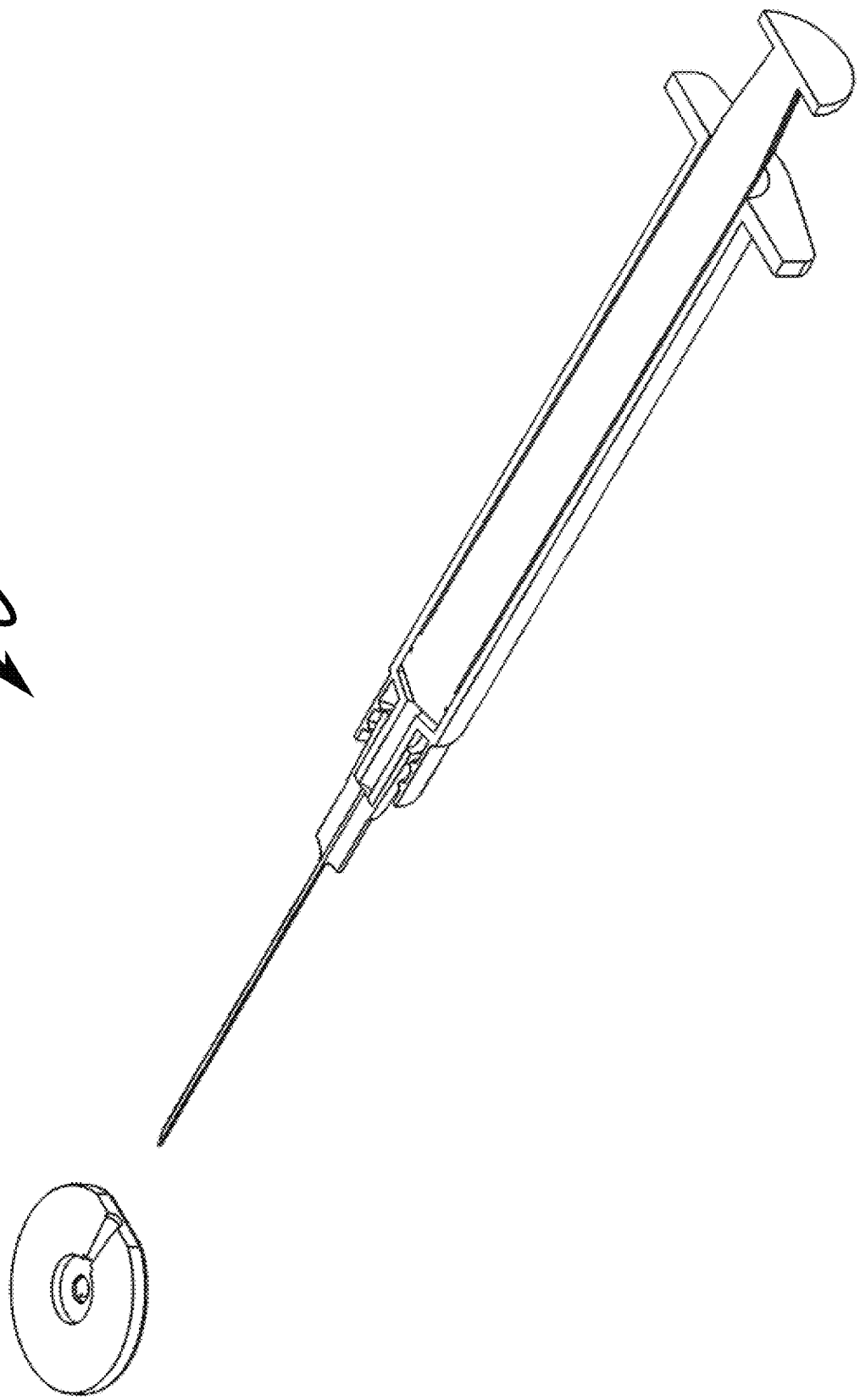
FIG. 40 illustrates top perspective section views of a preferred exemplary invention drug delivery device (DDD) button-style embodiment and a needle syringe after removal from the external delivery port (EDP) of the DDD.

An exemplary DDD refilling protocol is generally depicted in FIG. 33 (3300)-FIG. 40 (4000) in which an exemplary DDD (3310) is refilled using a needle syringe (3320). FIG. 33 (3300)-FIG. 35 (3500) illustrates the pre-injection state in various perspective and section views. FIG. 36 (3600) illustrates a loaded needle syringe ready for DDD refilling. FIG. 37 (3700)-FIG. 39 (3900) illustrates a needle syringe loading the DDR of the DDD via the external delivery port (EDP) of the DDD. FIG. 40 (4000) illustrates an unloaded needle syringe after DDD refilling. This protocol may be equally applied in situations where the EDP is permanently sealed after filling of the DDR by the needle syringe.

Exemplary Multi-Pathway DPP (4100)-(5600)

Figure 41:
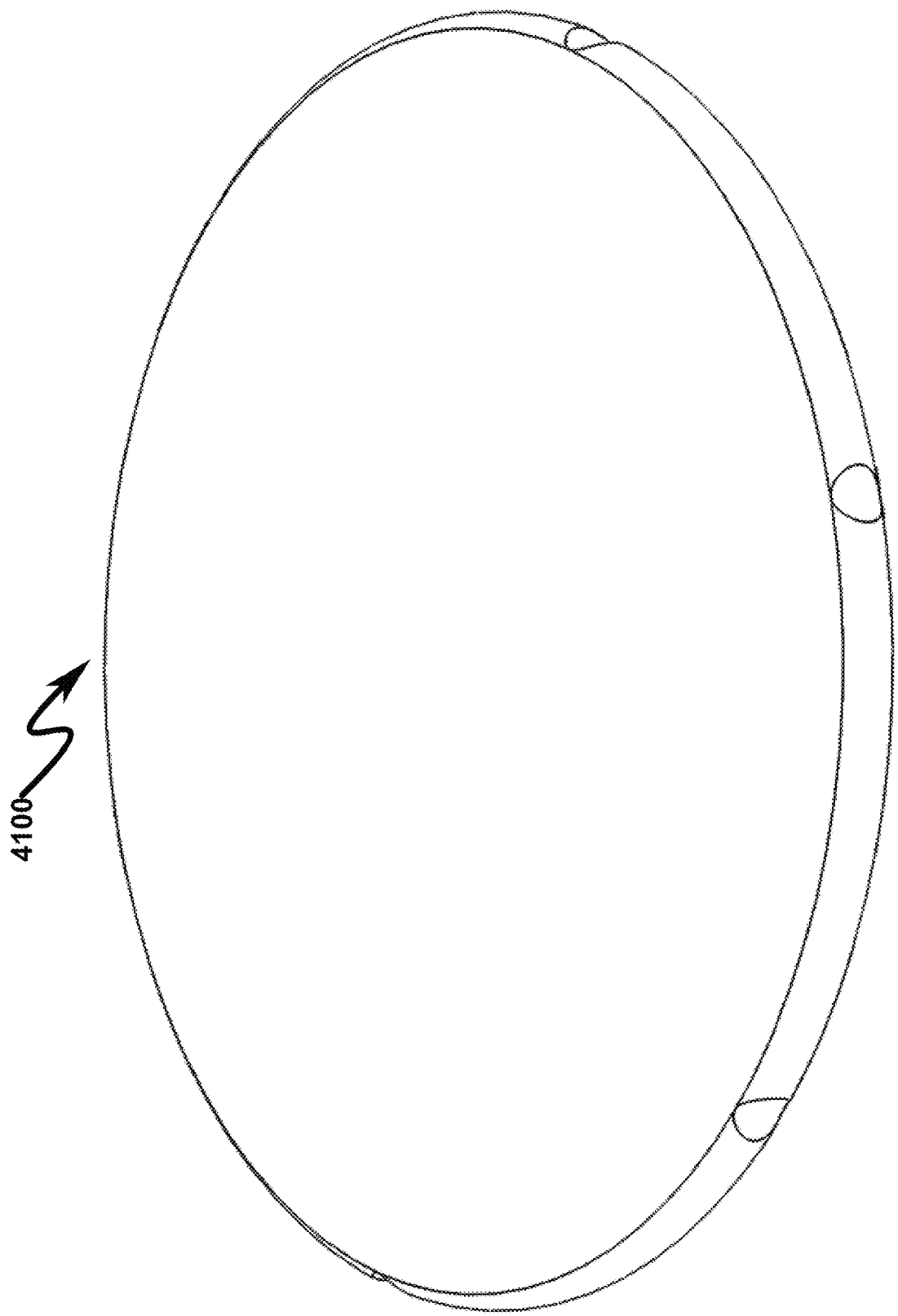
FIG. 41 illustrates a top front right perspective view of a preferred exemplary invention drug delivery device (DDD) disc-style embodiment incorporating multiple radial DPP pathways.
Figure 42:
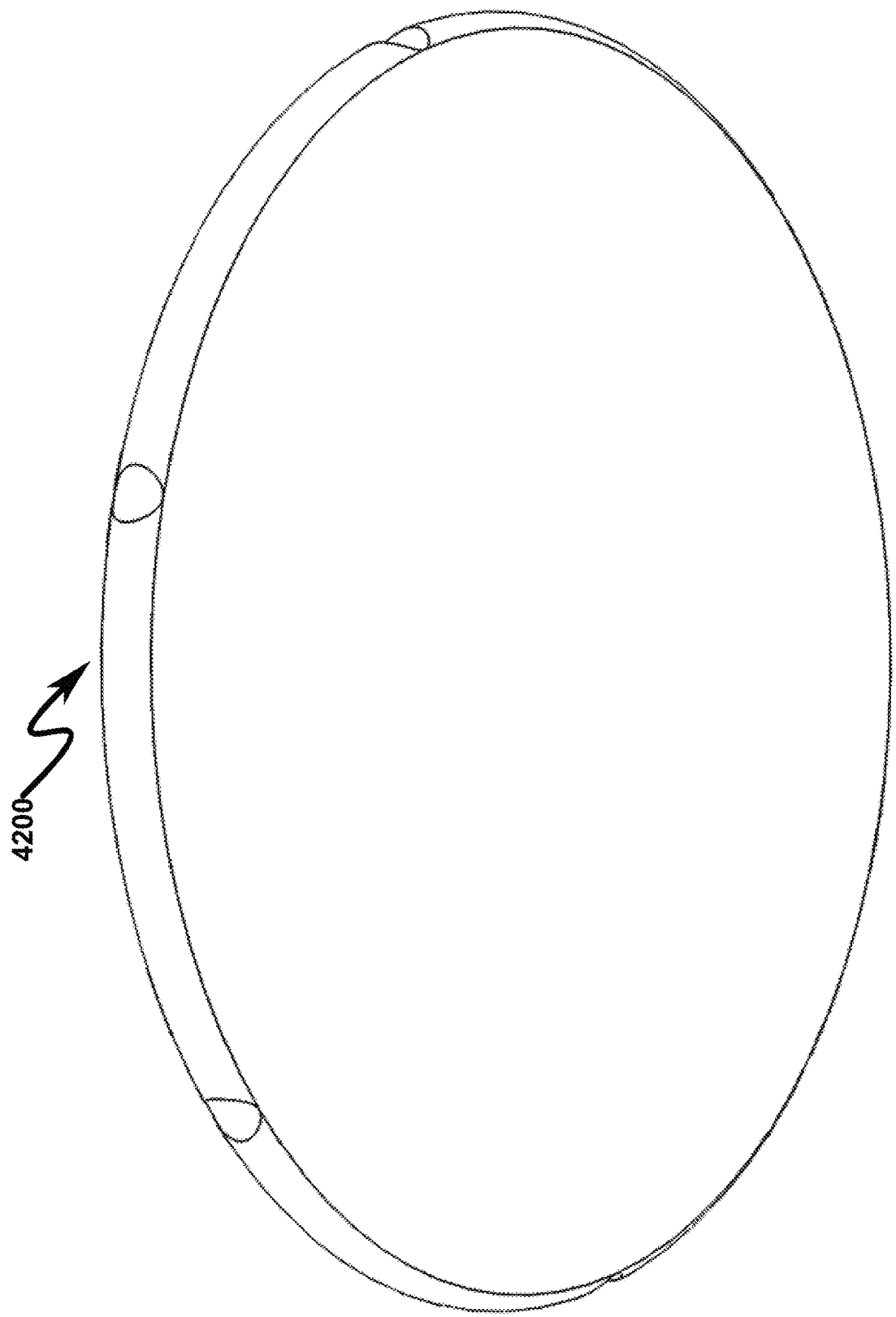
FIG. 42 illustrates a bottom front right perspective view of a preferred exemplary invention drug delivery device (DDD) disc-style embodiment incorporating multiple radial DPP pathways.
Figure 43:
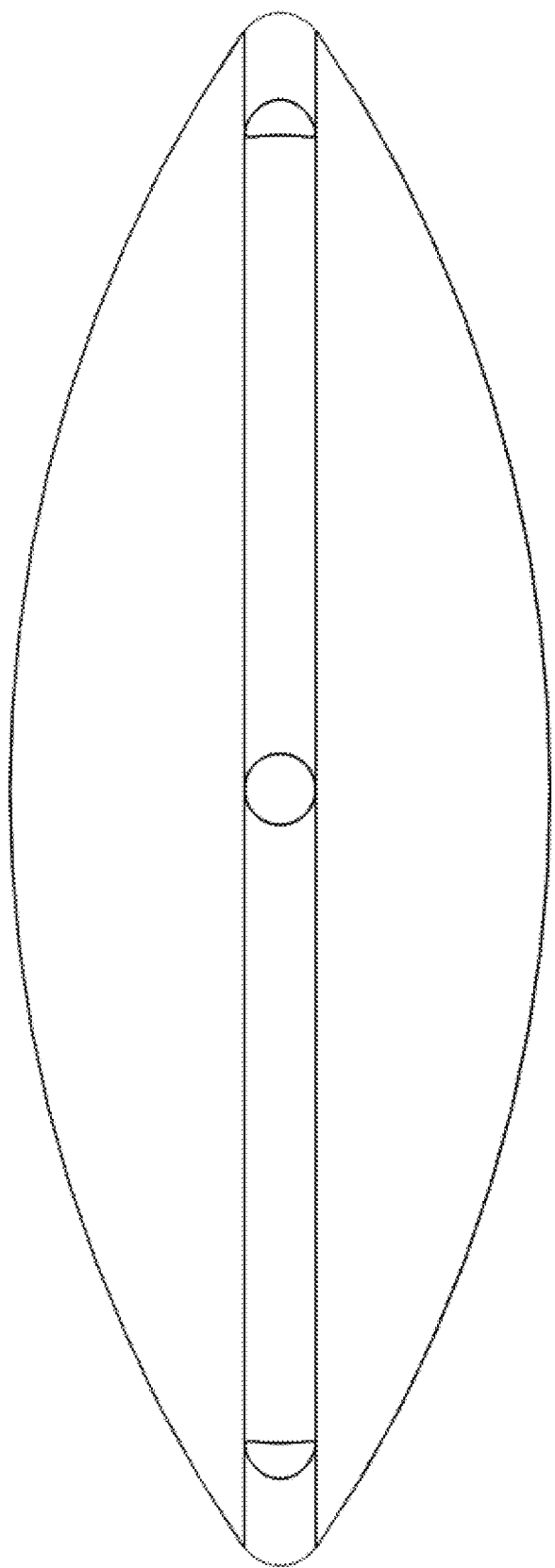
FIG. 43 illustrates a front view of a preferred exemplary invention drug delivery device (DDD) disc-style embodiment incorporating multiple radial DPP pathways.
Figure 44:
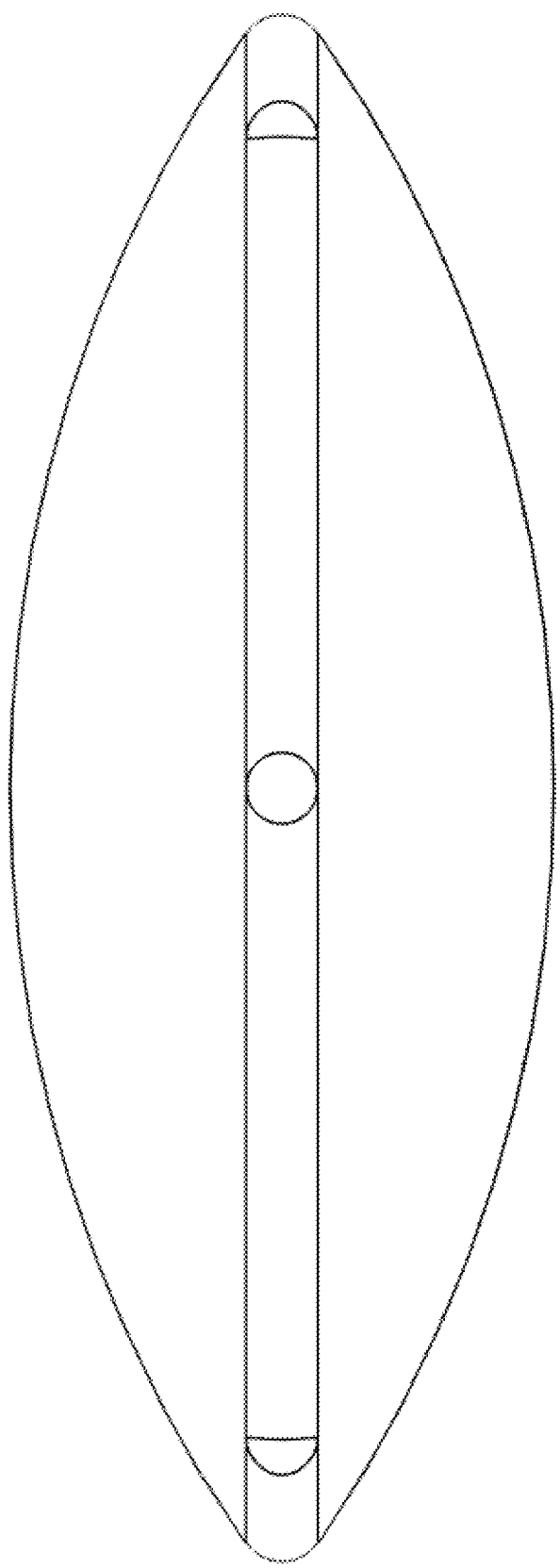
FIG. 44 illustrates a rear view of a preferred exemplary invention drug delivery device (DDD) disc-style embodiment incorporating multiple radial DPP pathways.
Figure 45:
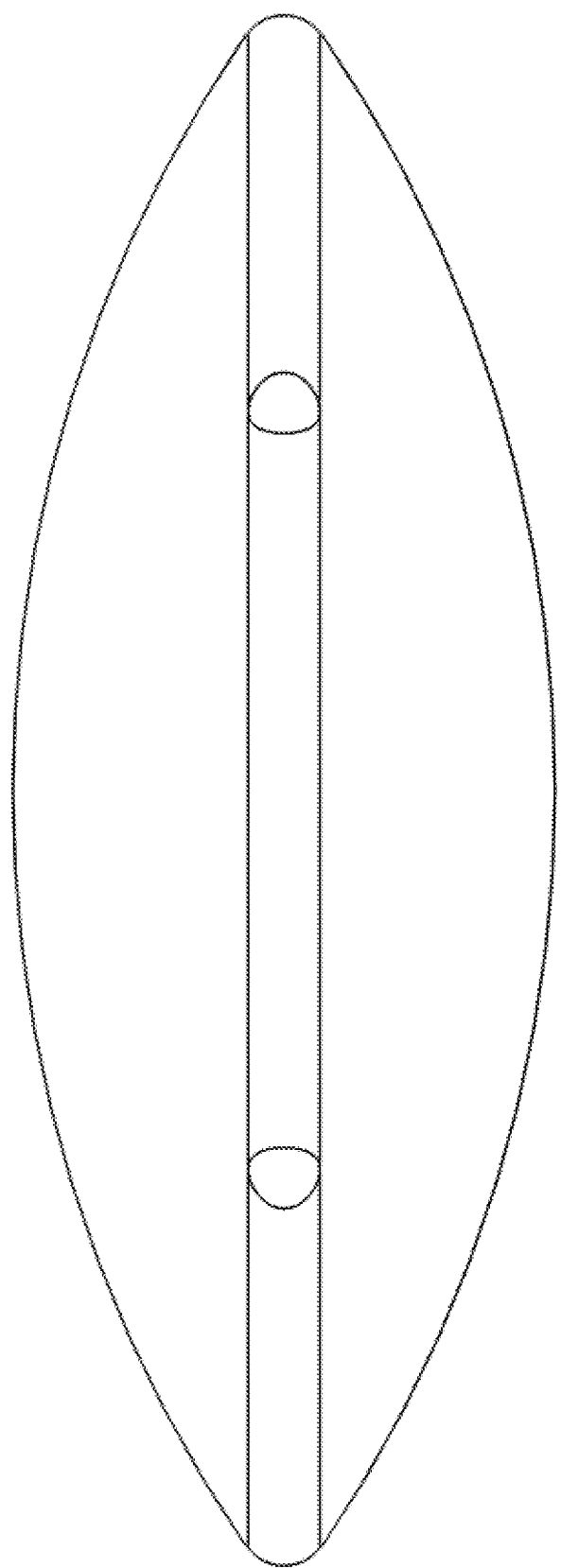
FIG. 45 illustrates a left side view of a preferred exemplary invention drug delivery device (DDD) disc-style embodiment incorporating multiple radial DPP pathways.
Figure 46:
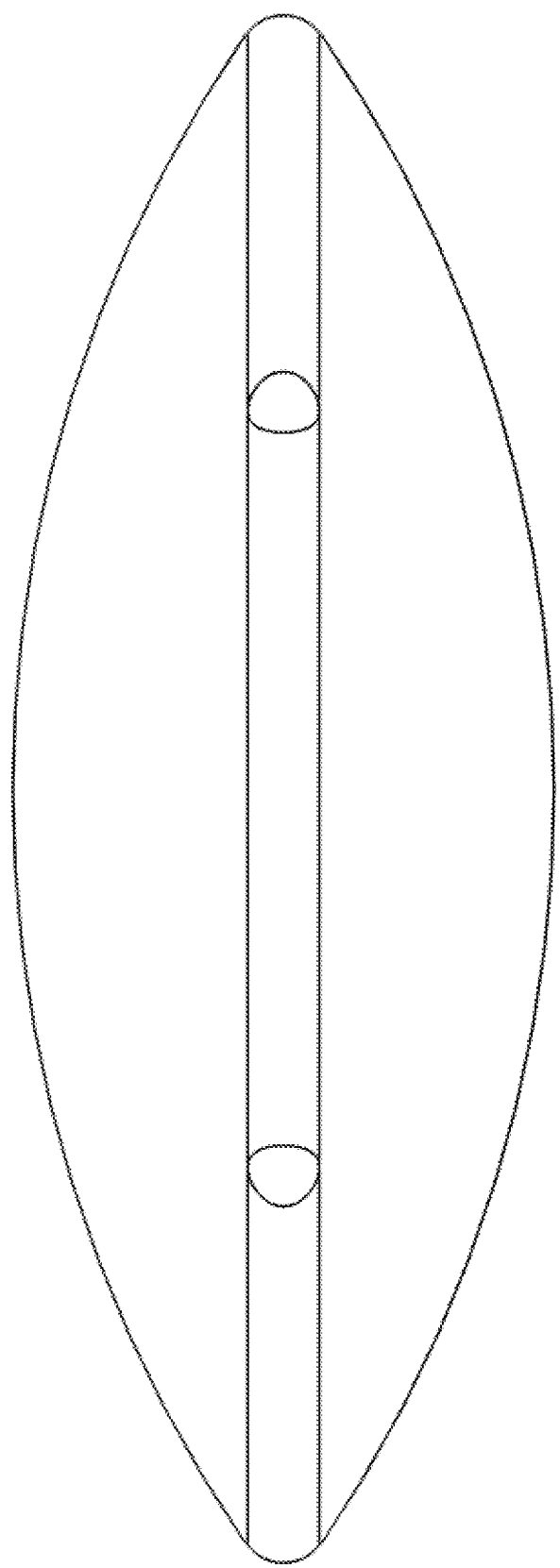
FIG. 46 illustrates a right side view of a preferred exemplary invention drug delivery device (DDD) disc-style embodiment incorporating multiple radial DPP pathways.
Figure 47:
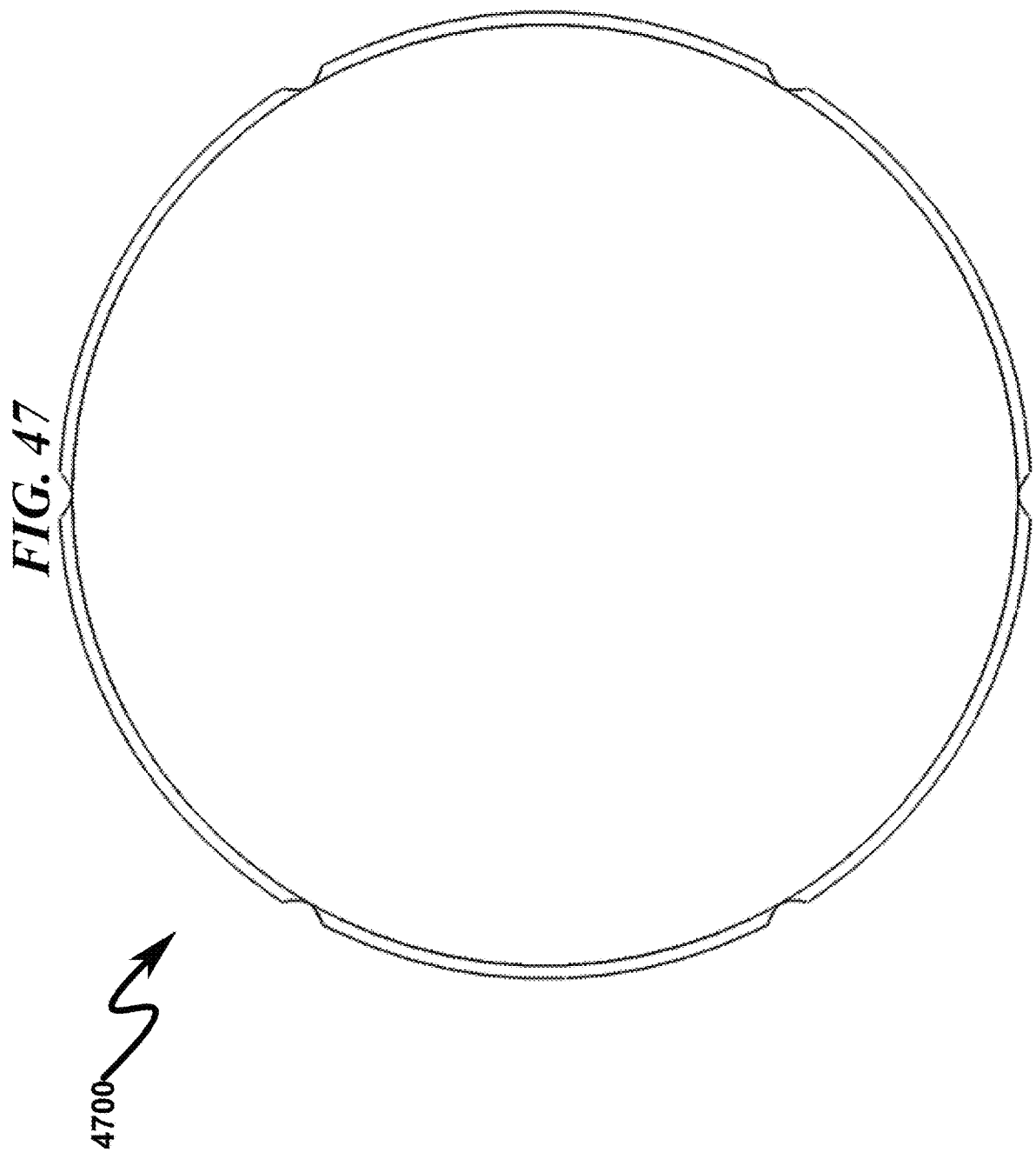
FIG. 47 illustrates a top view of a preferred exemplary invention drug delivery device (DDD) disc-style embodiment incorporating multiple radial DPP pathways.
Figure 48:
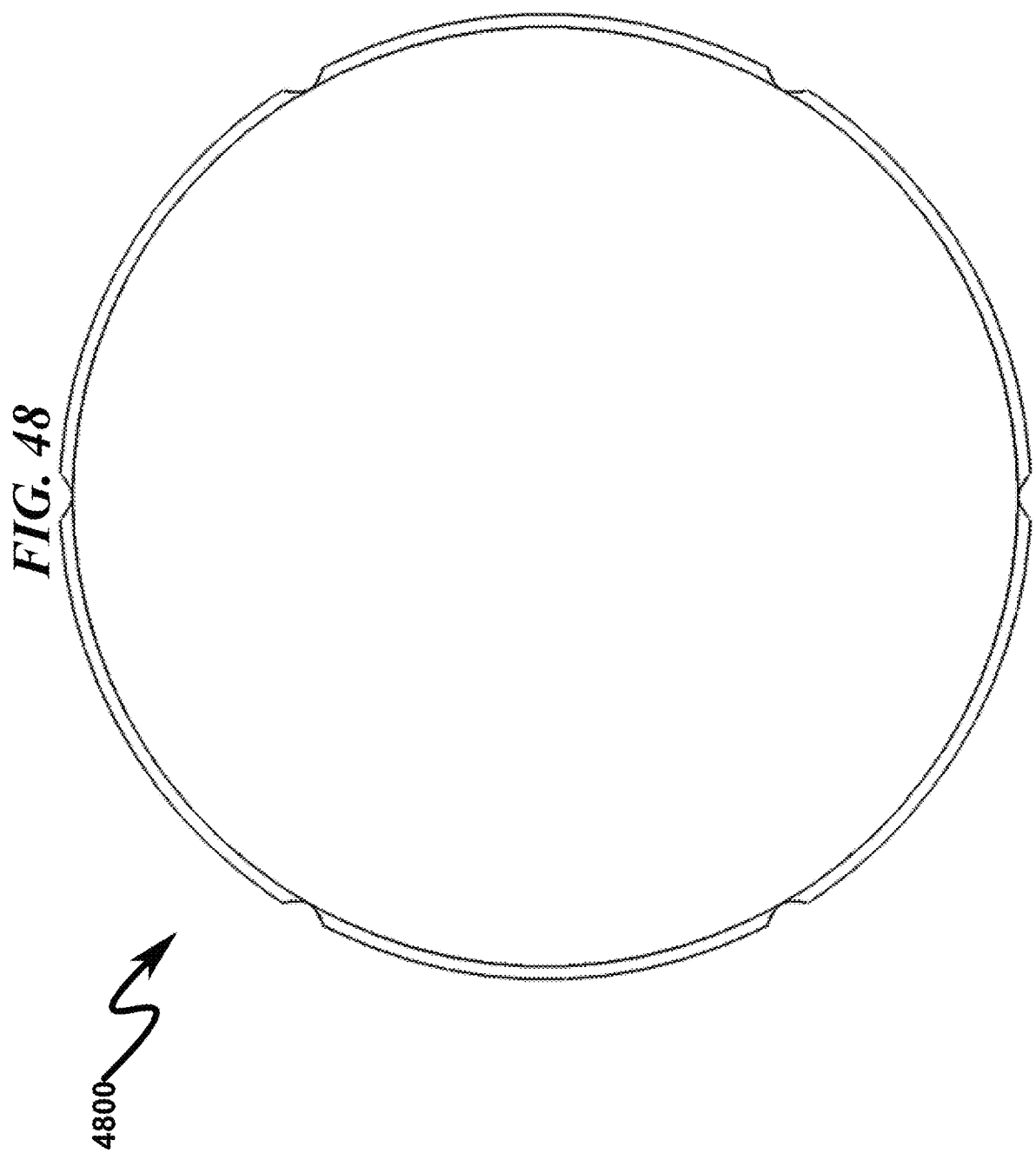
FIG. 48 illustrates a bottom view of a preferred exemplary invention drug delivery device (DDD) disc-style embodiment incorporating multiple radial DPP pathways.
Figure 49:
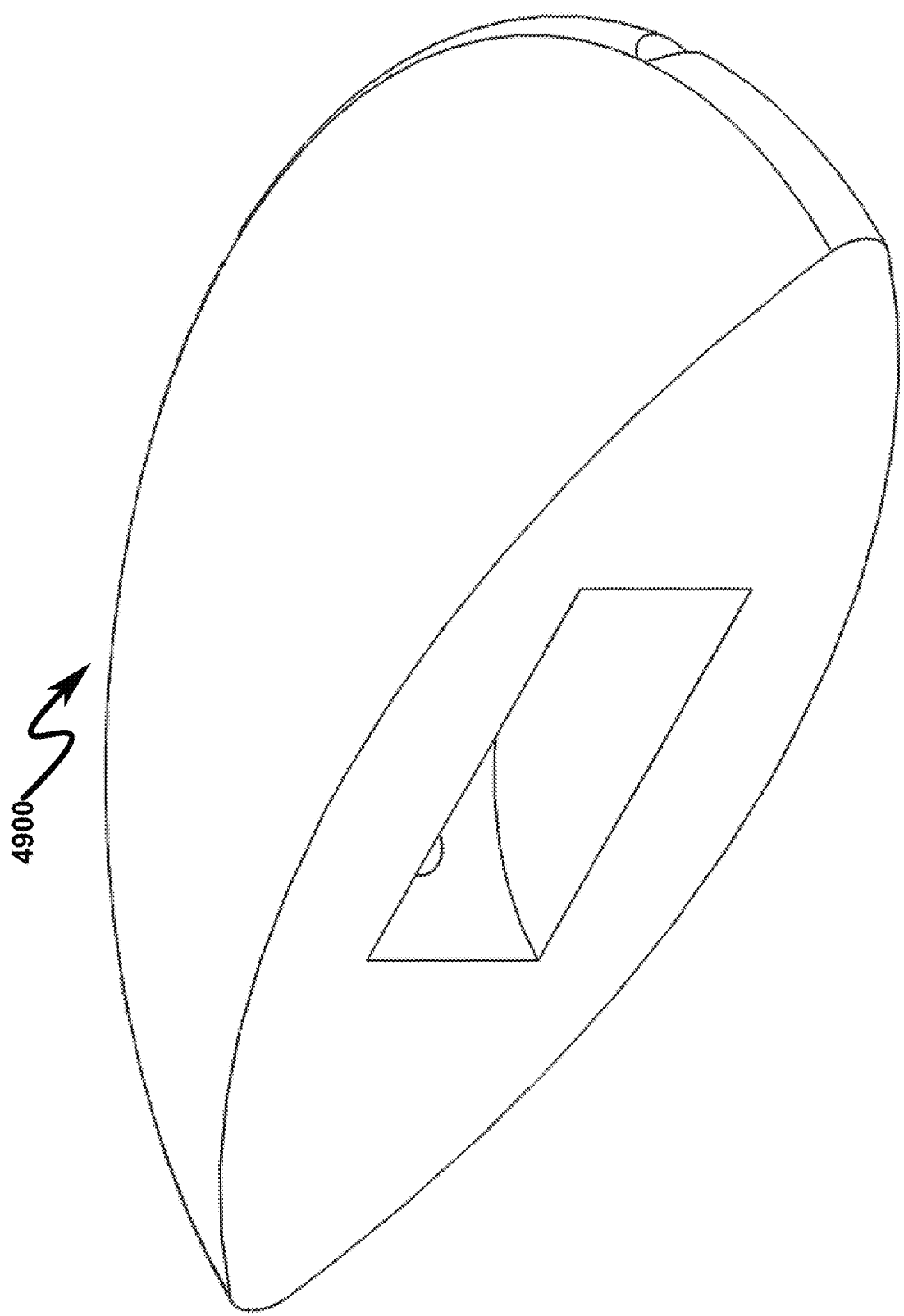
FIG. 49 illustrates a side perspective section view of a preferred exemplary invention drug delivery device (DDD) disc-style embodiment incorporating multiple radial DPP pathways.
Figure 50:
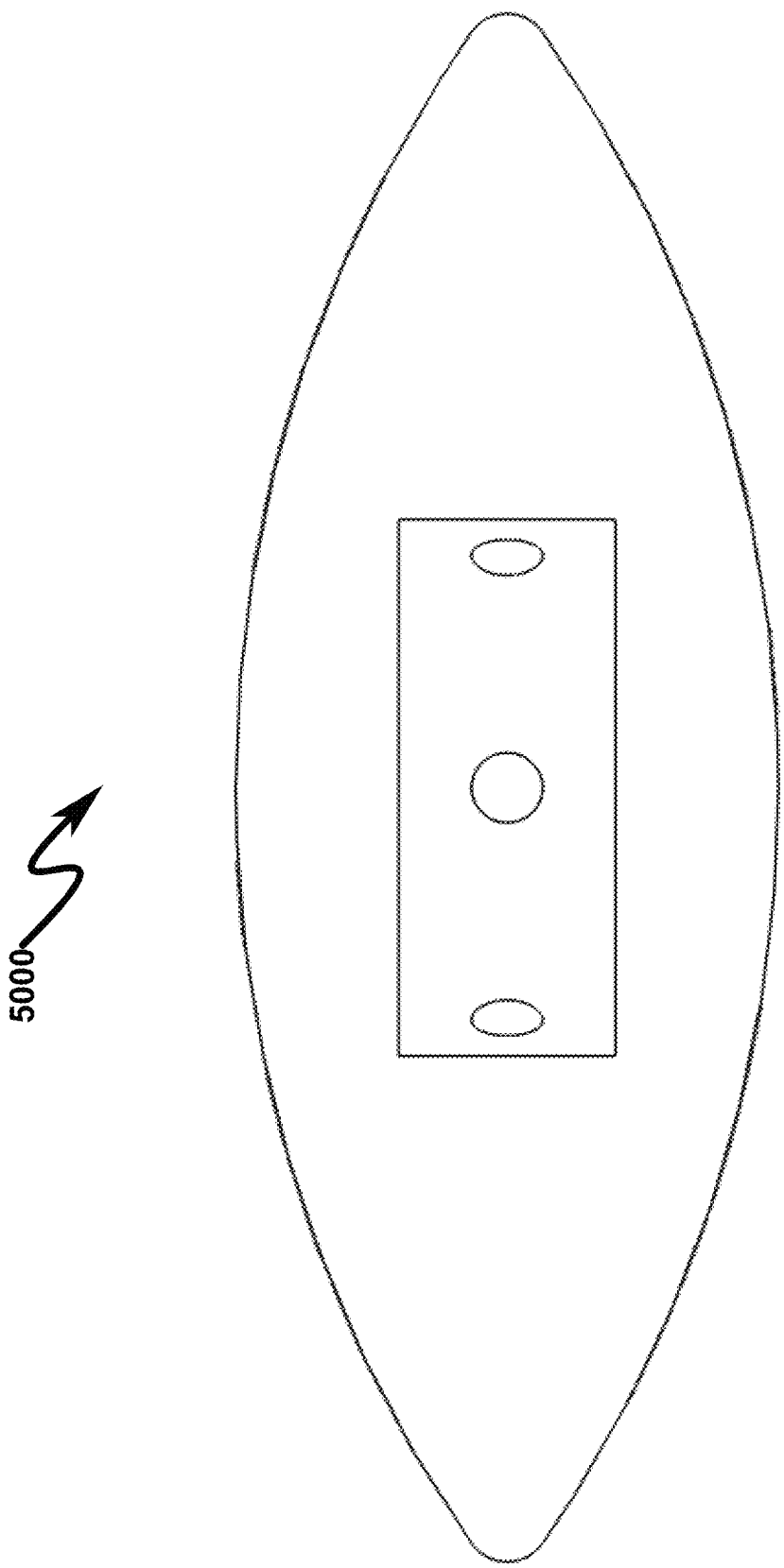
FIG. 50 illustrates a side section view of a preferred exemplary invention drug delivery device (DDD) disc-style embodiment incorporating multiple radial DPP pathways.
Figure 51:
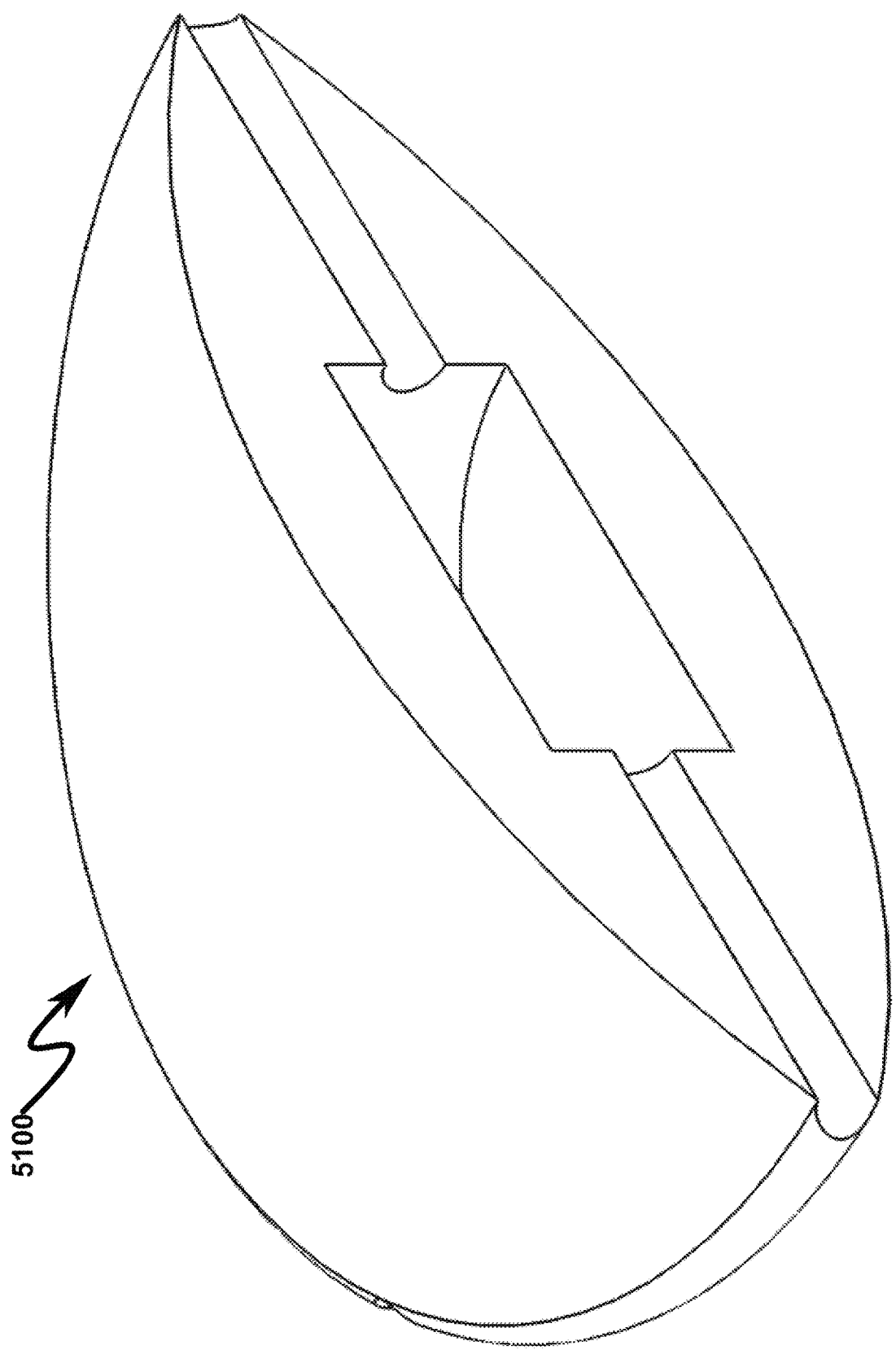
FIG. 51 illustrates a front perspective section view of a preferred exemplary invention drug delivery device (DDD) disc-style embodiment incorporating multiple radial DPP pathways.
Figure 52:
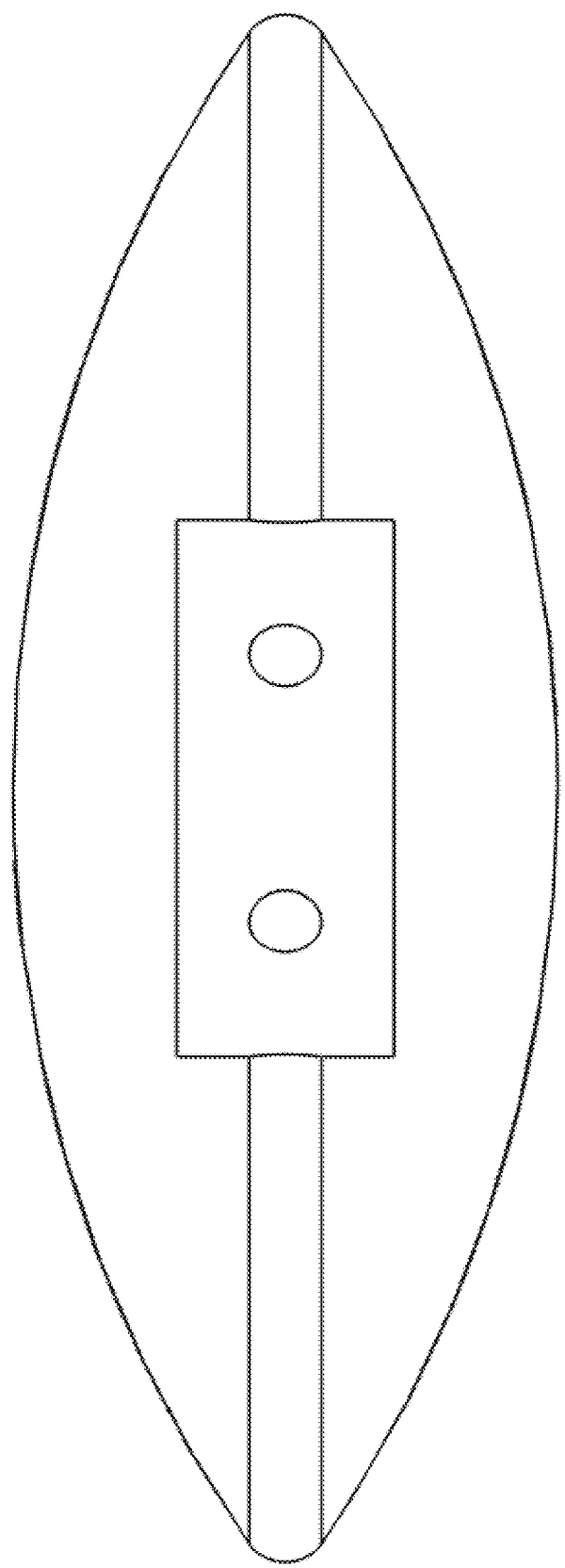
FIG. 52 illustrates a front section view of a preferred exemplary invention drug delivery device (DDD) disc-style embodiment incorporating multiple radial DPP pathways.
Figure 53:
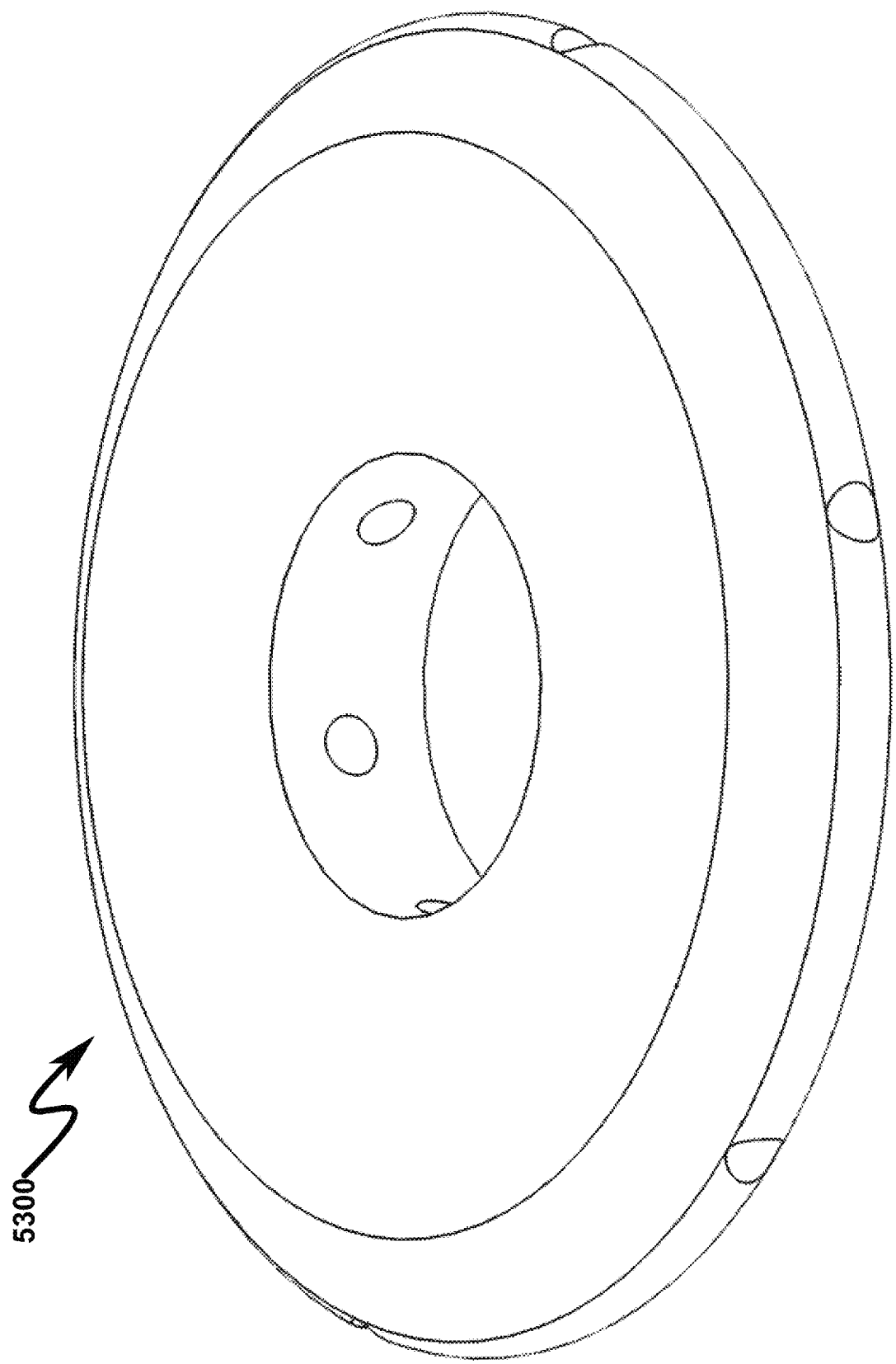
FIG. 53 illustrates a top upper perspective section view of a preferred exemplary invention drug delivery device (DDD) disc-style embodiment incorporating multiple radial DPP pathways and detailing an exemplary top-half radial drug delivery path (DDP)
Figure 54:
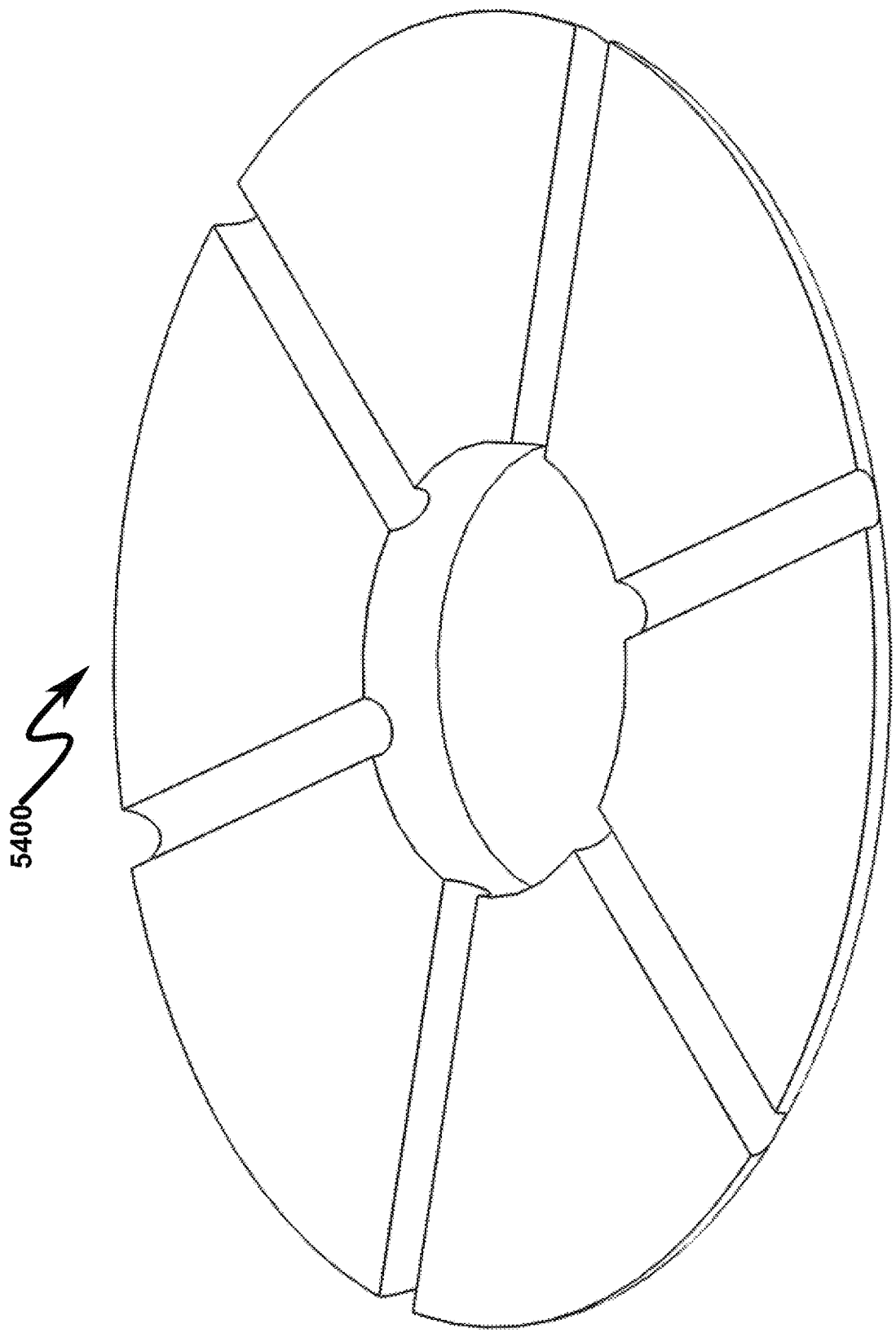
FIG. 54 illustrates a top mid-plane perspective section view of a preferred exemplary invention drug delivery device (DDD) disc-style embodiment incorporating multiple radial DPP pathways and detailing an exemplary drug delivery reservoir (DDR)
Figure 55:
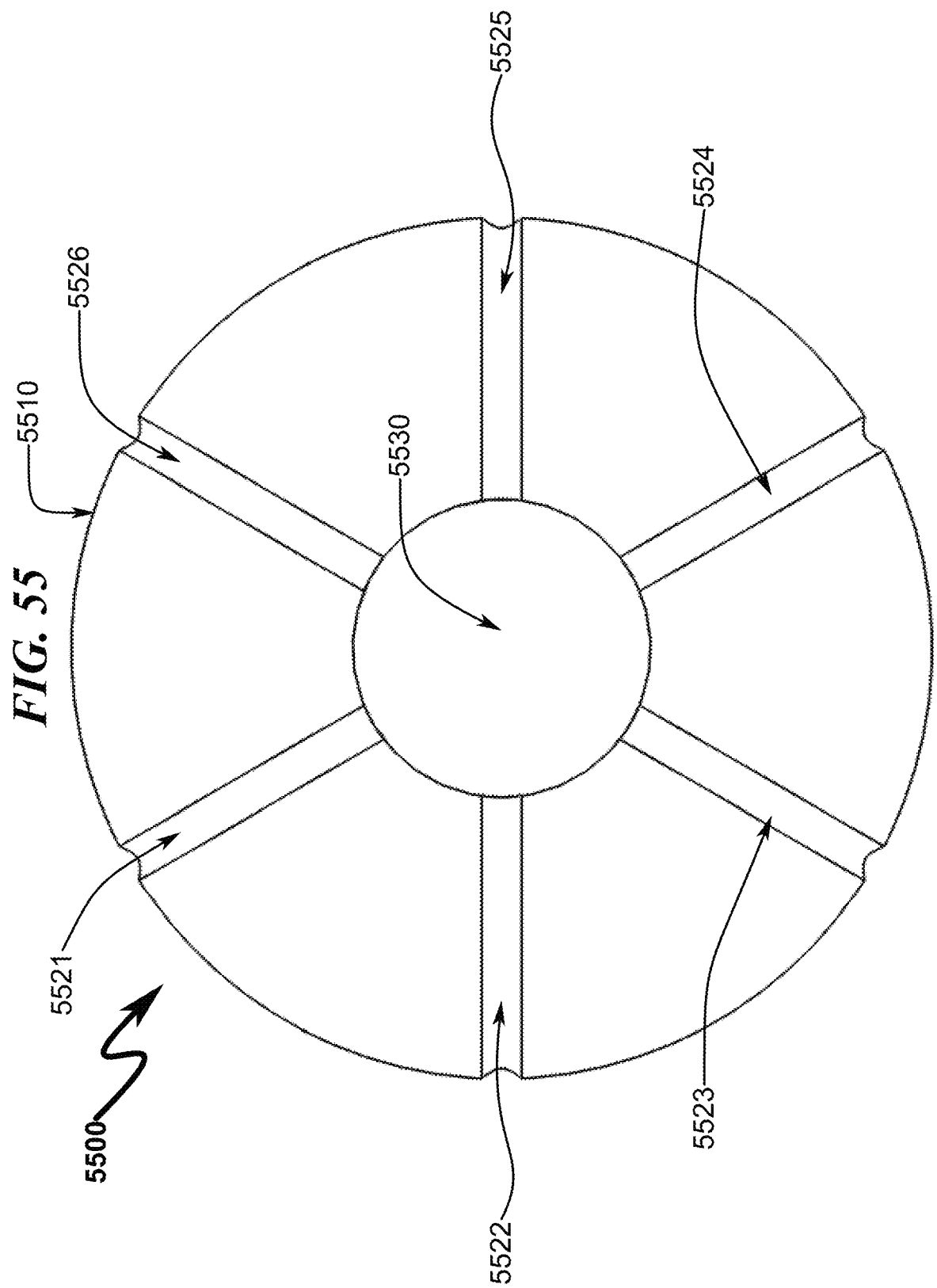
FIG. 55 illustrates a top mid-plane section view of a preferred exemplary invention drug delivery device (DDD) disc-style embodiment incorporating multiple radial DPP pathways and detailing an exemplary top-half radial drug delivery path (DDP)
Figure 56:
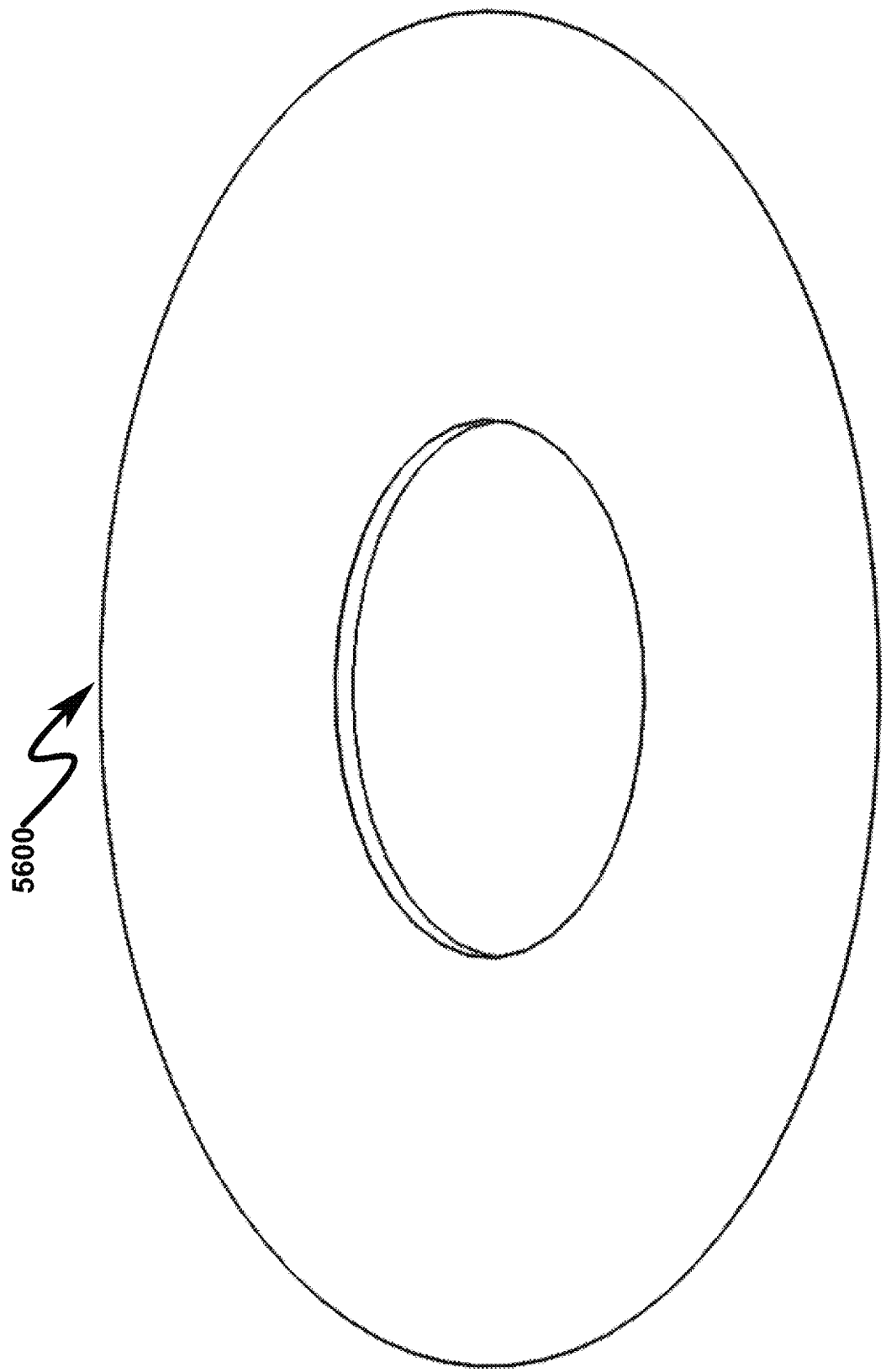
FIG. 56 illustrates a top lower perspective section view of a preferred exemplary invention drug delivery device (DDD) disc-style embodiment incorporating multiple radial DPP pathways and detailing an exemplary bottom-half radial drug delivery path (DDP)

The present invention anticipates that the DPP pathways may terminate at multiple points on the surface of the DDD. This concept is generally depicted in FIG. 41 (4100)-FIG. 56 (5600) in which an exemplary disc-style DDD (5510) is constructed and depicted in the detail section view of FIG. 55 (5500) with multiple radial DPP pathways (5521, 5522, 5523, 5524, 5525, 5526) that originate from a DDR (5530) and terminate on the surface of the DDD (5510).

DPP Line Width Variations (5700)-(5800)

Figure 57:
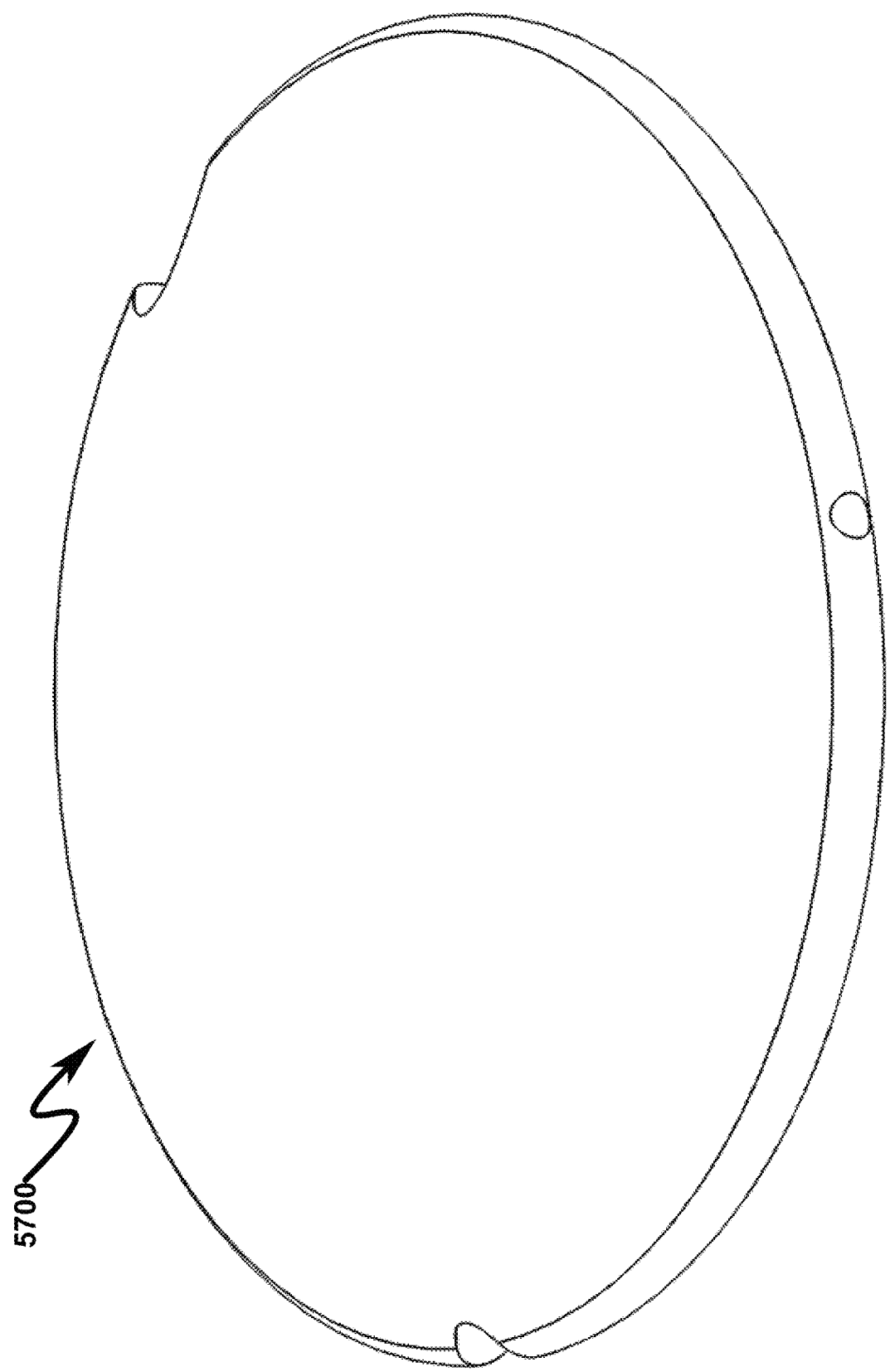
FIG. 57 illustrates a top perspective view of a preferred exemplary invention drug delivery device (DDD) disc-style embodiment incorporating DPP comprising lines of different width.
Figure 58:
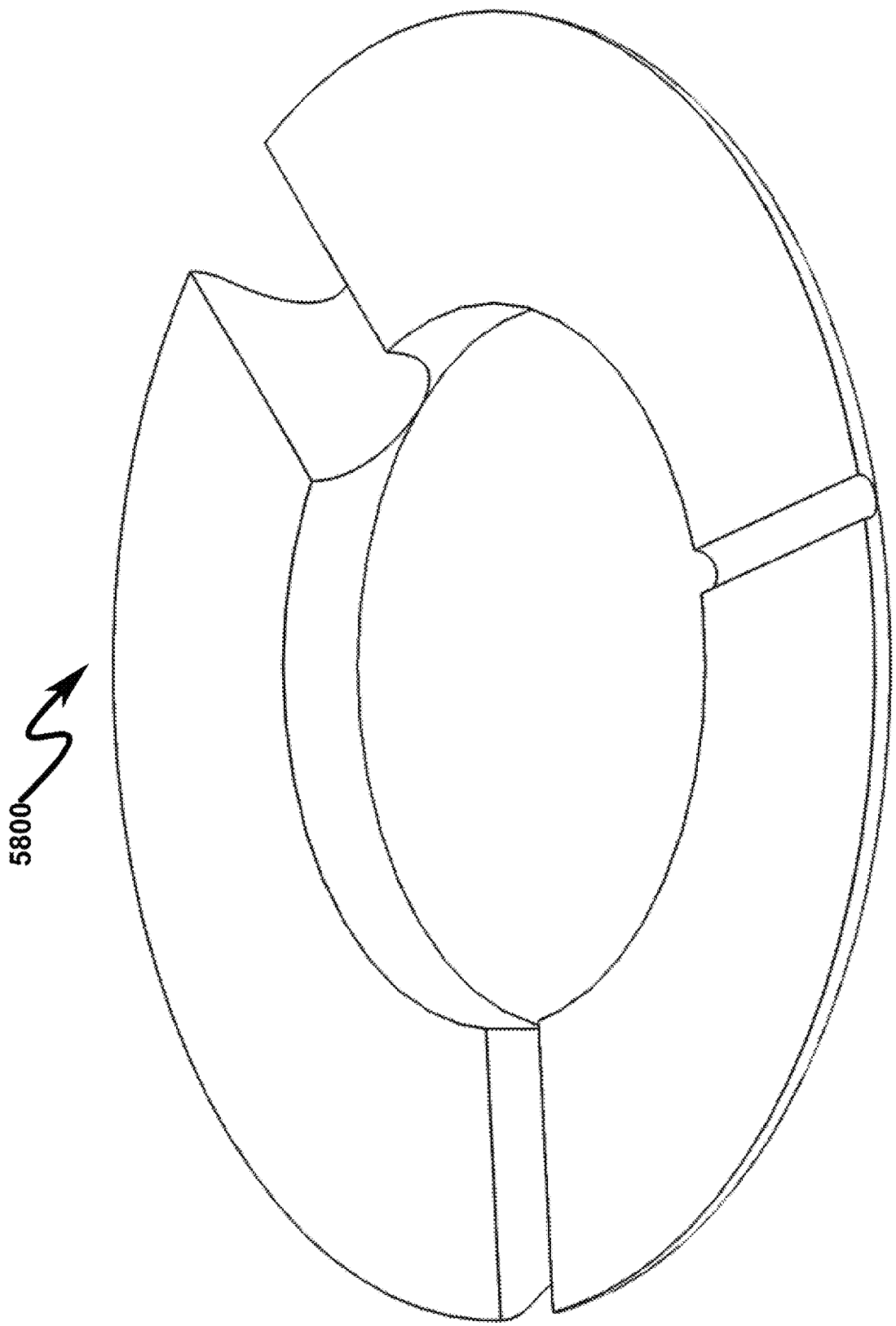
FIG. 58 illustrates a top perspective section view of a preferred exemplary invention drug delivery device (DDD) disc-style embodiment incorporating DPP comprising lines of different width.

The present invention anticipates that the DPP pathways may incorporate different line widths. This concept is generally depicted in FIG. 57 (5700)-FIG. 58 (5800) in which an exemplary disc-style DDD is constructed having a multiple number (3) of different line widths associated with the DPP pathways in the DDD.

DPP Cross Sectional Area Variations (5900)-(6000)

Figure 59:
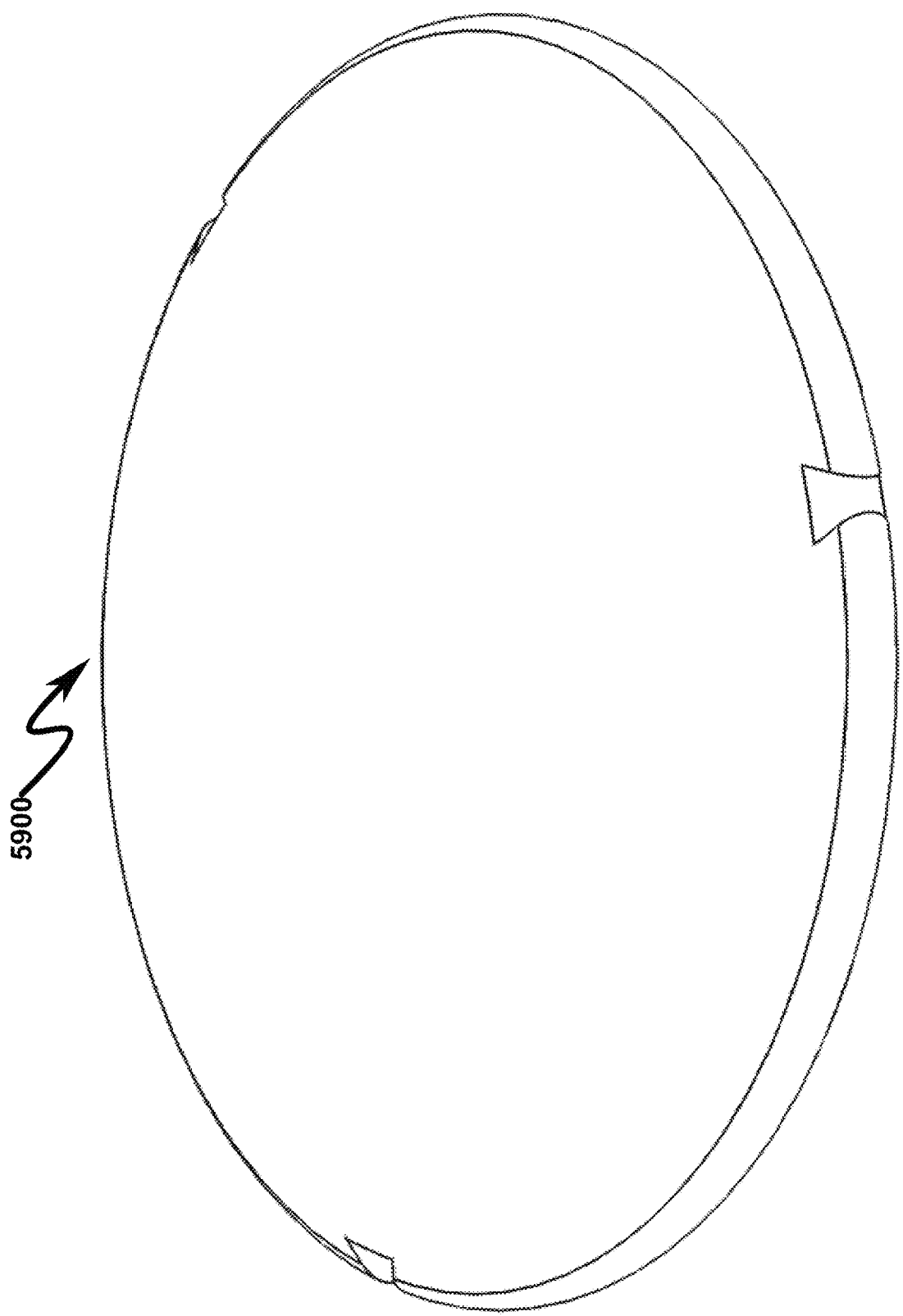
FIG. 59 illustrates a top perspective view of a preferred exemplary invention drug delivery device (DDD) disc-style embodiment incorporating DPP comprising varying cross sectional areas.
Figure 60:
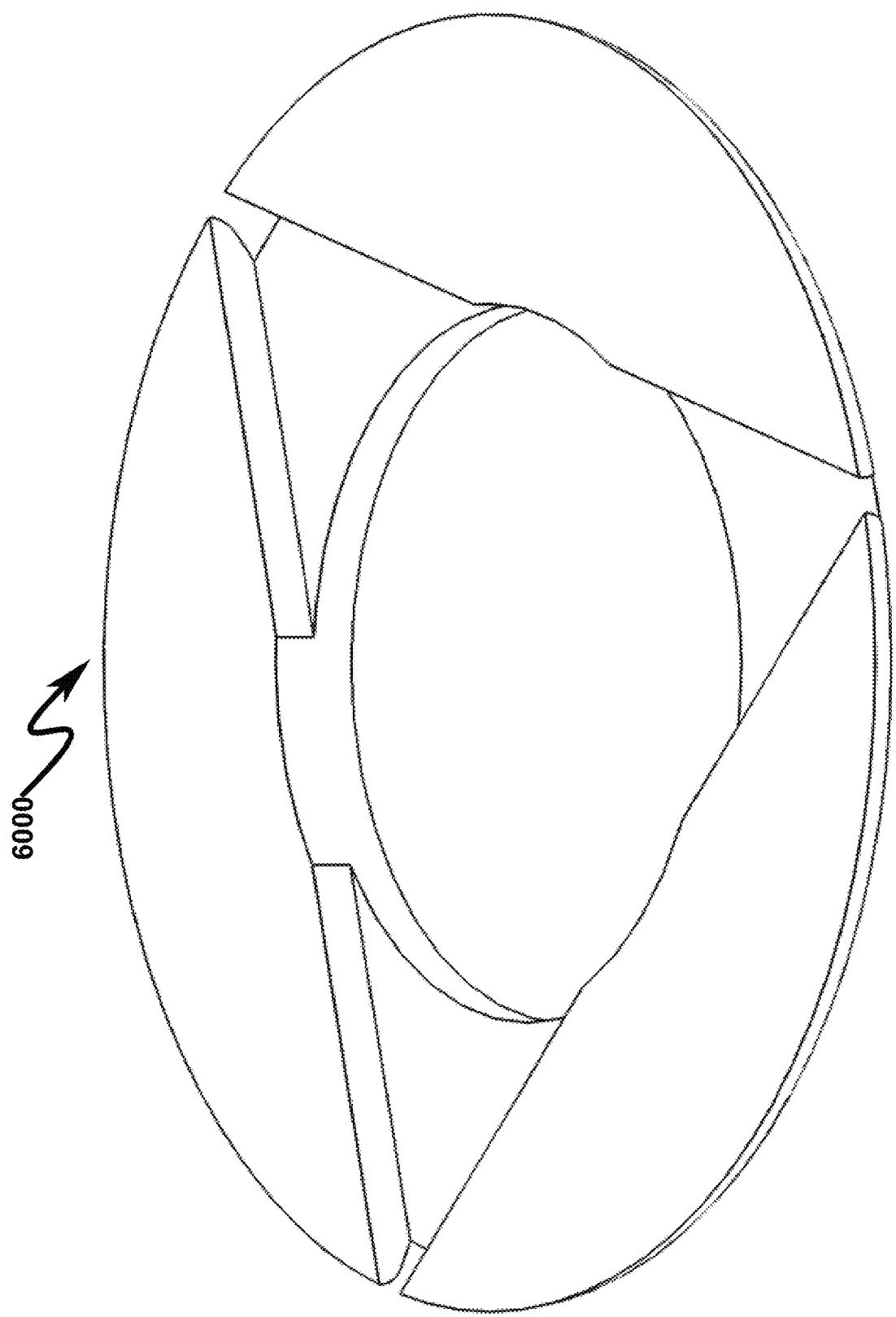
FIG. 60 illustrates a top perspective section view of a preferred exemplary invention drug delivery device (DDD) disc-style embodiment incorporating DPP comprising varying cross sectional areas.

The present invention anticipates that the DPP pathways may incorporate different cross sectional pathway areas. This concept is generally depicted in FIG. 59 (5900)-FIG. 60 (6000) in which an exemplary disc-style DDD is constructed having a varying cross sectional areas associated with the DPP pathways in the DDD.

DDD Identifying Indicia Locator (6100)-(6400)

Figure 61:
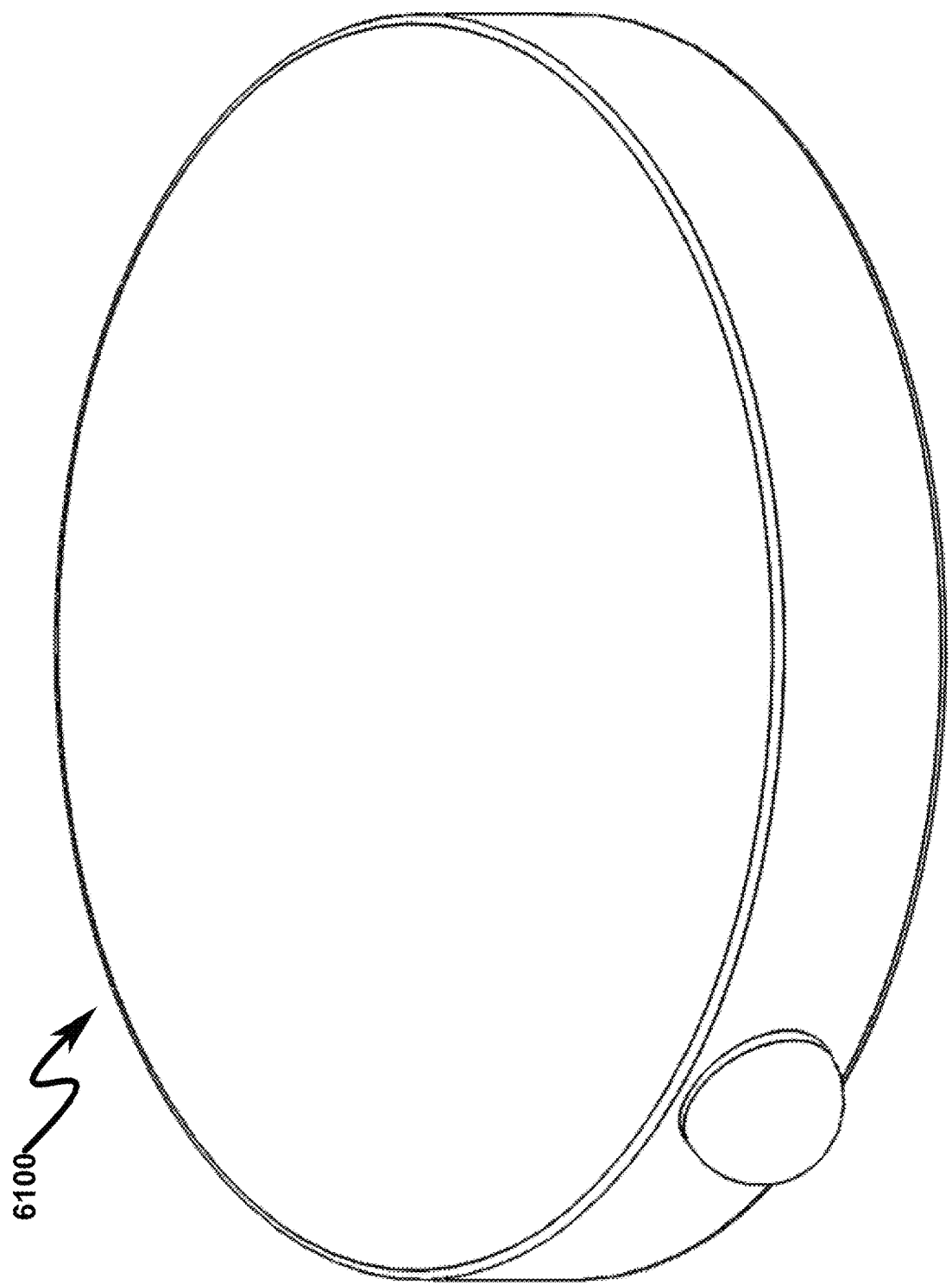
FIG. 61 illustrates a top perspective view of a preferred exemplary invention drug delivery device (DDD) button-style embodiment incorporating a bump-style identifying indicia locator (IIL)
Figure 62:
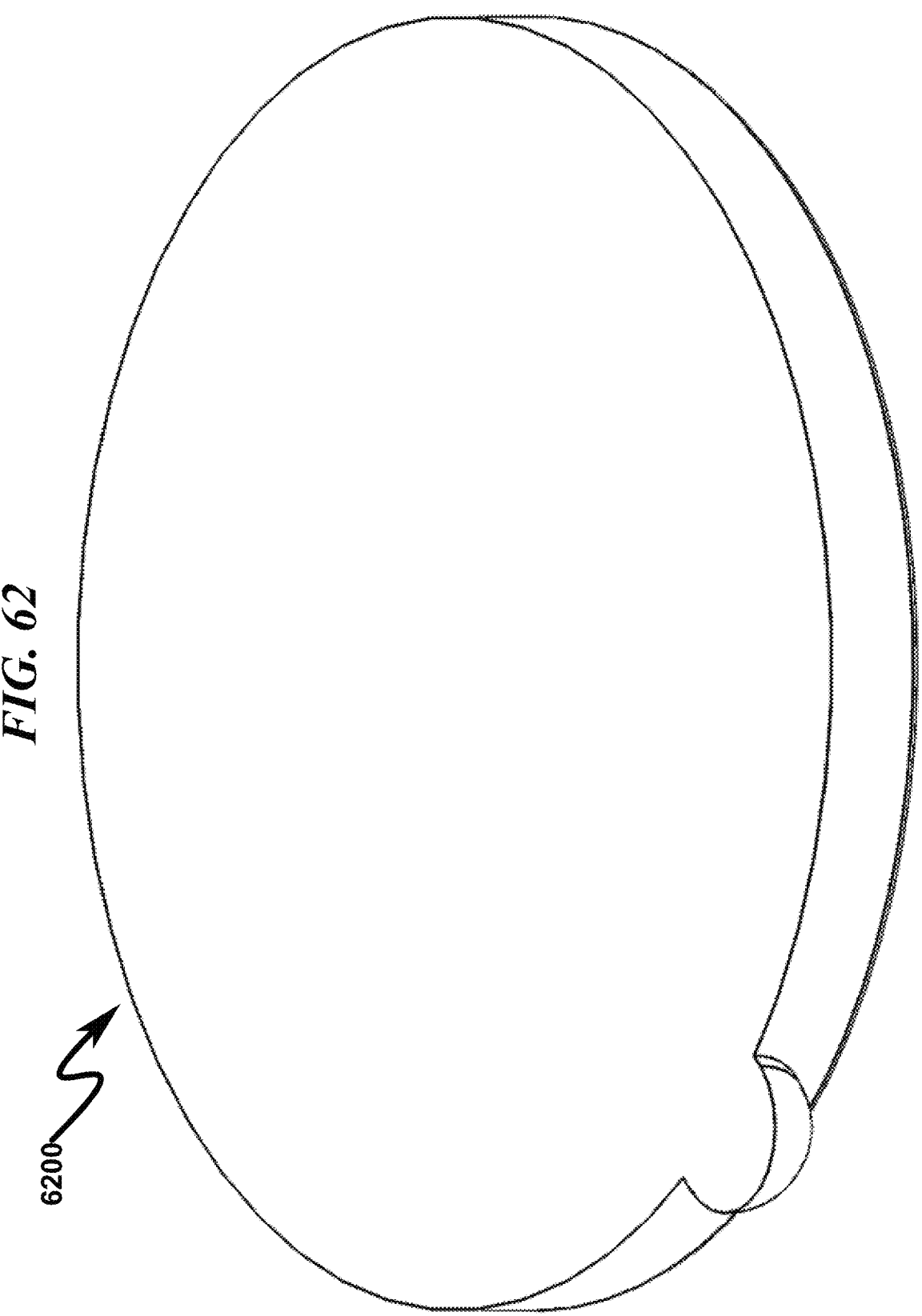
FIG. 62 illustrates a top perspective section view of a preferred exemplary invention drug delivery device (DDD) button-style embodiment incorporating a bump-style identifying indicia locator (IIL)
Figure 63:
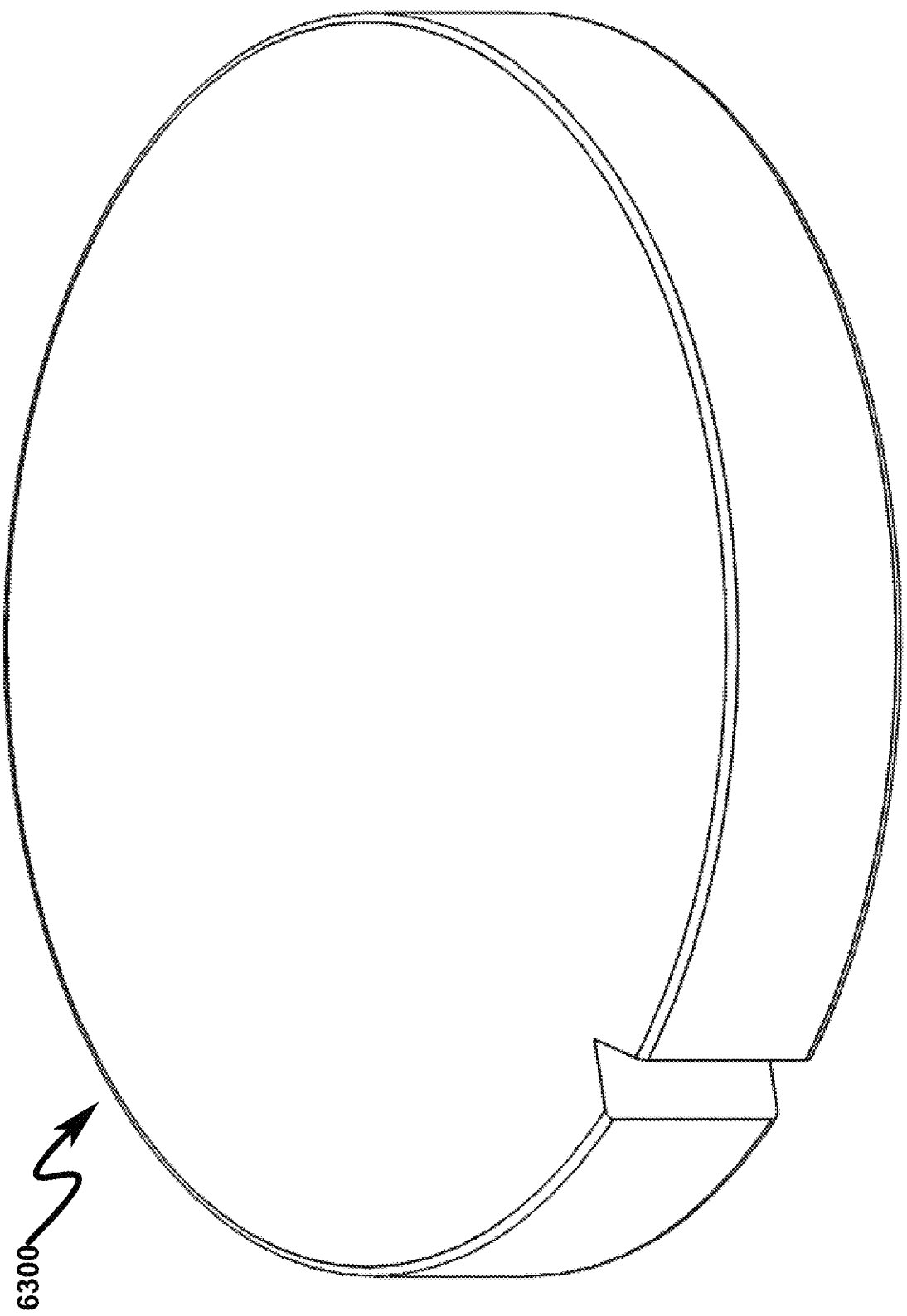
FIG. 63 illustrates a top perspective view of a preferred exemplary invention drug delivery device (DDD) button-style embodiment incorporating a notch-style identifying indicia locator (IIL)
Figure 64:
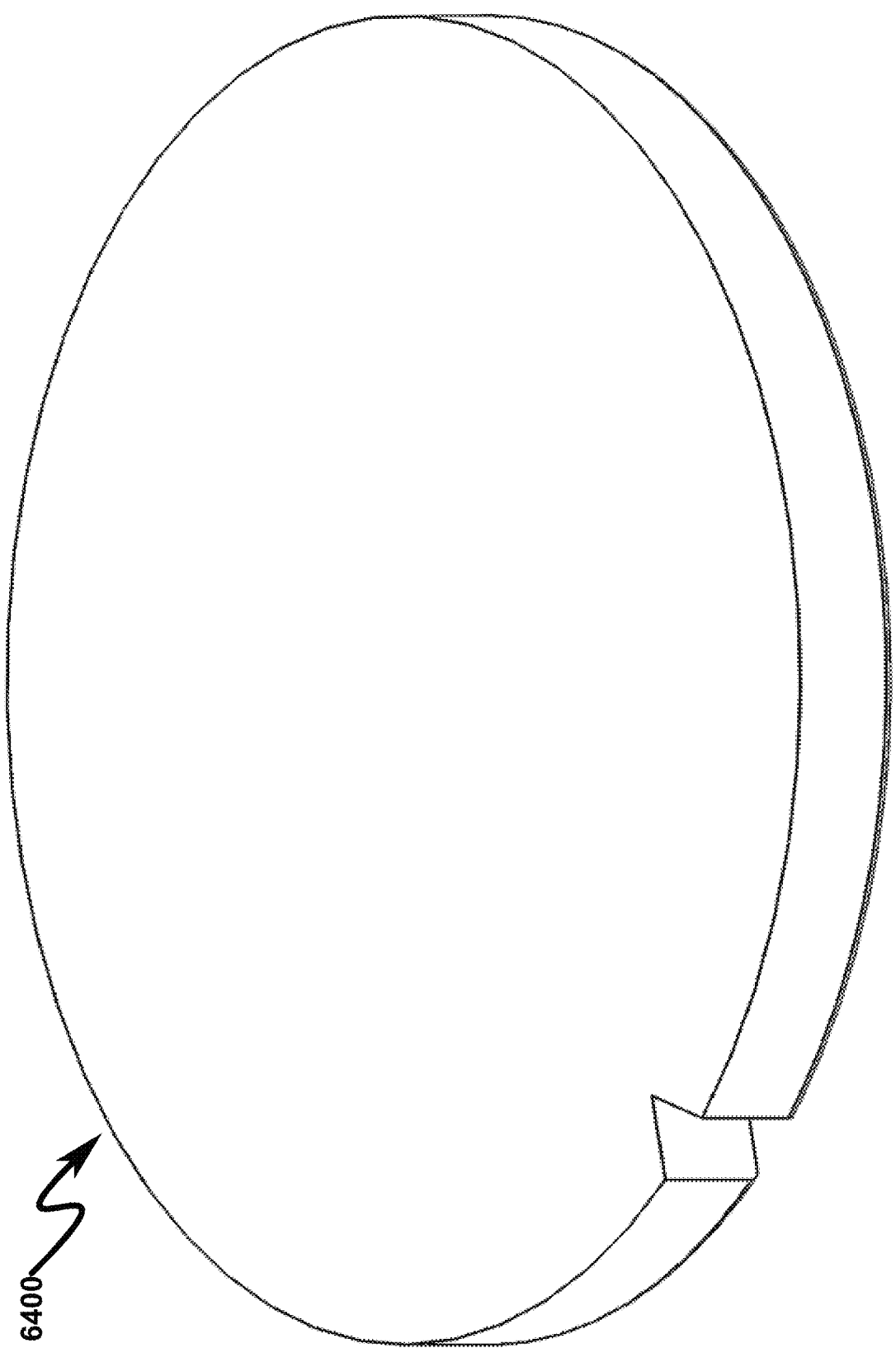
FIG. 64 illustrates a top perspective section view of a preferred exemplary invention drug delivery device (DDD) button-style embodiment incorporating a notch-style identifying indicia locator (IIL).

As generally illustrated in the drawings, the DDD may incorporate an identifying indicia locator (IIL) locating an external delivery port (EDP), the identifying indicia selected from a group consisting of: index face (FIG. 17 (1700)-FIG. 32 (3200)); bump (FIG. 61 (6100)-FIG. 62 (6200)); and notch (FIG. 63 (6300)-FIG. 64 (6400)). One skilled in the art will recognize that these exemplary IIL locators represent only a few of a wide variety of possible IIL implementations, and as such the present invention scope is not limited to these examples.

Drug Delivery Customization

The present invention specifically anticipates that the drug delivery system parameters may be modified to allow for a custom hydrophilicity change depth/width which may be used to control the drug delivery speed and/or flow.

The present invention specifically anticipates that the femtosecond laser pulse energy may be adjusted to affect the drug delivery speed and/or flow.

The present invention specifically anticipates that the system parameters may be modified to allow for a custom hydrophilicity width and/or depth that may be used to control the drug delivery speed and/or flow.

The present invention specifically anticipates that patient specific information may be added to allow for a custom drug delivery option based on specific patient requirements.

The present invention specifically anticipates that the DDD may be comprised of a biological tissue that is receptive to a two-photon hydrophilicity change and the drug delivery system may be used to improve water flow of the biological tissue.

System Summary

The present invention system may be broadly generalized as a drug delivery system comprising:
(a) laser pattern generator (LPG);
(b) computer control device (CCD);
(c) drug pathway database (DPD);
(d) drug delivery device (DDD); and
(e) drug delivery payload (DDP);
wherein:
the CCD is configured to retrieve a predetermined drug payload pathway (DPP) from the DPD;
the CCD is configured to control the LPG to imprint the DPP onto the DDD using a femtosecond laser radiation source (FLS);
the CCD is configured to generate hydrophilic modification of the DDD in response to the imprinting of the DDD with the DPP;
the CCD is configured to expose the imprinted DDD to the DDP based on a predetermined drug exposure profile (DEP); and
the hydrophilic modification of the DDD permits the DDP to be wicked to or from the DDD based on the DPP imprinted into DDD.

This general system summary may be augmented by the various elements described herein to produce a wide variety of invention embodiments consistent with this overall design description.

Method Summary

The present invention method may be broadly generalized as a drug delivery method comprising:
(1) selecting a drug delivery device (DDD);
(2) selecting a drug delivery payload (DDP);
(3) with a computer control device (CCD), selecting a drug payload pathway (DPP) from a drug pathway database (DPD);
(4) with the CCD, imprinting the selected DPP onto DDD using a femtosecond laser radiation source (FLS) controlled by a laser pattern generator (LPG);
(5) injecting and/or time exposing the patterned DDD to and/or with the drug delivery payload (DDP); and
(6) applying the injected and/or time exposed DDD to a drug delivery target (DDT).

This general method may be modified heavily depending on a number of factors, with rearrangement and/or addition/deletion of steps anticipated by the scope of the present invention. Integration of this and other preferred exemplary embodiment methods in conjunction with a variety of preferred exemplary embodiment systems described herein is anticipated by the overall scope of the present invention.

System/Method Variations

The present invention anticipates a wide variety of variations in the basic theme of construction. The examples presented previously do not represent the entire scope of possible usages. They are meant to cite a few of the almost limitless possibilities.

This basic system, method, and product-by-process may be augmented with a variety of ancillary embodiments, including but not limited to:

An embodiment wherein the FLS comprises a laser source having a pulse duration of 450 fs or shorter, a wavelength in the range of 400 nm to 1060 nm, and a repetition rate of in the range of 0.01 MHz to 100 MHz, and a pulse energy in the range of 0.1 nanojoules to 3500 nanojoules.

An embodiment wherein the LPG is configured to adjust laser radiation energy generated by the FLS and imparted to the DDD to affect drug delivery speed of the DDP along the DPP.

An embodiment wherein the LPG is configured to adjust laser radiation energy generated by the FLS and imparted to the DDD to affect drug delivery flow of the DDP along the DPP.

An embodiment wherein the DDD comprises a form factor selected from a group consisting of: capsule; button; disc; pouch; tab; and intraocular lens (IOL).

An embodiment wherein the DPP comprises a pathway pattern selected from a group consisting of: helix; spiral; rectangular helix; rectangular spiral; serpentine; radial; lines of different width; and pathways of varying cross section.

An embodiment wherein the DDD comprises an acrylic material incorporating an ultraviolet (UV) absorber having a concentration of 10% or less by volume.

An embodiment wherein the DDD comprises an internal drug delivery reservoir (DDR) configured to accept the DDP.

An embodiment wherein the DDD comprises an internal refillable drug delivery reservoir (DDR) configured to accept the DDP.

An embodiment wherein the DDD comprises an identifying indicia locating an external delivery port (EDP), the identifying indicia selected from a group consisting of: index face; bump; and notch.

An embodiment wherein the DDD comprises an external delivery port (EDP).

An embodiment wherein the DDD is configured to accept injection of the DDP via the use of a needle syringe.

An embodiment wherein the DDD is configured to seal a drug delivery reservoir (DDR) after injection of the DDP into the DDR via the use of a needle syringe.

An embodiment wherein the CCD is configured to allow for a customized hydrophilicity change depth within the DDD to control drug delivery speed of the DDP within the DPP.

An embodiment wherein the CCD is configured to allow for a customized hydrophilicity change width within the DDD to control drug delivery speed of the DDP within the DPP.

An embodiment wherein the CCD is configured to allow for a customized hydrophilicity change depth within the DDD to control drug delivery flow of the DDP within the DPP.

An embodiment wherein the CCD is configured to allow for a customized hydrophilicity change width within the DDD to control drug delivery flow of the DDP within the DPP.

An embodiment wherein the CCD is configured to accept patient specific information to customize the DPP based on specific requirements of the patient.

An embodiment wherein the DDD comprises biological tissue that is receptive to a two-photon hydrophilicity change and the LPG is configured to modify the hydrophilicity of the biological tissue via radiation from the FLS.

An embodiment wherein the DDD comprises biological tissue that is receptive to a two-photon hydrophilicity change and wherein the LPG is configured to modify the biological tissue via radiation from the FLS to increase water flow within the biological tissue via activation of a hydrophilicity change imparted on the biological tissue by the FLS.

The present invention specifically anticipates and one skilled in the art will recognize that other embodiments are possible based on combinations of elements and configurations taught within the above invention descriptions.

CONCLUSION

A customizable drug delivery system and method utilizing a laser pattern generator (LPG) to define application of a drug delivery payload (DDP) contained within a drug delivery device (DDD) to a drug delivery target (DDT) has been disclosed. A computer control device (CCD) supervises the LPG to select a drug payload pathway (DPP) from a drug pathway database (DPD) and writes the selected DPP to the DDD. This pathway patterning process (PPP) modifies the hydrophilic properties of the DDD and enables the DDD to selectively attract and absorb the DDP. The DDD is then injected with the DDP or exposed for drug exposure time (DET) by the CCD and DPD during which the DPP written to the DDD absorbs a controlled amount of DDP. The DDD when subsequently inserted into a drug delivery target (DDT) delivers the DDP to the DDT under controlled delivery rates defined by the DPP and the DET.

What is claimed is:

1. A drug delivery system comprising:

(a) a laser pattern generator (LPG);

(b) a computer control device (CCD);

(c) a drug pathway database (DPD);
(d) a drug delivery device (DDD); and
(e) a drug delivery payload (DDP);
wherein:
said CCD is configured to retrieve a predetermined drug payload pathway (DPP) from said DPD;
said CCD is configured to control said LPG to imprint said DPP onto said DDD using a femtosecond laser radiation source (FLS);
said CCD is configured to generate hydrophilic modification of said DDD in response to said imprinting of said DDD with said DPP by said CCD;
said LPG is configured to create hydrophilic DPP in said DDD that leads to the surface of said DDD, thereby creating hydrophilic channels within said DDD;
said CCD is configured to expose said imprinted DDD to said DDP based on a predetermined drug exposure profile (DEP); and
said hydrophilic modification of said DDD permits said DDP to be wicked to or from said DDD based on said DPP imprinted into said DDD.

2. The drug delivery system of claim 1 wherein said FLS comprises a laser source having a pulse duration of 450 fs or shorter, a wavelength in the range of 400 nm to 1060 nm, and a repetition rate of in the range of 0.01 MHz to 100 MHz, and a pulse energy in the range of 0.1 nanojoules to 3500 nanojoules.

3. The drug delivery system of claim 1 wherein said LPG is configured to adjust laser radiation energy generated by said FLS and imparted to said DDD to affect drug delivery speed of said DDP along said DPP.

4. The drug delivery system of claim 1 wherein said LPG is configured to adjust laser radiation energy generated by said FLS and imparted to said DDD to affect drug delivery flow of said DDP along said DPP.

5. The drug delivery system of claim 1 wherein said DDD comprises a form factor selected from a group consisting of: capsule; button; disc; pouch; tab; and intraocular lens (IOL).

6. The drug delivery system of claim 1 wherein said DPP comprises a pathway pattern selected from a group consisting of: helix; spiral; rectangular helix; rectangular spiral; serpentine; radial; lines of different width; and pathways of varying cross section.

7. The drug delivery system of claim 1 wherein said DDD comprises an acrylic material incorporating an ultraviolet (UV) absorber having a concentration of 10% or less by volume.

8. The drug delivery system of claim 1 wherein said DDD comprises an internal drug delivery reservoir (DDR) configured to accept said DDP.

9. The drug delivery system of claim 1 wherein said DDD comprises an internal refillable drug delivery reservoir (DDR) configured to accept said DDP.

10. The drug delivery system of claim 1 wherein said DDD comprises an identifying indicia locating an external delivery port (EDP), said identifying indicia selected from a group consisting of: index face; bump; and notch.

11. The drug delivery system of claim 1 wherein said DDD comprises an external delivery port (EDP).

12. The drug delivery system of claim 1 wherein said DDD is configured to accept injection of said DDP via the use of a needle syringe.

13. The drug delivery system of claim 1 wherein said DDD is configured to seal a drug delivery reservoir (DDR) after injection of said DDP into said DDR via the use of a needle syringe.

14. The drug delivery system of claim 1 wherein said CCD is configured to allow for a customized hydrophilicity change depth within said DDD to control drug delivery speed of said DDP within said DPP.

15. The drug delivery system of claim 1 wherein said CCD is configured to allow for a customized hydrophilicity change width within said DDD to control drug delivery speed of said DDP within said DPP.

16. The drug delivery system of claim 1 wherein said CCD is configured to allow for a customized hydrophilicity change depth within said DDD to control drug delivery flow of said DDP within said DPP.

17. The drug delivery system of claim 1 wherein said CCD is configured to allow for a customized hydrophilicity change width within said DDD to control drug delivery flow of said DDP within said DPP.

18. The drug delivery system of claim 1 wherein said CCD is configured to accept patient specific information to customize said DPP based on specific requirements of said patient.

19. The drug delivery system of claim 1 wherein said DDD comprises biological tissue that is receptive to a two-photon hydrophilicity change and said LPG is configured to modify the hydrophilicity of said biological tissue via radiation from said FLS.

20. The drug delivery system of claim 1 wherein said DDD comprises biological tissue that is receptive to a two-photon hydrophilicity change and wherein said LPG is configured to modify said biological tissue via radiation from said FLS to increase water flow within said biological tissue via activation of a hydrophilicity change imparted on said biological tissue by said FLS.

\* \* \* \* \*